US008318708B2

(12) United States Patent
Evans et al.

(10) Patent No.: US 8,318,708 B2
(45) Date of Patent: Nov. 27, 2012

(54) USE OF VITAMIN D RECEPTOR AGONISTS, LIGANDS, AND PRECURSORS TO TREAT PANCREATIC FIBROSIS

(75) Inventors: Ronald M. Evans, La Jolla, CA (US); Michael Downes, San Diego, CA (US); Christopher Liddle, New South Wales (AU); Nanthakumar Subramaniam, New South Wales (AU); Caroline Flora Samer, Geneva (CH)

(73) Assignees: Salk Institute for Biological Studies, La Jolla, CA (US); University of Sydney, Sydney (AU)

( * ) Notice: Subject to any disclaimer, the term of this patent is extended or adjusted under 35 U.S.C. 154(b) by 0 days.

(21) Appl. No.: 12/772,981

(22) Filed: May 3, 2010

(65) Prior Publication Data

US 2011/0014126 A1 Jan. 20, 2011

Related U.S. Application Data

(63) Continuation-in-part of application No. 12/266,513, filed on Nov. 6, 2008, now abandoned.

(60) Provisional application No. 60/985,972, filed on Nov. 6, 2007.

(51) Int. Cl.
*A61K 31/59* (2006.01)
*A61K 31/592* (2006.01)
*A61K 31/593* (2006.01)

(52) U.S. Cl. .................................................. 514/167

(58) Field of Classification Search ........................ None
See application file for complete search history.

(56) References Cited

U.S. PATENT DOCUMENTS

| | | |
|---|---|---|
| 6,358,939 B1 | 3/2002 | Hayes et al. |
| 2005/0009793 A1 | 1/2005 | Curd |
| 2005/0124591 A1 | 6/2005 | Tian et al. |
| 2005/0148557 A1 | 7/2005 | Tian et al. |
| 2006/0074109 A1 | 4/2006 | Polvino et al. |
| 2006/0135610 A1 | 6/2006 | Bortz et al. |
| 2006/0178351 A1 | 8/2006 | Curd et al. |
| 2006/0240150 A1 | 10/2006 | Delaney et al. |
| 2009/0209500 A1 | 8/2009 | Evans et al. |
| 2010/0099640 A1* | 4/2010 | Geuns et al. ................ 514/34 |

FOREIGN PATENT DOCUMENTS

WO WO 2009/061961 A1 5/2009

OTHER PUBLICATIONS

Suda et al., Am. J. Gastroenterology, (Nov. 1994), 89(11), pp. 2060-2062 (Abstract).*
Whitcomb, DC, Annual Rev. Med. (2010), 61, pp. 413-424 (Abstract).*
Dunlop et al., Journal of Molecular Biology, (Jun. 2005), 349(2), pp. 248-260.*
Kloppel et al., Virchows Arch., (2004), 445:1-8.*
Dai et al., J. Derm. Sci. (Apr. 2008), 50(1), pp. 53-60.*
Jonas et al., "Measurement of Parenchymal Function and Bile Duct Flow in Primary Sclerosing Cholangitis Using Dynamic $^{99m}$Tc-HIDA SPECT," *J. Gastroenterol. Hepatol.* 21:674-681, 2006.
Cao et al., "Leptin Stimulates Tissue Inhibitor of Metalloproteinase-1 in Human Hepatic Stellate Cells," *J. Biol. Chem.* 279:4292-4304, 2004.
Cohen-Lahav et al., "The Anti-Inflammatory Activity of 1,25-Dihydroxyvitamin D3 in Macrophages," *J. Steroid. Biochem. Mol. Biol.* 103:558-562, 2007.
Gascon-Barré et al., "The Normal Liver Harbors the Vitamin D Nuclear Receptor in Nonparenchymal and Biliary Epithelial Cells," *Hepatology* 37:1034-1042, 2003.
Johnson et al., "The Activated Mesangial Cell: A Glomerular 'Myofibroblast'?," *J. Am. Soc. Nephrol.* 2:S190-S197, 1992.
Omary et al., "The Pancreatic Stellate Cell: A Star on the Rise in Pancreatic Diseases," *J. Clin. Invest.* 117:50-59, 2007.
Petta et al., "Low Vitamin D Serum Level is Related to Severe Fibrosis and Low Responsiveness to Interferon-Based Therapy in Genotype 1 Chronic Hepatitis C," *Hepatology* 51:1158-1167, 2010.
Samer et al., "Rat Primary and Immortalized Human Hepatocytes Express an Inducible and Functional Vitamin D Receptor," Abstract, Hepatology & Luminal Research Workshop & Clinical Update on Non-Invasive Markers of Liver Injury and Early Diagnosis of Liver Disease, May 1-3, 2009, Yarra Valley, Victoria, Australia.
Tan et al., "Paricalcitol Attenuates Renal Interstitial Fibrosis in Obstructive Nephropathy," *J. Am. Soc. Nephrol.* 17:3382-3393, 2006.
Tan et al., "Therapeutic Role and Potential Mechanisms of Active Vitamin D in Renal Interstitial Fibrosis," *J. Steroid. Biochem. Mol. Biol.* 103:491-496, 2007.
Zehnder et al., "Expression of 25-Hydroxyvitamin D3-1alpha-hydroxylase in the Human Kidney," *J. Am. Soc. Nephrol.* 10:2465-2473, 1999.
Zollner et al., "Role of Nuclear Receptors in the Adaptive Response to Bile Acids and Cholestasis: Pathogenetic and Therapeutic Considerations," *Mol. Pharm.* 3:231-251, 2006.

* cited by examiner

*Primary Examiner* — Phyllis G. Spivack
(74) *Attorney, Agent, or Firm* — Klarquist Sparkman, LLP

(57) ABSTRACT

This application relates to methods of treating and ameliorating fibrosis, such as fibrosis of the pancreas. In particular, the application relates to methods of using a vitamin D receptor agonist (such as vitamin D, vitamin D analogs, vitamin D precursors, and vitamin D receptor agonists precursors) for the treatment of pancreatic fibrosis.

12 Claims, 19 Drawing Sheets

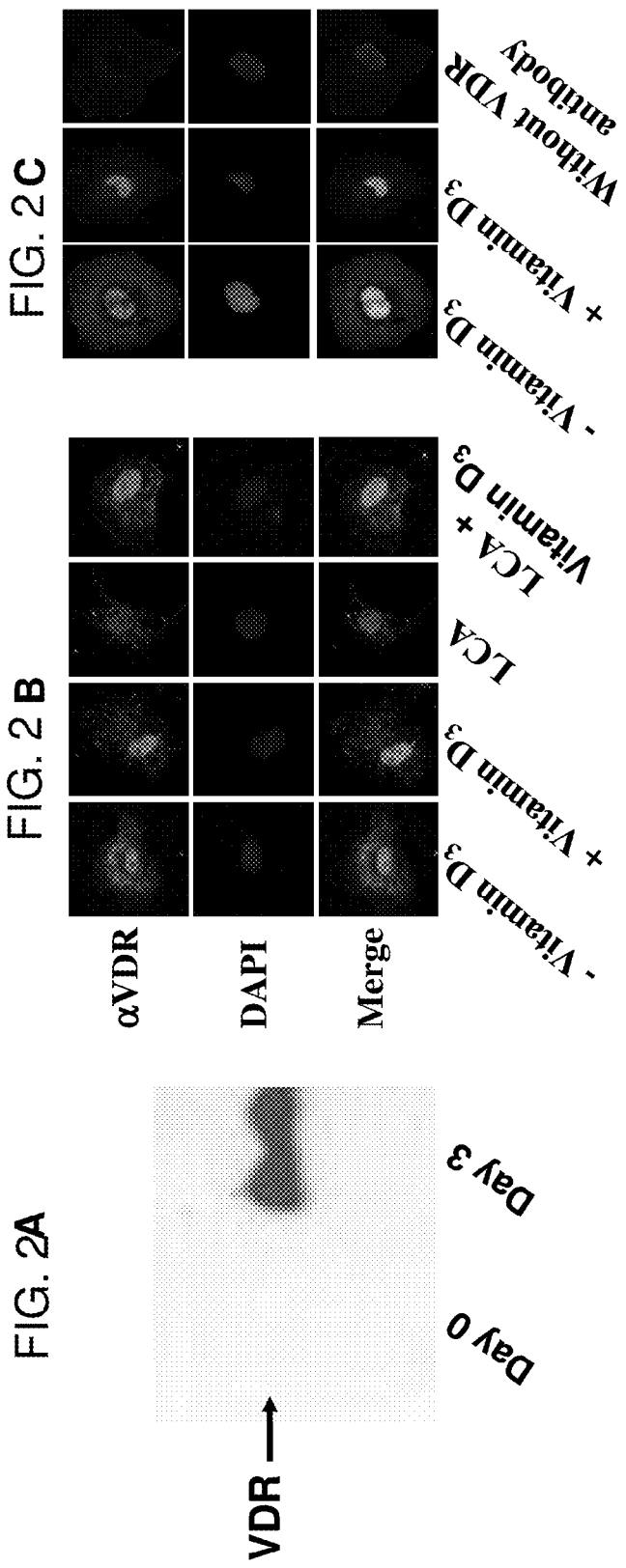

☐ CYP27A1  ■ CYP27B1

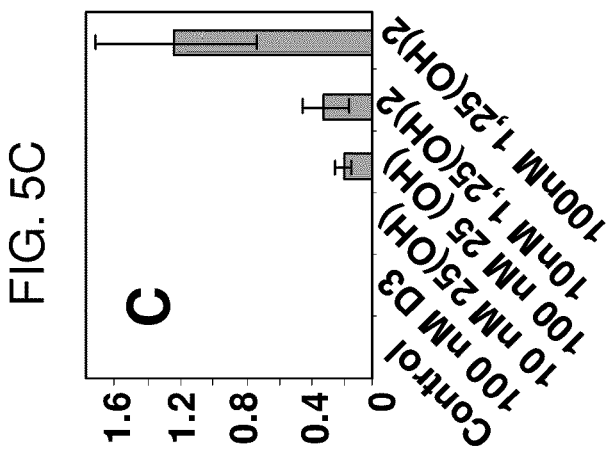
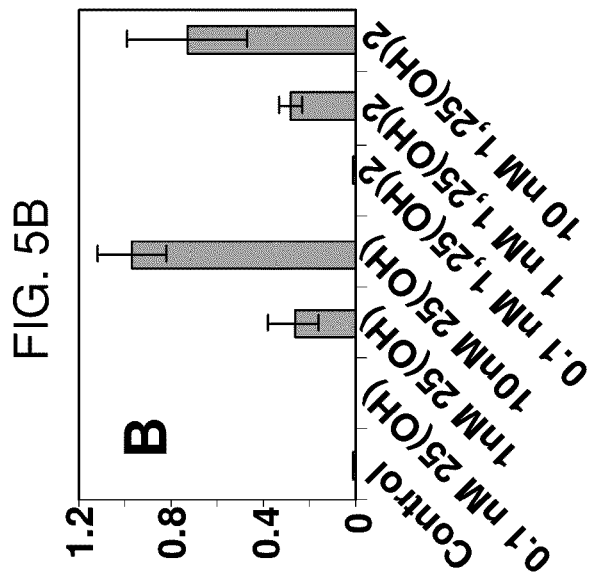
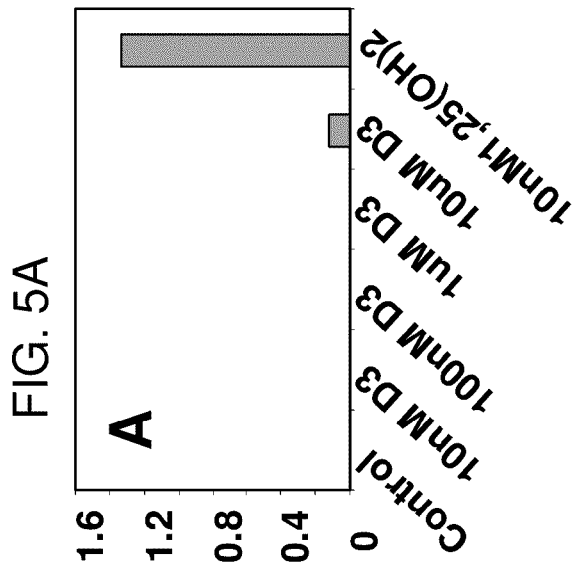

USE OF VITAMIN D RECEPTOR AGONISTS, LIGANDS, AND PRECURSORS TO TREAT PANCREATIC FIBROSIS

CROSS REFERENCE TO RELATED APPLICATIONS

This application is a continuation-in-part of U.S. application Ser. No. 12/266,513 filed Nov. 6, 2008, now abandoned which claims priority to U.S. Provisional Application No. 60/985,972 filed Nov. 6, 2007, both herein incorporated by reference.

ACKNOWLEDGMENT OF GOVERNMENT SUPPORT

Aspects of this invention were made with United States government support under grant no. DK062434-05 from the National Institutes of Health (NIH), and grant nos. 402493 and 512354 from the National Health and Medical Research Council of Australia (NHMRCA). The United States and Australian governments have certain rights in the invention.

FIELD

This application relates to methods of treating, preventing, and ameliorating fibrosis, such as fibrosis of the liver. In particular, the application relates to methods of using a vitamin D receptor (VDR) agonist for the treatment, prevention, and amelioration of hepatic apoptosis, cell death or liver damage (such as liver fibrosis) and thus provide a way to preserve liver function.

BACKGROUND

Hepatic fibrosis, the accumulation of abnormal extracellular matrix (ECM) proteins and a resultant loss of liver function, is an accompaniment of an inflammation-driven wound healing process triggered by chronic liver injury. The main causes of liver injury leading to fibrosis in Western societies include chronic hepatitis C virus (HCV) infection, alcohol abuse, chronic hepatitis B (HBV) infection, iron overload as occurs in hereditary hemochromatosis, and increasingly, non-alcoholic steatohepatitis (NASH). The inflammatory process ensuing from hepatic injury triggers a variety of cellular responses including cell repair, hepatocyte regeneration, increased extracellular matrix turnover, and ultimately in some patients significant fibrosis. Progressive fibrosis of the liver eventually can result in cirrhosis, portal hypertension, liver failure, and hepatocelluar carcinoma.

Given the foregoing, it would be desirable to have methods of treating, preventing, and ameliorating fibrosis, such as fibrosis of the liver.

SUMMARY

Described herein are methods of treating fibrosis that are based on the unexpected discovery that a specialized subset of cells within the liver respond to compounds that bind to or activate the vitamin D receptor (VDR, NR1I1) to influence the processes of liver injury, inflammation and fibrogenesis. Cells that express and respond to the VDR in liver include, but are not limited to hepatic stellate cells (HSCs), myofibroblasts, Kupffer cells (KCs), and sinusoidal endothelial cells (SECs). These cells types are frequently referred to as hepatic non-parenchymal cells (NPCs). In addition, there are similar specialized cells within the pancreas and kidney that respond in a similar manner, including but not limited to pancreatic stellate cells and renal mesangial cells.

It is also unexpectedly shown herein that in the presence of the profibrotic molecule transforming growth factor-beta 1 (TGF-$\beta_1$), hepatocytes are also capable of responding to compounds that bind to and activate the vitamin D receptor, through induced expression of vitamin D receptor. On the basis of this observation, it is proposed that VDR signaling in hepatocytes acts as a survival and differentiation factor for these cells in the face of injury where TGF-$\beta_1$ is produced in the local hepatic micro environment. For example, when liver injury occurs TGF-$\beta_1$ is produced from the non-parenchymal cells of the liver (e.g., Kupffer cells) and possibly inflammatory cells recruited from the circulation. The relevance of these observations to hepatic fibrosis is that vitamin D receptor ligands and their precursors will act to attenuate liver injury, and therefore facilitate the wound healing response, by acting to preserve liver function by promoting survival of hepatocytes, the predominant cell type comprising the liver.

Thus, one embodiment of the disclosure is a method of treating liver fibrosis in a subject. The method can include administering a therapeutically effective amount of vitamin D receptor agonist (such as 1α,25 dihydroxyvitamin $D_3$, (1,α25-(OH)$_2$-D3) or a precursor thereof, a vitamin D analog, a vitamin D receptor ligand, or a vitamin D receptor agonist precursor), to a subject having a fibrosis or at risk for developing fibrosis, thereby treating the liver fibrosis. In some examples, hepatocytes of the liver are exposed to therapeutically effective amounts of TGF-$\beta_1$ (for example in an amount sufficient to induce VDR expression), such as TGF-$\beta_1$ produced by the liver during fibrogenesis or by administering TGF-$\beta_1$ to the subject.

The foregoing and other objects and features of the disclosure will become more apparent from the following detailed description, which proceeds with reference to the accompanying figures.

BRIEF DESCRIPTION OF THE DRAWINGS

FIG. 1A shows a comparison of NHR family expression in murine liver and isolated primary HSCs.

FIGS. 2A-C is a set of digital images showing VDR expression in primary rat HSC and in human LX-2 cell line. (A) 20 µg of whole cell extracts from day 0 and day 3 rat HSCs were analyzed by western immunoblot analysis using a VDR-specific monoclonal antibody and it showed that VDR is present in day 3 hepatic stellate cells. (B & C) VDR was detected in both cytoplasm and nuclei in the absence of 1α,25(OH)$_2$ vitamin $D_3$ or lithocholic acid (LCA) but in the presence of these ligands intense nuclear staining was observed by immuno-labelling using a VDR-specific monoclonal antibody of (B) rat HSC and (C) human LX-2 cells followed by visualization with a fluorescence microscope. DAPI was used to localize the nuclei.

FIGS. 5A-C are bar graphs showing the impact of $1\alpha,25(OH)_2$ vitamin D3 and vitamin D precursors on Cyp24a1 expression in quiescent and activated primary rat HSCs in cultured on plastic. (A) Quiescent HSCs, which had been maintained in culture on plastic for 40 h, were treated for 24 h with vitamin D precursors cholecalciferol (vitamin D3) or calcidiol (25-OH vitamin D3). (B) HSCs cultured as above were treated for 24 hours with 25-OH vitamin D3 or $1\alpha,25(OH)_2$ vitamin D3. (C) HSCs activated by culture on plastic for 7 days were treated with different concentrations of vitamin D3, 25-OH vitamin D3 or $1\alpha,25(OH)_2$ vitamin D3 for 24 hours. Expression levels of Cyp24a1 mRNA was determined by quantitative real time PCR (qPCR).

SEQUENCE LISTING

Figure 1A:
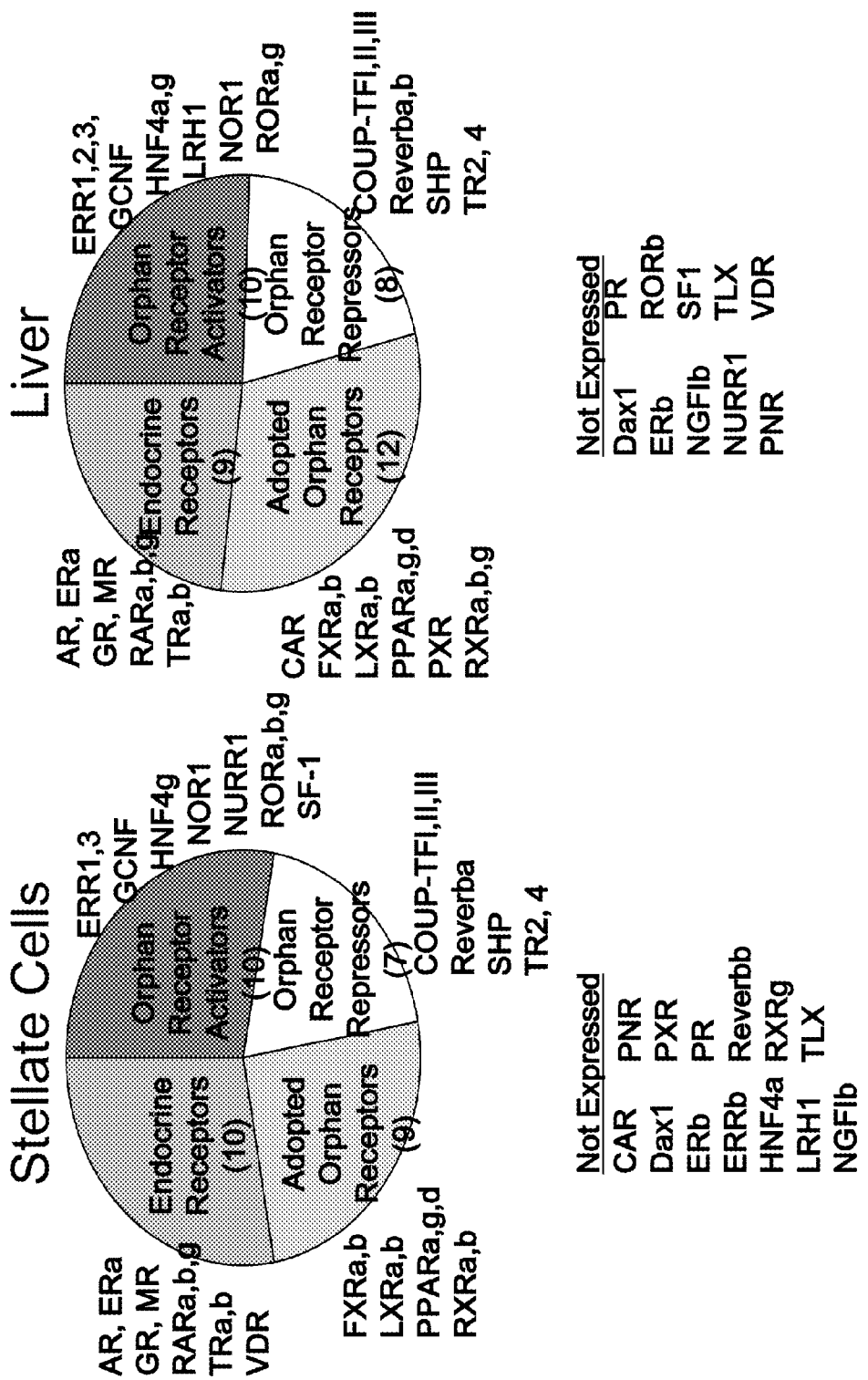
FIGS. 1A and B are a series of graphs showing expression patterns of nuclear hormone receptors (NHRs).

The nucleic acid sequences listed in the accompanying sequence listing are shown using standard letter abbreviations for nucleotide bases. Only one strand of each nucleic acid sequence is shown, but the complementary strand is understood as included by any reference to the displayed strand.

SEQ ID NOS: 1 and 2 are primers used to amplify rat Cyp27b1.
SEQ ID NOS: 3 and 4 are primers used to amplify rat Cyp24a1.
SEQ ID NOS: 5 and 6 are primers used to amplify rat Cyp27a1
SEQ ID NOS: 7 and 8 are primers used to amplify human CYP24A1.
SEQ ID NOS: 9 and 10 are primers used to amplify human CYP27A1.
SEQ ID NOS: 11 and 12 are primers used to amplify human CYP27B1.
SEQ ID NOS: 13 and 14 are primers used to amplify rat Sp1.
SEQ ID NOS: 15 and 16 are primers used to amplify rat VDR.
SEQ ID NOS: 17 and 18 are primers used to amplify rat Hnf4$\alpha$.

DETAILED DESCRIPTION

I. Overview of Several Embodiments

The embodiments disclosed herein are based on the surprising discovery that vitamin D receptor (VDR) agonists (including vitamin D precursors, vitamin D analogs, $1\alpha,25$ (OH)$_2$-D$_3$, VDR ligands, and precursors of VDR agonists) are useful for the treatment of fibrosis, for instance hepatic fibrosis. It is shown herein that TGF-$\beta_1$ alone, as well as in combination with a VDR agonist, significantly increases expression of VDR by liver hepatocytes.

Thus, described herein is a method of treating liver fibrosis in a subject. The disclosed methods are also suitable for preventing liver fibrosis in a subject. The method in particular examples includes administering a therapeutically effective amount of vitamin D receptor agonist to a subject having a liver fibrosis, thereby treating the fibrosis. Exemplary vitamin D receptor agonists include but are not limited to vitamin D, a vitamin D precursor, a vitamin D analog, a vitamin D receptor ligand, a vitamin D receptor agonist precursor, or combinations thereof. In certain embodiments, the treatment is a VDR agonist precursor such as 25-hydroxy-vitamin D$_3$ (25-OH-D$_3$) (calcidiol); vitamin D$_3$ (cholecalciferol); vitamin D$_2$ (ergocalciferol), or combinations thereof. In certain embodiments, the treatment is an agonist ligand of VDR, such as 1$\alpha$,25-dihydroxyvitamin D$_3$ (calcitriol). In some examples hepatocytes are exposed to therapeutic amounts of TGF-$\beta_1$, for example injury to the liver can cause cells of the liver to secrete TGF-$\beta_1$, thus exposing hepatocytes to TGF-$\beta_1$ in amounts sufficient to induce expression of VDR, such as an increase of at least 2-fold or at least 5-fold. In some examples, for example in a laboratory mammal, therapeutic amounts of TGF-$\beta_1$ are administered to induce heptatocytes to express VDR. In some examples, hepatocytes of the subject to be treated express at least 2-fold more VDR relative to hepatocytes in a subject not having liver fibrosis, such as an at least 3-fold, 4-fold, 5-fold, or at least 10-fold increase. Thus, in some examples subjects having a liver fibrosis or having a liver disease are selected for treatment with the disclosed methods (for example to treat an existing fibrosis or to prevent or delay the development of fibrosis).

In certain examples, the fibrosis is a fibrosis of the liver and administration includes oral or parenteral administration of the VDR agonist. In particular examples, the VDR agonist is a vitamin D precursor is administered at a dose of at least 1 international units (IU), such as at least 5 IU, at least 10 IU, at least 10 IU, at least 100 IU, at least 1000 IU, at least 5000 IU, at least 10,000 IU, at least 50,000 IU, at least 100,000 IU, or at least 500,000 IU, for example from 5 IU about 50,000 IU, 5 IU to 10,000 IU, 10 to 1000 IU, or 50,000 IU to 500,000 IU. Generally, an IU is unit of measurement for the amount of a substance, such as a vitamin D precursor, based on specific biological activity or effect as defined by an international body and accepted internationally. In some examples, for vitamin D 1 IU is the biological equivalent of 0.025 µg cholecalciferol/ergocalciferol.

Some embodiments pertain to fibrosis of the liver, and administration includes contacting liver hepatocytes with the VDR agonist thereby treating the fibrosis. In certain examples, the subject is a mammalian subject, such as a human or other primate. In one example, a mammal is administered one or more VDR agonists (and in some examples also TGF-$\beta$1) over a period of at least 1 day, at least 7 days, at least 14 days, at least 30 days, at least 60 days, at least 6 months, at least 1 year, at least 2 years or at least 5 years.

Also disclosed herein is a method of screening for an agent that can treat fibrosis. The method includes contacting a hepatocyte with one or more test agents, and detecting production of biologically active vitamin D receptor agonists or calcitriol by the cell, wherein test agents that result in the production of a biologically active VDR agonist including but not restricted to 1$\alpha$,25-dihydroxyvitamin D$_3$ by the cell are agents that can treat fibrosis. In particular embodiments, the test agent includes a VDR agonist. The hepatocyte can be a primary cell or an immortalized cell line derived from a hepatocyte, hepatocelluar carcinoma, hepatoblastoma cell or other cell line that retains some phenotypic or functional features of hepatocytes. The ability of the test reagent to either act directly as a VDR agonist or to be converted by the cell under examination into a VDR agonist can be monitored in several ways.

In one embodiment the test agent is applied and agonist VDR activity is determined by monitoring expression of VDR target genes such as Cyp24A1, though other VDR target genes may be used. In another embodiment, conversion of the test agent into a compound capable of acting as a VDR agonist can be monitored by mass spectrometry, immunoassay or other assay systems (including in vivo cell based and in vitro VDR/coactivator association assays capable of detecting specific chemical structures or families of chemical structures).

In some embodiments, the screening method also includes determining whether the VDR agonist produced by the cell can be degraded by Cyp24A1, and in other embodiments, the method also includes selecting test agents that did not result in degradation of a VDR agonist by Cyp24A1.

In still other embodiments, the method further includes determining whether the agent has hypercalcemic effects in vitro, and in certain examples the method also includes selecting test agents that did not have hypercalcemic effects in vitro. In still other embodiments, the method further includes determining whether the agent has hypercalcemic effects in vivo, and in certain examples the method also includes selecting test agents that did not have hypercalcemic effects in vivo. Additional embodiments include administering one or more of the selected test agents to a mammal having fibrosis, and determining whether the one or more test agents treat the fibrosis, and in some examples, selecting test agents that treated the fibrosis.

Also provided herein are methods of increasing expression of VDR by a hepatocyte in vivo or in vitro. The method can include contacting the hepatocyte with an amount of a VDR agonist and an amount of TGF-$\beta_1$ sufficient to increase expression of VDR by the hepatocyte. In some examples VDR expression is increased by at least 3-fold, at least 5-fold, at least 10-fold, or at least 20-fold, such as 2-fold to 50-fold, 2-fold to 20-fold, 2-fold to 10-fold, 2-fold to 5-fold, 3-fold, 4-fold, 5-fold or 6-fold, relative to VDR expression in hepatocytes not treated using the methods provided herein. Methods of measuring VDR expression are known in the art and exemplary methods are provided herein, such as western blotting or other immunohistological methods, detecting VDR mRNA expression for example using PCR, measuring CYP24A1 protein or mRNA expression, and the like.

For example, hepatocyte cells in culture can be incubated with a VDR agonist and TGF-$\beta_1$ at concentrations and for a period of time sufficient to increase expression of VDR by the hepatocyte. In one example, cells are cultured with the VDR agonist and TGF-$\beta_1$ for example at least 6 hours, at least 12 hours, at least 24 hours, or at least 48 hours, such as 24 hours. In some examples the cells are incubated with the TGF-$\beta_1$ and the VDR agonist simultaneously. In other examples, the cells are first incubated with TGF-$\beta_1$ (for example for a period of at least 1 hour, at least 6 hours, at least 1 hours, or at least 24 hours), and subsequently the VDR agonist is added. In some examples, cells are cultured with at least 1 international unit (IU), such as at least 5 IU, at least 10 IU, at least 10 IU, at least 100 IU, at least 1000 IU, at least 5000 IU, at least 10,000 IU, at least 50,000 IU, at least 100,000 IU or at least 500,000 IU, for example from 5 IU about 50,000 IU, 5 to 10,000 IU, 10 to 1000 IU, or 50,000 to 500,000 IU of one or more VDR agonists. Cells can be cultured with at least 0.1 ng/mL TGF- $\beta_1$, such as at least 0.5 ng/mL, at least 1 ng/mL, at least 5 ng/mL, at least 10 ng/mL, such as 1 to 5 ng/mL, for example 2 ng/mL TGF-$\beta_1$.

In another example, hepatocyte cells in a subject (such as a laboratory mammal, such as a rat, mouse or non-human primate) can be exposed with a VDR agonist and TGF-$\beta_1$, for example by administering the compounds to the subject, at concentrations and over a period of time sufficient to increase expression of VDR by the hepatocyte, for example using the times and concentrations provided herein for treating liver fibrosis. In one example, a mammal is administered one or more VDR agonists (and in some examples also TGF-$\beta_1$) over a period of at least 1 day, at least 7 days, at least 14 days, at least 30 days, at least 60 days, at least 6 months, at least 1 year, at least 2 years or at least 5 years. In some examples, a mammal is administered at least 1 international unit (IU), such as at least 5 IU, at least 10 IU, at least 10 IU, at least 100 IU, at least 1000 IU, at least 5000 IU, at least 10,000 IU, at least 50,000 IU, at least 100,000 IU, at least 500,000 IU, for example from 5 IU about 50,000 IU, 5 IU to 10,000 IU, 10 IU to 1000 IU, 1000 IU to 500,000 IU, or 50,000 IU to 500,000 IU of one or more VDR agonists. Optionally TGF-$\beta_1$ can be administered (for example suing an osmotic minipump) at a dose of at least 0.5 µg/kg body weight/day TGF-$\beta_1$, such as at least mg/kg body weight/day, at least 5 mg/kg body weight/day, at least 10 mg/kg body weight/day, such as 1 to 10 mg/kg body weight/day, for example 5 mg/kg body weight/day TGF-$\beta_1$.

II. Abbreviations

AP-1: activator protein 1
APC: antigen-presenting cell
BAMBI: bone morphogenic protein and activin membrane-bound inhibitor
BMT: bone marrow transplantation
CAR: constitutive androstane receptor
CCL2: chemotactic protein type 1
CV: coefficient of variation
DBD: DNA-binding domain
DCA: deoxycholic acid
ECM: extracellular matrix
ESRD: end stage renal disease
FBS: fetal bovine serum
FXR: farnesoid X receptor
HBV: hepatitis B virus
HCV: hepatitis C virus
HSC: hepatic stellate cells
ICAM-1: InterCellular Adhesion Molecule-1
IFN-$\gamma$: interferon-gamma
IL-6: interleukin 6
IL-8: interleukin 8
IL-1R: interleukin-1 receptor
IP: intraperitoneally
KC: Kupffer cells
LBD: ligand-binding domain
LCA: lithocholic acid
LPS: lipopolysaccharide endotoxin
LTR: long terminal repeats
LXR: liver X receptor
MCD: methionine- and choline-deficient
MMP: matrix metalloproteinases
NASH: nonalcoholic steatohepatitis
NF$\kappa$B: nuclear factor $\kappa\beta$
NHRs: nuclear hormone receptors
NO: nitric oxide
NPC: non-parenchymal cell
PBS: primer binding site
PCN: pregnenolone-16$\alpha$-carbonitrile
PDGF: platelet-derived growth factor
PMBC: peripheral blood mononuclear cell
PPAR: Peroxisome Proliferator-Activated Receptor
PPAR-$\alpha$: Peroxisome Proliferator-Activated Receptor-alpha
PPAR-$\Delta$: Peroxisome Proliferator-Activated Receptor-delta
PPAR-$\delta$: Peroxisome Proliferator-Activated Receptor-delta
PPAR-$\gamma$: Peroxisome Proliferator-Activated Receptor-gamma
PPT: polypurine tracts
PXR: pregnane X receptor
QPCR: quantitative real-time PCR
RT: reverse transcriptase
ROS: reactive oxygen species
RRE: Rev Responsive Element
RXR: retinoid-X receptor
SEC: sinusoidal endothelial cells
stdev: standard deviation of the average
TAR: TAT activation region
TGF-$\beta_1$: transforming growth factor beta 1
TLR: Toll-like receptor
TLR4: toll-like receptor 4
TNF$\alpha$: tumor necrosis factor alpha
UDCA: ursodeoxycholic acid
VDR: vitamin D receptor
VEGF: vascular endothelial growth factor
VSV-G: vesicular stomatitis protein G III. Terms In order to facilitate review of the various embodiments of the disclosure, the following explanations of specific terms are provided. All Genbank Accession numbers referenced herein are incorporated by reference for the sequence available on May 3, 2010

Administration: Includes oral, rectal, vaginal, transdermal, and parenteral administration. Generally, parenteral formulations are those that are administered through any possible mode except ingestion. This term also refers to injections, whether administered intravenously, intrathecally, intramuscularly, intraperitoneally, intra-articularly, or subcutaneously, and various surface applications including intranasal, inhalational, intradermal, and topical application, for instance.

CYP24A1: Refers to cytochrome P450, family 24, subfamily a, polypeptide 1, a protein that initiates the degradation of calcitriol by hydroxylation of the side chain. In regulating the level of vitamin D3, this enzyme plays a role in calcium homeostasis and the vitamin D endocrine system. Exemplary CYP24A1 protein sequences can be found in Genbank Accession Nos: CAM27343.1, AAI09085.1 and AAI09084.1.

CYP27A1: Refers to cytochrome P450, family 27, subfamily a, polypeptide 1, and convert vitamin $D_3$ to 25(OH) vitamin $D_3$, though other cytochromes P450 may also catalyze this reaction. Exemplary CYP27A1 protein sequences can be found in Genbank Accession Nos: NP_000775.1, AAH40430.1 and AAH51851.1.

CYP27B1: Refers to cytochrome P450, family 27, subfamily b, polypeptide 1, and is the enzyme which converts calcidiol to calcitriol (the bioactive form of Vitamin D). Exemplary CYP27B1 protein sequences can be found in Genbank Accession No: NP_034139, NP_000776.1 and AAP31972.1.

Fibrosis: Refers to the formation or development of excess fibrous connective tissue in an organ or tissue as a reparative or reactive process, as opposed to a formation of fibrous tissue as a normal constituent of an organ or tissue. As described herein, the term fibrosis includes at least liver/hepatic fibrosis, kidney/renal fibrosis, and pancreatic fibrosis. In particular examples the subjects treated herein have a fibrosis, such as a liver fibrosis.

Hepatic fibrosis is the accumulation of abnormal extracellular matrix (ECM) proteins and a resultant loss of liver function, and is an accompaniment of an inflammation-driven wound healing process triggered by chronic liver injury (Bataller & Brenner 2005 *J Clin Invest.,* 115(2):209-18). The most common causes of liver injury that lead to fibrosis include chronic hepatitis C virus (HCV) infection, alcohol abuse, chronic hepatitis B infection (HBV) and increasingly, nonalcoholic steatohepatitis (NASH), which represents the hepatic metabolic consequence of rising obesity and associated insulin resistance in the setting of an increasingly sedentary lifestyle (Bataller & Brenner 2005 *J Clin Invest.,* 115(2):209-18; Friedman 1999 *Am J Med.,* 107(6B):27S-30S; Siegmund et al., 2005 *Dig Dis.,* 23(3-4):264-74; Friedman & Bansal *Hepatology.,* 43(2 Suppl 1):S82-8). The inflammatory process that results from hepatic injury triggers a variety of cellular responses that include cell repair, regeneration, increased extracellular matrix turnover, and ultimately, in some patients, significant fibrosis. Progressive fibrosis of the liver eventually can result in cirrhosis, loss of liver function (decompensated cirrhosis), portal hypertension, and hepatocellular carcinoma (Bataller & Brenner 2005 *J Clin Invest.* 115(2):209-18; Friedman 2003 *J. Hepatol.* 38(Suppl. 1):S38-S53).

Without being bound by theory, hepatic fibrogenesis is thought to be the result of a wound healing process that occurs after continued liver injury in which parenchymal cells proliferate to replace necrotic or apoptotic cells. This process is associated with an inflammatory response and a limited deposition of ECM. If the hepatic injury persists, eventually hepatocytes are replaced by abundant ECM components, including fibrillar collagen. The distribution of this fibrous material within the lobular architecture of the liver depends on the origin of the liver injury. In chronic viral hepatitis and chronic cholestatic disorders, the fibrotic tissue is initially located around the portal tracts, while in alcohol-induced liver disease and NASH, it is found in the pericentral and perisinusoidal areas (Friedman 2003 *J. Hepatol.,* 38(Suppl. 1):S38-S53; Popper & Uenfriend 1970. *Am. J. Med.,* 49:707-721). As fibrotic liver diseases advance, the pathology progresses from isolated collagen bands to bridging fibrosis, and ultimately, established cirrhosis with regenerative nodules of hepatocytes encapsulated within type I collagen bands (Popper & Uenfriend 1970. *Am. J. Med.,* 49:707-721).

Renal fibrosis causes significant morbidity and mortality as the primary acquired lesion leading to the need for dialysis or kidney transplantation. Renal fibrosis can occur in either the filtering or reabsorptive component of the nephron, the functional unit of the kidney. Experimental models have identified a number of factors that contribute to renal scarring, particularly derangements of physiology involved in the autoregulation of glomerular filtration. This in turn leads to replacement of normal structures with accumulated extracellular matrix (ECM). A spectrum of changes in the physiology of individual cells leads to the production of numerous peptide and non-peptide fibrogens that stimulate alterations in the balance between ECM synthesis and degradation to favor scarring. Almost all forms of end stage renal disease (ESRD) are characterized by significant renal fibrosis.

Fibrosis of the pancreas is a characteristic feature of chronic pancreatitis of various etiologies, and is caused by such processes as necrosis/apoptosis, inflammation, and duct obstruction. The initial event that induces fibrogenesis in the pancreas is an injury that may involve the interstitial mesenchymal cells, the duct cells and/or the acinar cells. Damage to any one of these tissue compartments of the pancreas is associated with cytokine-triggered transformation of resident fibroblasts/pancreatic stellate cells into myofibroblasts and the subsequent production and deposition of extracellular matrix. Depending on the site of injury in the pancreas and the involved tissue compartment, predominantly inter(peri)lobular fibrosis (as in alcoholic chronic pancreatitis), periductal fibrosis (as in hereditary pancreatitis), periductal and interlobular fibrosis (as in autoimmune pancreatitis) or diffuse inter- and intralobular fibrosis (as in obstructive chronic pancreatitis) develops.

Hepatic non-parenchymal cells (NPCs): Include hepatic stellate cells (HSCs), Kupffer cells (KC), and sinusoidal endothelial cells (SECs). NPCs are critical for hepatocyte survival, and HSCs which have transdifferentiated into myofibroblasts are the predominant source of collagen deposition in liver (Gabele et al., 2003. *Front. Biosci.,* 8:D69-D77), with bone marrow-derived myofibroblasts contributing to pathological ECM production. While the liver is composed predominantly of hepatocytes, the three major NPC cell populations (HSCs, KCs, and SECs) impact hepatic physiology and pathophysiology to an extent greater than their absolute numbers suggest, having roles in hepatic injury, fibrosis and defense from micro-organisms and toxins (Bouwens et al., 1992. *Enzyme.,* 46(1-3):155-68).

HSCs are vitamin A-storing cells located in the space of Disse, between the sinusoidal endothelium and hepatocytes. Upon activation, for example by oxidative stress or TGFβ, these cells undergo a phenotypic change to myofibroblasts and secrete a range of pathological matrix components that lead to hepatic scarring (for instance, fibrosis and cirrhosis) (Bataller & Brenner 2005 *J Clin Invest.,* 115(2):209-18; Gabele et al., 2003. *Front. Biosci.,* 8:D69-D77). KCs, the resident liver macrophages, represent a significant source of chemoattractant molecules for cytotoxic CD8 and regulatory T cells. Their role in fibrosis is well established as they are one of the main sources of both $TGF\beta_1$ production and oxidative stress (via NADPH-oxidase), which leads to the transformation of HSCs into myofibroblasts (Kolios et al., 2006 *World J Gastroenterol.,* 14; 12(46):7413-20). SECs are not simply barrier cells that line the hepatic sinusoids and restrict the access of blood-borne compounds to the liver parenchyma. They are functionally specialized cells that have roles, including receptor-mediated clearance of endotoxin, bacteria and other compounds, in addition to regulation of inflammation, leukocyte recruitment and host immune responses to pathogens (Lalor et al., 2006 *World J Gastroenterol.,* 14; 12(34): 5429-39).

Hepatic stellate cells (HSCs): Include pericytes found in the perisinusoidal space (a small area between the sinusoids and hepatocytes) Of the liver. The hepatic stellate cell is the major cell type involved in liver fibrosis, which is the formation of scar tissue in response to liver damage. Stellate cells can be selectively stained with gold chloride, but their distinguishing feature in their quiescent (non-activated) state in routine histological preparations is the presence of multiple vitamin A-rich lipid droplets in their cytoplasm, which autofluoresce when exposed to ultraviolet (UV) light.

In the normal liver, stellate cells exist in a quiescent state. Quiescent stellate cells represent 5-8% of the total number of liver cells. Each cell has several long protrusions that extend from the cell body and wrap around the sinusoids. The lipid droplets in the cell body store vitamin A. Without being bound by theory, quiescent hepatic stellate cells are thought to play a role in physiological (normal) ECM production and turnover as well as acting as a liver-resident antigen-presenting cell, presenting lipid antigens to and stimulating proliferation of NKT cells.

When the liver is damaged, stellate cells can change into an activated state. The activated stellate cell is characterized by proliferation, contractility, and chemotaxis. The amount of stored vitamin A decreases progressively in liver injury. The activated stellate cell is also responsible for secreting excessive and pathological ECM components as well as reduced production of matrix degrading enzymes, which leads to fibrosis.

Hepatocyte: The predominant cell type of the liver, making up about 70-90% of the liver's cellular mass. Hepatocytes serve many roles including synthesis of proteins and lipids, metabolism of waste products and energy homeostasis. Under normal conditions, hepatocytes express virtually no detectable VDR and are unresponsive to VDR agonist ligands. However, it is shown herein that exposure of hepatocytes to TGF-$\beta_1$, a profibrogenic factor in the liver, causes hepatocytes to express VDR in substantially larger amounts (such as at least 5-fold greater; see e.g., FIG. 14). In addition, exposure of hepatocytes to a VDR agonist (such as calcitriol) combined with TGF-$\beta_1$ results in a synergistic induction of VDR expression (see e.g., FIG. 15)

Hypercalcemia: An elevated calcium level in the blood, which can be caused by, for instance, elevated levels of 1$\alpha$,25 (OH)$_2$-VitD3 (Normal range: about 8.5 to 10.2 mg/dL or 2.2-2.6 mmol/L). It can be an asymptomatic laboratory finding, but because an elevated calcium level is often indicative of other diseases, a diagnosis should be undertaken if it persists. It can be due to excessive skeletal calcium release, increased intestinal calcium absorption, or decreased renal calcium excretion.

Hypercalcemia per se can result in fatigue, depression, confusion, anorexia, nausea, vomiting, constipation, pancreatitis or increased urination. Abnormal heart rhythms also can result, and EKG findings of a short QT interval and a widened T wave suggest hypercalcemia.

Symptoms are more common at high calcium levels (12.0 mg/dL or 3 mmol/l). Severe hypercalcemia (above 15-16 mg/dL or 3.75-4 mmol/l) is considered a medical emergency: at these levels, coma and cardiac arrest can result.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

P450: Include primarily membrane-associated proteins, located either in the inner membrane of mitochondria or in the endoplasmic reticulum of cells. P450 proteins metabolize thousands of endogenous and exogenous compounds. Most P450 proteins can metabolize multiple substrates, and many can catalyze multiple reactions, which accounts for their central importance in metabolizing an extremely large number of endogenous and exogenous molecules. In the liver, these substrates include drugs and toxic compounds as well as metabolic products such as bile acids (an elimination pathway for cholesterol). Cytochrome P450 enzymes are present in many other tissues of the body including the mucosa of the gastrointestinal tract, and play roles in hormone synthesis and breakdown (including estrogen and testosterone synthesis and metabolism), cholesterol synthesis, and vitamin D synthesis and metabolism. The Human Genome Project has identified more than 63 human genes (57 full genes and 5 pseudogenes) coding for the various cytochrome P450 enzymes.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compositions herein disclosed. For example a VDR agonist can be administered in the presence of on or more pharmaceutically acceptable carriers.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for instance, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

Pharmaceutical agent or drug: A chemical compound or composition capable of inducing a desired therapeutic or prophylactic effect when properly administered to a subject. As used herein, pharmaceutical agents include, but are not limited to a vitamin D receptor agonist (such as calcitriol) as well as other types of drugs, such as anti-infective agents, for instance antibiotics, anti-fungal compounds, anti-viral compounds, and hyper-immune globulin, and anti-inflammatory agents.

Subject: Living multi-cellular vertebrate organisms, a category that includes both human and non-human mammals. The methods and compositions disclosed herein have equal applications in medical and veterinary settings. Therefore, the general term "subject" is understood to include all animals, including, but not limited to, humans or veterinary subjects, such as other primates (including monkeys), dogs, cats, horses, and cows.

Therapeutically effective amount: An amount of a therapeutic agent (such as vitamin D, a vitamin D receptor agonist, or a vitamin D precursor or TGF-$\beta_1$), alone or in combination with other agents sufficient to prevent advancement of a disease, to cause regression of the disease, or which is capable of relieving symptoms caused by the disease, such as a symptom associated with fibrosis of the liver, pancreas or kidney, for example fever, respiratory symptoms, pain or swelling.

Transforming growth factor-$\beta_1$ (TGF-$\beta_1$): A secreted protein that performs many cellular functions, including the control of cell growth, cell proliferation, cell differentiation and apoptosis (OMIM 190180). The secreted protein is cleaved into a latency-associated peptide (LAP) and a mature TGFB1 peptide, and is found in either a latent form composed of a TGFB1 homodimer, a LAP homodimer, and a latent TGFB1-binding protein, or in an active form composed of a TGFB1 homodimer. The mature peptide may also form heterodimers with other TGF-β family members. This gene is frequently upregulated in tumor cells, and mutations in this gene result in Camurati-Engelmann disease.

Exemplary TGF-β$_1$ protein sequences can be found in Genbank Accession No: NP_000651, NP_035707 and AAH22242.1. Exemplary TGF-β$_1$ peptides that can be used in accordance with the present disclosure include human, recombinant expressed TGF-β$_1$ from Sigma-Aldrich (Catalog number T7039).

Treating a disease: "Treatment" refers to a therapeutic intervention that ameliorates a sign or symptom of a disease or pathological condition (for instance, fibrosis) after it has begun to develop. As used herein, the term "treatment" also encompasses "prevention," which refers to inhibiting the full development of a disease, for example in a person who is known to have a predisposition to a disease such as a person who has been or is at risk for developing fibrosis of the liver, pancreas or kidney.

Vitamin D: A group of fat-soluble secosteroid prohormones and hormones, the two major forms of which are vitamin D2 (ergocalciferol) and vitamin D3 (cholecalciferol), which are converted to 1α,25 dihydroxyvitamin D$_3$ (1,α25-(OH)$_2$-D3), also known as calcitriol, the physiologically active form of vitamin D.

Vitamin D agonist or analog: Any compound, synthetic or natural, that binds to and activates the vitamin D receptor, such as a VDR ligand (e.g., calcitriol), VDR agonist precursor, vitamin D analogs, vitamin D precursors. Specific, non-limiting examples of natural and synthetic vitamin D agonists and analogs include 1α,25(OH)$_2$D$_3$, LG190090, LG9190119, LG190155, LG190176, and LG190178 (see, for instance, Boehm et al., (1999) *Chemistry & Biology*, 6:265-275); LY2108491, and LY2109866 (Ma et al., (2006) *J Clin. Invest.*, 116:892-904); 2β-(3-Hydroxypropoxy)1α,25-Dihydroxyvitamin D$_3$ (ED-71) (Tsurukami et al., (1994) *Calcif. Tiss. Int.* 54:142-149); EB1089 (Pepper et al., (2003) *Blood*, 101:2454-2460); OCT(22-oxa-calcitrol) (Makibayashi et al., (2001) *Am. J. Path.*, 158:1733-1741); (1αOH-2,19-nor-25hy-droxyvitaminD$_3$) and (1,3-Deoxy-2-CHCH$_2$OH-19-nor-25-hydroxyvitaminD3) (Posner et al., (2005) *Bioorganic & Medicinal Chemistry*, 13:2959-2966) and any of the vitamin D analogs disclosed in Rey et al., (1999) *J. Organic Chem.*, 64:3196-3206; and bile acid derivatives such as lithochoic acid (LCA) and ursodoxycholic acid (UDCA) (see, for instance, Nehring et al., (2007) *PNAS*, 104:10006-10009; Makishima et al., (2002) *Science*, 296:1313-1316; Copaci et al., (2005) *Rom. J. Gastroenterol.*, 14:259-266). Each of these references is hereby incorporated by reference in its entirety.

Vitamin D precursor: Any compound capable of being converted to an agonist of the vitamin D receptor by an enzyme. In certain, non-limiting examples, that enzyme is CYP27B1. Specific, non-limiting examples of vitamin D precursors include vitamin D$_3$ (cholecalciferol), 25-hydroxy-vitamin D$_3$ (25-OH-D$_3$) (calcidiol), as well as vitamin D2 (ergocalciferol) and its precursors.

Vitamin D receptor (VDR): A member of the steroid hormone family of nuclear receptors. VDR possesses the common nuclear receptor structure, for example, is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, and binding to response elements present in target genes. VDR is known to regulate genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment. The VDR/RXR heterodimer is non-permissive, in that the presence or absence of RXR ligands is not known to affect VDR responses.

Until recently the only known physiological ligand for VDR was 1α,25(OH)$_2$D3 (calcitriol): However, specific bile acids such as LCA and some derivatives (LCA-acetate, LCA-formate, 3-keto LCA) also can activate VDR.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

The singular terms "a," "an," and "the" include plural referents unless context clearly indicates otherwise. "Comprising" means "including." "Comprising A or B" means "including A," "including B," or "including A and B."

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification.

IV. Description of Several Specific Embodiments

A. Treatment and Prevention of Fibrosis

Described herein is the unexpected discovery that a specialized subset of cells within the liver, kidney, and pancreas responds to compounds that bind to or activate the vitamin D Receptor (VDR, NR1I1) to influence the processes of injury, inflammation and fibrogenesis. Cells that express and respond to the VDR in liver include but are not limited to the hepatic stellate cells (HSCs), myofibroblasts, Kupffer cells (KC), and sinusoidal endothelial cells (SECs). These cells types are frequently referred to as hepatic non-parenchymal cells (NPCs). Cells that express and respond to the VDR in pancreas and kidney include but not limited to pancreatic stellate cells and renal mesangial cells. Also disclosed herein is the unexpected discovery that hepatocytes can be induced to express VDR by exposure of the hepatocytes to TGF-β$_1$ alone or in combination with a VDR agonist such as calcitriol.

The present disclosure provides a method of treating or preventing fibrosis, comprising; administering to a subject having a fibrosis a therapeutic composition comprising a VDR agonist (such as calcitriol or a precursor or analog thereof, as well as other VDR ligands, VDR agonist precursors, vitamin D precursors and analogs and combinations thereof). It is not intended that the present disclosure be limited to any particular subject. Indeed, a variety of subjects are contemplated. In one example, the subject is a mammal, such as a human, horse, non-human primate, dog, and cat. In an additional embodiment, the subject is on a low calcium diet. In one example, the VDR agonist is administered to a patient after the surgical removal of damaged tissue (e.g., fibrotic tissue). In a specific example, the present disclosure provides a method of treatment, which includes providing a human patient with features or symptoms of fibrosis a therapeutic composition including a VDR agonist, and administering the therapeutic composition to the patient under conditions such that said features or symptoms (such as portal hypertension and its complications, hepatocellular failure and hepatocellular carcinoma) are reduced. For example, the subject to be treated can have a fibrotic liver disease (such as liver fibrosis wherein the liver produces sufficient amounts of TGF-$\beta_1$ to induce the hepatocytes to express VDR).

In one embodiment, the subject is suffering from symptoms of fibrosis of the liver, pancreas, or kidney. For example, the subject may be infected with HBV or HCV. In some examples, the administration of a therapeutic composition that includes a VDR agonist reduces the symptoms of fibrosis. In some examples, the subject is at risk for developing fibrosis (e.g., is infected with HBV or is an alcoholic or has other liver disease), and the therapeutic composition is administered prophylactically.

In one embodiment, VDR ligands or other VDR agonists that can bind to and activate the VDR are used to prevent or attenuate the processes of injury, inflammation, and fibrogenesis in the liver, pancreas and/or kidney. In some embodiments, ligands of VDR are used alone, whereas in other embodiments they are used in combination with other compositions such as nuclear receptor ligands, including but not limited to ligands for peroxisome proliferator-activated receptor-gamma (PPAR-$\gamma$, NR1C3), peroxisome proliferator-activated receptor-alpha (PPAR-$\alpha$, NR1C1) and peroxisome proliferator-activated receptor-delta (PPAR-$\delta$, NR1C2), farnesoid x receptor (FXR, NR1H4), interferon-gamma (IFN-$\gamma$), angiotensin converting enzyme inhibitors, angiotensin II receptor antagonists, ursodeoxycholic acid (UDCA), curcumin, anti-oxidants including, but not limited to vitamin E, retinoids such as Vitamin A, and therapies that deliver proteases to the liver to degrade pathological ECM. In one example, the VDR agonists are administered to a subject's whose hepatocytes have been exposed to a therapeutic amount of TGF-$\beta$1, such as a mammalian (e.g., human or rodent) TGF-[3], sufficient to increase VDR expression by the hepatocyte (such as an increase of at least 3-fold or at least 5-fold). In some examples the subject to be treated has a fibrotic liver disease wherein the liver produces sufficient amounts of TGF-$\beta_1$ to induce the hepatocytes to express VDR.

The present disclosure also provides a method of treatment, comprising, providing a subject at risk for developing fibrosis and a therapeutic composition that includes a VDR agonist (and in some examples also a therapeutically effective amount of TGF-$\beta_1$), and prophylactically administering the therapeutic compound to the subject. In a preferred embodiment, the prophylactic administration of the VDR agonist (and in some examples also TGF-$\beta_1$) delays the onset of the symptoms of fibrosis of the liver, kidney or pancreas. For example, prophylactic administration of a VDR agonist (and in some examples also TGF-$\beta_1$) prevents the onset of one or more symptoms or features of fibrosis. For example, as an organ undergoes fibrosis, the functional cellular mass of the organ is reduced as it is replaced by scar tissue (collagens and other abnormal matrix components). In addition, fibrosis causes architectural disorganization that can diminish function and lead to pathology, such as portal hypertension and increased risk of hepatocellular carcinoma in the case of the liver. Severe portal hypertension usually manifests as bleeding esophageal/gastric varices and/or ascities. In the kidney and pancreas the features of advanced fibrosis are renal failure and endocrine and/or exocrine pancreatic failure.

Treatment of hepatic NPCs with VDR agonists has profound effects on gene expression in NPCs. For example, when HSCs are cultured on plastic, they undergo a process called "activation," wherein they change phenotype from a retinol- and lipid-rich cell into an extracellular matrix-producing cell that is ultimately responsible for the production of scarring within the liver (fibrogenesis). VDR ligands prevent or retard this activation process, and reverse the process in some embodiments. Moreover, treatment of HSCs with VDR ligands markedly attenuates pro-inflammatory and pro-fibrotic gene expression induced by treating HSCs with either bacterial lipopolysaccharide endotoxin (LPS) or transforming growth factor beta 1 (TGF-$\beta$1). In particular, VDR ligands attenuate or abrogate LPS-induced pro-inflammatory chemokine production and TGF-$\beta$-induced pro-fibrotic collagen production by HSCs (Table 3). LPS is a potent activator of the innate immune system while TGF-$\beta$ is a family of three proteins that regulate differentiation, proliferation and many other functions in a wide range of cell types. Thus, VDR ligands and other VDR agonists play a therapeutic role in the prevention of liver injury, inflammation, and fibrogenesis in persons with liver diseases, including but not limited to chronic viral hepatitis (Hepatitis B and Hepatitis C infection), alcohol-induced liver disease, non-alcoholic steatohepatitis, autoimmune liver diseases, and genetic liver diseases, such as hereditary hemochromatosis, alpha$_1$-antitrysin deficiency and Wilson's disease.

In one embodiment, the VDR agonists are targeted to the liver, reducing or completely abrogating extra-hepatic effects of VDR. In another embodiment, VDR agonists are used for the treatment of injury, inflammation and fibrogenesis of the pancreas or kidney, for example for the treatment of acute or chronic pancreatitis or pancreatic fibrosis.

In some examples, 1$\alpha$,25(OH)$_2$D$_3$ or a vitamin D precursor or analog is used as a VDR agonist. It is not necessary to use the most biologically active form of vitamin D to achieve a beneficial therapeutic effect. The naturally occurring ligand of the vitamin D receptor is calcitriol. Without being bound by theory, this ligand is thought to be predominantly formed in the kidney by 1$\alpha$-hydroxylation of circulating 25-OH vitamin D$_3$ (calcidiol) by the cytochrome P450 enzyme CYP27B1. Rat and mouse HSCs as well as rat KCs and SECs express Cyp27b1, and therefore can form calcitriol from circulating precursors. In one embodiment, precursors of calcitriol (such as calcidiol) are administered to a subject, and are then converted within the target cell population to calcitriol. This approach has the advantage that the local intestinal as well as the systemic effects of calcitriol on calcium homeostasis can be significantly avoided, even when large doses of the precursor are administered.

In addition, HSCs express CYP24A1, a cytochrome P450 enzyme that terminates the biological effect of calcitriol by side chain hydroxylation. Thus, in one embodiment, a VDR ligand or other VDR agonist or agonist precursor that is resistant to deactivation by CYP24A1 is used to achieve more effective and longer lasting VDR activation in target cell populations. In specific examples, the VDR ligand is one that can be activated by CYP27B1 while being resistant to deactivation by CYP24A1. This permits VDR activation in target cell populations in the liver (for example, HSCs), pancreas and kidney, while minimizing undesirable systemic effects on calcium homeostasis.

A further embodiment is the use of a molecule that is a VDR agonist or precursor thereof that exhibits the property of high first-pass hepatic clearance due to extensive hepatic metabolism. A molecule with this property, when administered orally, is absorbed and transported to the liver via the portal vein. In the liver, the molecule activates VDR in cell populations such as hepatic stellate cells, Kupffer cells and sinusoidal endothelial cells while exhibiting minimal systemic effects on calcium homeostasis due to low systemic bioavailability.

These actions of VDR agonists on fibrosis are, in certain embodiments, monitored by blood, serum and plasma markers of liver inflammation, injury, and fibrogenesis, including but not limited to; aspartate aminotransferase, alanine aminotransferase, gamma glutamyl transpeptidase, bilirubin, alpha-2 macroglobulin, haptoglobin, tissue inhibitor of metalloproteinase-1, hyaluronic acid, amino terminal propeptide of type III collagen and other collagen precursors and metabolites, platelet count, apolipoprotein A1, C-reactive protein and ferritin. These tests are used alone in some examples, whereas in other examples they are used in combination. Hepatic fibrosis may also be monitored by the technique of transient elastography (Fibroscan™). A further embodiment includes monitoring the impact of VDR agonist treatments by direct examination of liver tissue obtained by liver biopsy.

The effects of VDR agonists on diseases of the pancreas are monitored, in some embodiments, by blood, serum, plasma amylase, or lipase, as well as tests of pancreatic exocrine and endocrine function. In other embodiments, pancreatitis is monitored by imaging techniques, including but not limited to radiological, nuclear medicine, ultrasound, and magnetic resonance.

The effects of VDR agonists on diseases of the kidney are monitored, in some embodiments, by the measurement of blood, serum, or plasma urea or creatinine, or other tests of renal function, alone or in combination. Kidney disease is monitored, in some embodiments, by imaging techniques, including but not restricted to radiological, nuclear medicine, ultrasound, and magnetic resonance. In alternate embodiments, the impact of VDR agonist treatments on the kidney is monitored by direct examination of tissue obtained by kidney biopsy.

B. Vitamin D Receptor (VDR)

Despite its relatively high expression level in NPCs, the role of VDR in these cells was unknown prior to this disclosure. VDR possesses the common nuclear receptor structure, for instance is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, (Yasmin et al., 2005. *J Biol Chem.*, 280(48):40152-60), and binding to response elements present in target genes. VDR regulates genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment (Ebert et al., 2006. *Mol Cell Endocrinol.*, 248(1-2):149-59). The VDR/RXR heterodimer is non-permissive, in that the presence or absence of RXR ligands does not affect VDR responses (Shulman et al., 2004. *Cell*, 116(3):417-29). Until recently, the only known physiological ligand for VDR was calcitriol. However, specific bile acids such as LCA and some derivatives (LCA-acetate, LCA-formate, 3-keto LCA) may activate VDR. These bile acid VDR agonists have been shown to induce SULT2A1 expression, a sulfo-conjugating phase II enzyme in intestinal mucosa, which may provide a key defense response of the intestine against the toxic and carcinogenic effects of bile acids (Chatterjee et al., 2005. *Methods Enzymol.*, 400:165-91).

C. Distribution of VDR in Hepatic Cell Populations

It was previously thought that the liver lacked VDR expression because hepatocytes, the most abundant cell population in liver, usually exhibit very low levels of the receptor: the total level of VDR in rat liver is 1,300-fold lower than in intestine. It is possible that the increase in intracellular $Ca^{2+}$ levels observed in rat hepatocytes in response to $1,\alpha25$-$(OH)_2$-D3 may be due to an unrelated membrane receptor or an indirect mechanism rather than VDR-mediated signaling (Mailhot et al., 2000. *Endocrinology.*, 141:891-900). However, $1,\alpha25$-$(OH)_2$-D3 has a significant effect on liver cell physiology during the compensatory growth process following the partial hepatectomy in the rat (Segura et al., 1999. *Histochem Cell Biol.*, 112(2):163-7; Gascon-Barre et al., 1994. *J Clin Invest.*, 93(5):2159-67). Thus, VDR expression was examined in freshly isolated hepatic NPC populations. Surprisingly, it was shown herein that VDR is abundantly expressed in HSCs, KCs and SECs isolated from normal rat livers and the VDR in these cells is fully functional as determined by the VDR-dependent induction of CYP24A1 expression by $1\alpha,25$-$(OH)_2$-D3.

It was also surprisingly found that hepatocytes can be induced to express VDR by exposing the cells to TGF-$\beta_1$. This effect can be enhanced by also exposing the cells to a VDR agonist such as $1\alpha,25$-$(OH)_2$-D3. For example contacting a hepatocyte with a VDR agonist and TGF-$\beta_1$ (e.g., "treatment") can increase VDR expression in the hepatocyte by at least 2-fold, such as at least 3-fold, at least 5-fold, at least 10-fold, at least 20-fold, or at least 100-fold, relative to VDR expression in the hepatocyte in the absence of such compounds. For example, VDR protein or mRNA expression, CYP24A1 protein or mRNA expression or nuclear hormone receptor hepatocyte nuclear factor 4a (HNF4α) protein or mRNA expression in a treated hepatocyte can be increased by at least 2-fold, such as at least 3-fold, at least 5-fold, at least 10-fold, at least 20-fold, or at least 100-fold, relative to such expression in the hepatocyte in the absence of such treatment.

D. Exemplary VDR Agonists

As described above, administration of VDR agonists can be used to treat fibrosis of the liver, kidney, and pancreas, as well as increase expression of VDR in hepatocytes. Exemplary VDR agonists include those molecules that can activate the VDR. Methods of determining if an agent is a VDR agonist are routine. For example, induction of CYP24A1 expression can be measured in cells that expressing VDR contacted with the agent, wherein an increase in CYP24A1 expression (such as a 10- to 20-fold increase in expression) indicates that the agent is a VDR agonist. Other methods include transfected reporter gene constructs and FRET assays. In some example, binding of an agonist to a purified LBD is detected by measuring induced recruitment for coactivator peptides (e.g., LXXLL). For example VDR agonists can increase CYP24A1 expression in a VDR-expressing cell by at least 20%, at least 50%, at least 75%, at least 80%, at least 90% at least 100%, at least 200% or oven at least 1000% or more as compared to the absence of the agonist.

VDR agonists include molecules that can bind to and activate the VDR, such as 1α,25(OH)$_2$-D3 and precursors and analogs thereof, VDR ligands, and VDR agonist precursors. It is not intended that the present invention be limited to particular vitamin D agonists. A variety of biologically active vitamin D agonists are contemplated. Exemplary agents are known in the art.

VDR agonists include vitamin D compounds, precursors and analogs thereof. Vitamin D compounds useful for the methods provided herein include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (e.g., compounds with a 'vitamin D nucleus' and substituted or unsubstituted A-, C-, and D-rings interconnected by a 5,7 diene double bond system typical of vitamin D together with a side chain attached to the D-ring).

Vitamin D analogs include those nonsecosteroid compounds capable of mimicking various activities of the secosteroid calcitriol. Examples of such compounds include, but are not limited to, LG190090, LG190119, LG190155, LG190176, and LG1900178 (See, Boehm et al., *Chemistry & Biology* 6:265-275, 1999).

Vitamin D compounds includes those compounds includes those vitamin D compounds and vitamin D analogs which are biologically active in vivo, or are acted upon in a mammalian subject such that the compound becomes active in vivo. Examples of such compounds include, but are not limited to: vitamin D; calcitriol, and analogs thereof [e.g., 1α-hydroxyvitamin D$_3$ (1α-OH-D$_3$), 1,25-dihydroxyvitamin D$_2$ (1,25-(OH)$_2$D$_2$), 1α-hydroxyvitamin D$_2$ (1α-OH-D$_2$), 1α,25-(OH)$_2$-16-ene-D$_3$, 1α,25-(OH)$_2$-24-oxo-16-ene-D$_3$, 1α,24R (OH)$_2$-D$_3$, 1α,25(OH)$_2$-22-oxa-D$_3$, 20-epi-22-oxa-24a,24b,-dihomo-1α,25(OH)$_2$-D$_3$, 20-epi-22-oxa-24a,26a,27a,-trihomo-1α25(OH)$_2$-D$_3$, 20-epi-22-oxa-24homo-1α,25(OH)$_2$-D$_3$, 1,25-(OH)$_2$-16,23E-diene-26-trifluoro-19-nor-D$_3$, and nonsecosteroidal vitamin D mimics.

In one example, the VDR agonist is one or more of the following vitamin D, 1,α25 dihydroxyvitamin D$_3$, 1α-hydroxyvitamin D$_3$, 1,25-dihydroxyvitamin D$_2$, 1α-hydroxyvitamin D$_2$, 1α,25-(OH)$_2$-16-ene-D$_3$, 1α,25-(OH)$_2$-24-oxo-16-ene-D$_3$, 1α,24R(OH)$_2$-D$_3$, 1α,25(OH)$_2$-22-oxa-D$_3$, 20-epi-22-oxa-24a,24b,-dihomo-1α,25(OH)$_2$-D$_3$, 20-epi-22-oxa-24a,26a,27a,-trihomo-1α25(OH)$_2$-D$_3$, 20-epi-22-oxa-24homo-1α,25(OH)$_2$-D$_3$, and 1,25-(OH)$_2$-16,23E-diene-26-trifluoro-19-nor-D$_3$. In a preferred embodiment, the biologically active vitamin D compound is selected from 1,α25-dihydroxyvitamin D$_3$, 19-nor-1,25-dihydroxyvitamin D$_2$, 19-nor-1,25-dihydroxy-21-epi-vitamin D$_3$, 1,25-dihydroxy-24-homo-22-dehydro-22E-vitamin D$_3$, and 19-nor-1, 25-dihydroxy-24-homo-22-dehydro-22E-vitamin D$_3$, and nonsecosteroidal vitamin D mimics. In an additional example, the biologically active VDR agonist is selected from the analogs represented by the following formula:

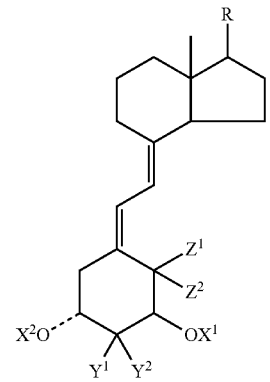

wherein $X^1$ and $X^2$ are each selected from the group consisting of hydrogen and acyl; wherein $Y^1$ and $Y^2$ can be H, or one can be O-aryl or O-alkyl while the other is hydrogen and can have a β or α. configuration, $Z^1$ and $Z^2$ are both H, or $Z^1$ and $Z^2$ taken together are CH$_2$; and wherein R is an alkyl, hydroxyalkyl or fluoroalkyl group, or R may represent the following side chain:

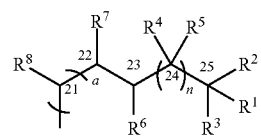

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —(CH$_2$)m- where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or CH$_3$, and wherein n is an integer having a value of from 1 to 5, and wherein the carbon at any one of positions 20, 22, or 23 in the side chain may be replaced by an O, S, or N atom.

In one example, the VDR agonists used in the methods provided herein do not cause symptoms of hypercalcemia when administered to a subject. In another example, the VDR agonists do not generate as much (i.e., a lesser degree) of a calcemic response as compared to calcitriol when administered to a subject. In one example, VDR agonists have low calcemic response characteristics as compared to calcitriol. In another embodiment, these compounds are selected from 1α,25-(OH)$_2$-24-epi-D$_2$, 1α,25-(OH)$_2$-24a-Homo-D$_3$, 1α,25-(OH)$_2$ 24a-Dihomo-D$_3$, 1α,25-(OH)$_2$-19-nor-D$_3$, and 20-epi-24-homo-1α,25-(OH)$_2$-D$_3$.

Other exemplary VDR agonists that can be used in the methods provided herein are provided in Table 1.

TABLE 1

1,25-(OH)$_2$D$_3$ and its synthetic analogs (taken from Nagpal et al., Endocr. Rev. 2005; 26: 662-687).

Vitamin D Analogs

| Compound | R | Compound | R |
| --- | --- | --- | --- |
| 1α.25-(OH)$_2$D$_3$ (Calcitriol) | | 1α.25-(OH)$_2$-22.24-diene-24a.26a.27a-trihomo-D$_3$ (EB 1089) | |
| 1α-(OH)D$_3$ (Alfacalcidol) | | 1α.25-(OH)$_2$-22-ene-25-oxa-D$_3$ (ZK 156718) | |
| 1α.24-(OH)$_2$-24-cyclopropyl-D$_3$ (Calcipotriol) | | 25-(4-methylthiazol-2-yl)-calcipotriol (ZK 191732) | |
| 1α.25-(OH)$_2$-22 oxa-D$_3$ (Maxacalcitol) | | 1α.24R—(OH)$_2$D$_3$ (Tacalcitol) | |

1α.25-(OH)$_2$D$_3$(Calcitriol)

ED-71 | 1α.25-(OH)$_2$-2β-(3-hydroxypropyl)D$_3$)

TABLE 1-continued 1,25-(OH)₂D₃ and its synthetic analogs (taken from Nagpal et al., Endocr. Rev. 2005; 26: 662-687).

"20-Epi Vitamin D Analogs"

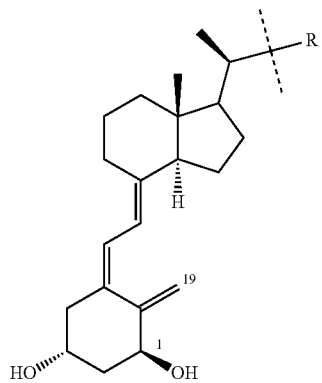

| Compound | R | Compound | R |
|---|---|---|---|
| 20-epi-22-ethoxy-23-yne-24a.26a.27a-trihomo-1α.25-(OH)₂D₃ (CB 1093) | OEt | 20-epi-1α.25-(OH)₂D₃ (KH 1060) | |
| 1α-fluoro-25-(OH)-16.23E-diene-26.27-bishomo-20epi-cholecalciferol (Ro-26-6228, BXL-628, RS-980400) | | 2-methylene-19-nor-(20S)-1α.25-(OH)₂D₃ (2MD) | |

E. Hepatic Non-Parenchymal Cells (NPCs)

As described herein, significant strides have been made to elucidate the molecular and cellular basis of fibrosis with the discovery that NPCs are involved in hepatocyte survival and that HSCs that have transdifferentiated into myofibroblasts are the key source of collagen deposition in liver.

While the liver is composed predominantly of hepatocytes, the three major NPC cell populations hepatic stellate cells (HSCs), Kupffer cells (KCs) and sinusoidal endothelial cells (SECs) impact on hepatic physiology and pathophysiology to a far greater extent than their absolute numbers would suggest, having pivotal roles in hepatic injury, fibrosis and defense from micro-organisms and toxins. It is demonstrated herein that HSCs, KC, and SECs express VDRs as well as P450 enzymes. Upon activation, for example by oxidative stress or TGFβ1, HSCs undergo a phenotypic change to myofibroblasts and secrete a range of pathological matrix components that lead to hepatic scarring (fibrosis and cirrhosis) (Bataller & Brenner 2005 *J Clin Invest.*, 115(2):209-18; Gabele et al., 2003. *Front. Biosci.*, 8:D69-D77). KCs, the resident liver macrophages, represent a significant source of chemoattractant molecules for cytotoxic CD8 and regulatory T cells. Their role in fibrosis is well established as they are one of the main sources of both TGFβ1 production and oxidative stress (via NADPH-oxidase), which leads to the transformation of HSCs into myofibroblasts (Kolios et al., 2006 *World J Gastroenterol.*, 14; 12(46):7413-20). SECs are not simply barrier cells that line the hepatic sinusoids and restrict the access of blood-borne compounds to the liver parenchyma. They are functionally specialized cells that have complex roles, including receptor-mediated clearance of endotoxin, bacteria and other compounds, in addition to regulation of inflammation, leukocyte recruitment and host immune responses to pathogens (Lalor et al., 2006 *World J Gastroenterol.*, 14; 12(34):5429-39).

F. Inflammatory Cytokines and Growth Factors Involved in Liver Fibrosis

Cytokines which regulate the inflammatory response to injury and modulate hepatic fibrogenesis, and which can be used to monitor the development, progression, or regression of fibrosis include monocyte chemotactic protein type 1 (CCL2) and RANTES (CCL5), which stimulate fibrogenesis, while IL-10 and IFNγ exert the opposite effect (Lalor et al., 2006 *World J Gastroenterol.*, 14; 12(34):5429-39; *Front. Biosci.*, 7:d1899-d1914; Safadi et al., 2004 *Gastroenterology*, 127:870-882; Sahai et al., 2004. *Am. J. Physiol. Gastrointest. Liver Physiol.*, 287:G264-G273; Yoshida et al., 2004. *J. Exp. Med.*, 199:1701-1707; Streetz et al., 2003. *Hepatology*, 38:218-229). Among growth factors, TGFβ1 is a key mediator in human fibrogenesis; it triggers the transition of HSCs to myofibroblast-like cells, stimulating the synthesis of ECM proteins that inhibit their degradation (Gressner et al., 2002. *Front. Biosci.*, 7:d793-d807). Platelet-derived growth factor (PDGF) is one of the most potent mitogens for HSCs, and is upregulated in the fibrotic liver. Cytokines with vasoactive properties also regulate liver fibrogenesis, including nitric oxide and relaxin, which exert antifibrotic effects, while vasoconstrictors like Endothelin-1, norepinephrine and angiotensin II have opposite effects (Bataller et al., 2003. *J. Clin. Invest.*, 112:1383-1394; Oben et al., 2004. *Gut.*, 53:438-445; Yu et al., 2003. *Am. J. Pathol.*, 163:1653-1662). Angiotensin II is the effector peptide of the renin-angiotensin system, which is a major regulator of arterial pressure homeostasis in humans. Key components of this system are locally expressed in chronically injured livers, and activated HSCs secrete angiotensin II. Pharmacological and/or genetic ablation of the renin-angiotensin system markedly attenuates experimental liver fibrosis (Kanno et al., 2003. *Biochem. Biophys. Res. Commun.*, 308:177-183). Angiotensin II induces hepatic inflammation and stimulates an array of fibrogenic actions in activated HSCs, including cell proliferation, cell migration, secretion of proinflammatory cytokines, and collagen synthesis (Ramalho et al., 2002. Hepatogastroenterology., 49:1499-1502; Wei et al., 2000. *World J. Gastroenterol.*, 6:824-828). Another key player in the fibrosis process is reactive oxygen species (ROS) generated by a nonphagocytic form of NADPH oxidase. These NADPH oxidases present in profibrogenic cell types are constitutively active, producing relatively low levels of ROS under basal conditions but generating higher levels of oxidants in response to cytokines, stimulating redox-sensitive intracellular pathways. NADPH oxidase also plays a key role in the inflammatory actions of Kupffer cells and disruption of active NADPH oxidase protects mice from developing severe liver injury following prolonged alcohol intake and/or bile duct ligation (Wheeler et al., 2001. *Free Radic. Biol. Med.*, 31:1544-1549; Kono et al., 2000. *J. Clin. Invest.*, 106:867-872). Metabolic cytokines derived from the adipose tissue (adipokines) like adiponectin markedly inhibit liver fibrogenesis in both in vitro and in vivo settings, while Leptin can contribute to HSC activation and fibrosis development (Yu et al., 2003. *Am. J. Pathol.*, 163: 1653-1662; Kamada et al., 2003. *Gastroenterology.*, 125: 1796-1807; Marra 2002. *Gastroenterology.*, 122:1529-1532). The actions of these cytokines in part explain why obesity can cause fibrosis and influence fibrosis development in patients with chronic hepatitis C infection.

G. NPCs and Hepatic Inflammation and Fibrosis

NPCs are central players in the inflammatory and fibrosis responses following hepatic injury. NPCs are involved in the recruitment and migration of multiple cell types, including leukocytes and neutrophils, as well the release and activation of a plethora of proinflammatory signaling cascades, including tumor necrosis factor alpha (TNFα), and interleukin 6 (IL-6; Kmiec 2001. *Adv. Anat. Embryol. Cell Biol.* 161:III-XIII, 1-151). Leukocytes recruited during injury join with KCs, the resident liver macrophages, in producing compounds that modulate HSC behavior. KCs induce inflammatory actions in the liver by producing large amounts of nitric oxide (NO) and inflammatory cytokines including TNFα, which have a direct stimulatory effect on HSC collagen synthesis (Naito et al., 2004. *Med. Electron Microsc.*, 37:16-28; Thurman 1998. *Am. J. Physiol.* 275:G605-G611). The activation of KCs coincides with the appearance of HSC activation markers involved in processes such as ECM synthesis, cell proliferation, and release of retinoids. These occur through the actions of cytokines, in particular TGFβ1 and reactive oxygen intermediates/lipid peroxides (Gressner et al., 2002. *Front. Biosci.*, 7:d793-d807). KCs also secrete the CXC chemokine interleukin 8 (IL-8), a chemoattractant and activator for neutrophils, basophils, and T cells. IL-8 secretion by KCs is complex and is regulated primarily at the transcriptional level through cooperative interactions of nuclear factor κβ (NF-κβ) and activator protein 1 (AP-1). HSCs, as well as being the major producer of ECM proteins, also display immune cell-like properties and express membrane proteins involved in antigen presentation, including members of the HLA family (HLA-I and HLA-II), lipid presentation molecules (CD1b and CD1c), and factors involved in T-cell activation (CD40 and CD80). Exposure of HSCs to proinflammatory cytokines markedly up-regulates these molecules. HSCs freshly isolated from human cirrhotic livers express high amounts of HLA-II and CD40, indicating that HSCs act as antigen-presenting cells (APCs) in human fibrogenesis (O Viñas et al., 2003. *Hepatology* 38: 919-29). Upon stimuli from an injury, SECs, which are normally fenestrated to allow rapid bidirectional transport of solutes between sinusoidal blood and parenchymal cells, rapidly lose their fenestrations and express pro-inflammatory molecules including InterCellular Adhesion Molecule-1 (ICAM-1) and Vascular Endothelial Growth Factor (VEGF); Bouwens et al., 1992. *Enzyme.*, 46(1-3):155-68; Lalor et al., 2006. *World J Gastroenterol.*, 14; 12(34):5429-39).

H. Nuclear Hormone Receptor Family

Nuclear hormone receptors (NHRs), of which there are 48 unique members in humans and 49 members in mouse, function as ligand-activated transcription factors and have roles in diverse cellular processes ranging from mammalian development and differentiation to metabolic homeostasis (Mangelsdorf et al., 1995. *Cell.*, 15; 83(6):835-9; Adams et al., 2000. *Science.*, 24; 287(5461):2185-95). NHRs bind to sequence-specific DNA response elements on target gene promoters as homodimers, heterodimers, or monomers. Structural and functional analyses of the NHR family have demonstrated that the receptors are comprised of functional modular domains. The DNA binding domain (DBD) consists of a well characterized zinc finger motif which recognizes a degenerate six to eight nucleotide sequence on the target DNA. The ligand binding domain (LBD) resides in the C-terminal portion of the protein and shares a common, predominantly alpha helical fold (Mangelsdorf et al., 1995. *Cell*, 83(6):835-9). As implied, this domain of the receptor is where cognate ligands of the receptors interact and induce conformational changes associated with transcriptional activation. Many of the known ligands for these receptors are essential metabolic products including retinoids, thyroid hormone, vitamin D3, bile acids, oxysterols, and prostenoids that act through their cognate receptors to control metabolic homeostasis in the body (Gudas 1994. *J. Biol. Chem.*, 269(22):15399-402). In addition, NHRs are also instrumental in the ability of the body to respond to and adapt to complex environmental cues.

One area of NHR function relevant to this disclosure is their role and dynamic expression profiles in response to inflammatory cues. The connections between NHRs and inflammatory responses were recently highlighted in a study profiling the 49 member nuclear receptor superfamily in bone marrow-derived mouse macrophages (Barish et al., 2005. *Mol Endocrinol.*, 19:2466-2477). 28 receptors were found to be expressed. Notably, more than half of the identified receptors occur in unique, dynamic and highly scripted temporal phases of expression upon exposure to LPS or to the prototypic Th1 cytokine, interferon gamma (Barish et al., 2005. *Mol Endocrinol.*, 19:2466-2477). These findings not only reveal that nuclear receptors are highly represented in the innate immune system but, by virtue of their dynamic expression profiles, have implications in the pathogenesis of inflammatory diseases and their therapeutic modulation.

I. Regulation of Hepatocyte Function by Nuclear Hormone Receptors

Nuclear hormone receptors play a role in controlling liver function by regulating the synthesis and metabolism of an extensive range of lipophilic molecules, many of which are cytotoxic at micromolar concentrations as exemplified by bile acids. Hepatocytes incorporate an elaborate repertoire of sensor-coupled defense mechanisms that maintain cellular integrity in the face of this hostile microenvironment. The sensors for these lipophilic molecules principally belong to the nuclear hormone receptor superfamily, particularly the subfamily that heterodimerize with the retinoid-X receptor (RXR; Handschin & Meyer 2005. *Arch Biochem Biophys.*, 433:387-96). Two nuclear hormone receptors that have emerged as key regulators in the liver for detoxification and elimination of potentially toxic xenobiotics (foreign compounds) and endobiotics (endogenous compounds) are the pregnane X receptor (PXR, NR1I2) and the Constitutive Androstane Receptor (CAR; NR1I3; Xie et al., 2001. *Proc. Natl. Acad. Sci. USA* 98:3375-80). These nuclear receptors bind to a wide variety of chemically and structurally distinct compounds and mediate the expression levels of phase I and phase II drug metabolizing enzymes including cytochrome P450 enzymes, in addition to drug transporters, as exemplified by members of the ABC transporter super family, such as MDR1 (Xie et al., 2001. *Proc Natl Acad Sci USA* 98:3375-80; Ananthanarayanan et al., 2001. *J Biol Chem.*, 276:28857-65).

Bile acids are water soluble endobiotic compounds that are amphipathic end products of cholesterol metabolism. They are generated from cholesterol in a twelve step enzymatic process that occurs exclusively in the liver, and are then secreted to the intestine as taurine or glycine conjugates in bile (Goodwin & Kliewer 2002. *Am J Physiol Gastrointest Liver Physiol.*, 282(6):G926-31). In the intestine, bacteria deconjugate and dehydroxylate bile acids to form the more toxic secondary bile acids (lithocholic acid [LCA] and deoxycholic acid [DCA]), after which they are absorbed actively from the small intestine, with each molecule undergoing multiple enterohepatic circulations back to the liver before being excreted. Bile acids are potentially hepatotoxic and are tightly controlled to prevent accumulation of concentrations that would result in liver injury and subsequent fibrosis. Three NHRs, vitamin D receptor (VDR), farnesoid X receptor (FXR) and PXR are capable of binding bile acids, heterodimerizing with RXR and then transactivating a spectrum of target genes that controls both the levels and detoxification of bile acids. FXR is the primary bile acid receptor that controls the rate of cholesterol breakdown and bile acid flux in the liver, while PXR, as mentioned above, controls the detoxification of bile acids (Goodwin & Kliewer 2002. *Am J Physiol Gastrointest Liver Physiol.*, 282(6):G926-31; Makishima et al., 2002. *Science.*, 296(5571):1313-6; Makishima et al., 1999. *Science.*, 284(5418):1362-5).

Fatty acid metabolism and transport in the liver is also tightly regulated and dysregulation can result in the accumulation of fatty acids, resulting in oxidative damage that initiates hepatic fibrosis. Fatty acid oxidation occurs in mitochondria, peroxisomes and smooth endoplasmic reticulum; mitochondria and peroxisomes oxidize fatty acids via β-oxidation while in the smooth endoplasmic reticulum the cytochrome P450 CYP4A subfamily of enzymes metabolizes fatty acids via ω-oxidation (Poirier et al., 2006. *Biochim Biophys Acta.*, 1763(12):1413-26.; Reddy & Rao 2006. *Am J Physiol Gastrointest Liver Physiol.*, 290(5):G852-8). The nuclear receptor subfamily of peroxisome proliferator-activated receptors (PPARs) act as fatty acid sensors in the liver and are integral regulators of all three sites of fatty acid oxidation as well as fatty acid transport via activation of target genes (Reddy & Rao 2006. *Am J Physiol Gastrointest Liver Physiol.*, 290(5):G852-8).

J. Nuclear Hormone Receptors and NPCs

In contrast to the extensive knowledge of NHR function in hepatocytes, prior to this disclosure, little was known of NHR function in the three major hepatic NPCs. It was unknown whether the sensor-defense mechanisms employed by NPCs are NHR-dependent. NPCs lie in close proximity to each other and to hepatocytes, and although they are central to the processes of liver inflammation, injury, and repair they are able to function within the everyday hepatic microenvironment and avoid engaging injury response genes when exposed to physiological levels of toxic and pro-inflammatory molecules. Another aspect of the NPC sensor-defense mechanism is related to the hostile hepatic microenvironment that results from the continuous exposure of liver cells to gut-derived bacterial lipopolysaccharide endotoxins (LPS), which trigger the innate immune system through binding to toll-like receptors (TLRs) (Schwabe et al., 2006. *Gastroenterology.*, 130:1886-900). Even in health, NPCs are among the first cell types that are exposed to gut-derived LPS which is constantly delivered to the liver via the portal vein; LPS increases markedly in intestinal diseases and in the presence of portal hypertension (Schwabe et al., 2006. *Gastroenterology.*, 130:1886-900).

Knowledge of NHR-mediated action in NPCs also has been limited. Fiorucci et al. (*J Pharmacol Exp Ther.*, 315(1): 58-68, 2005) have shown that primary rat HSCs in culture express FXR and that exposure of these cells to the FXR agonists 6-ethyl chenodeoxycholic acid and GW4064, results in suppression of genes associated with HSC activation, including α-smooth muscle actin, TIMP-1, TIMP-2 and α1(I) collagen. FXR was also found to be expressed in an immortalized human HSC cell line, but its function has yet to be assessed in this model (Fiorucci et al., 2005. *J Pharmacol Exp Ther.*, 315(1):58-68). Whether FXR is expressed in KCs and SECs is unknown. PXR is highly expressed in hepatic parenchymal cells but not in HSCs. Despite this, the potent rodent PXR activator pregnenolone-16α-carbonitrile (PCN) inhibits the spontaneous transdifferentiation of primary HSCs cultured on plastic to pro-fibrotic myofibroblasts (Marek et al., 2005. *Biochem J.*, 1; 387(Pt 3):601-8; Haughton et al., 2006. *Gastroenterology.*, 131(1):194-209). Whether PXR is expressed in the other NPCs has yet to be determined. Without being bound by theory, it is thought that the major role of PPARγ in HSCs is related to its regulation of fat storage similar to its essential role in adipocyte differentiation and fat storage. Activated HSCs down-regulate PPARγ expression and release fatty acids, while conversely, addition of PPARγ ligands promotes the retention of fatty acids in the HSCs and retards the trans-differentiation process. In addition to being highly expressed in non-activated HSCs, PPARγ is also expressed in KCs.

K. VDR Attenuation of Inflammatory and Fibrogenic Cascades

Inflammatory responses mediated by TLRs are part of an ancient innate immune system that elicits an immediate defensive response to a range of microbial and viral products, such as LPS. Signaling through TLRs is responsible for a wide range of biological responses. The intracellular signaling pathways through Toll/interleukin-1 receptor (IL-1R) domains result in recruitment of the cytoplasmic adaptor molecules, with subsequent activation of a signaling cascade leading to the nuclear localization of nuclear factor-kappa B (NF-kB) (reviewed in (Doyle & O'Neill 2006. *Biochem Pharmacol.*, 72(9):1102-13). In the case of LPS, efficient ligand recognition involves the signaling receptor TLR4, as well as the CD14 co-receptor and MD-2 accessory molecule. Full signal transduction involves a number of signaling adaptors, including MyD88 and the adaptors of the MyD88-independent pathway, TRAM and TRIF. HSCs express toll-like receptor 4 (TLR4) and respond to bacterial lipopolysaccharide with NF-kB-mediated pathways by secreting IL-8 and chemokines such as CCL2 (Paik et al., 2006. *Lab Invest.*, 86(7):676-86; Paik et al., 2003. *Hepatology*, 37(5):1043-55). This LPS response is specifically blocked by anti-TLR4 antibodies. As Kupffer cells are of macrophage lineage they express several TLRs, including TLR2, 4, 6 and 9 and primarily release TNF-α and IL-1 in response to LPS exposure (Su 2002. *Am. J. Physiol. Gastrointest. Liver Physiol.*, 283 G256-G265). This has been studied in relation to ethanol-induced liver injury and hepatic ischemia-reperfusion injury. SECs also express TLRs and TLR9 predominates in this cell type, binding bacterial DNA and leading to MAPK and NF-κB activation and secretion of IL-1β and IL-6 (Martin-Armas et al., 2006. *J Hepatol.*, 44(5):939-46).

VDR exerts potent anti-inflammatory actions. VDR gene expression has been found in macrophages, and is dynamically upregulated upon LPS exposure. VDR activation in human peripheral blood mononuclear cells (PBMCs) using novel VDR ligands blocked TNF-α-induced NF-κB activation and reduced PBMC proliferation (Stio et al., 2007. *J Steroid Biochem Mol Biol.*, 103(1):51-60). Additionally, fibroblasts isolated from VDR−/− mice are much more susceptible to NF-kB activation, probably due to decreased stabilization of IkBα by VDR (Szeto et al., 2007. *J Steroid Biochem Mol Biol.* 103(3-5):563-6). 1,α25-(OH)$_2$-D3 also down-regulates TLR2 and TLR4 expression in PBMCs in a dose-dependent fashion and makes these cells relatively resistant to the actions of LPS; pretreatment with the VDR antagonist ZK159222 negated this effect, showing that VDR itself is the mediator of this effect (Sadeghi et al., 2006. *Eur J Immunol.*, 36(2):361-70). Activation of VDR has been shown to down-regulate both TLR2 and TLR4 expression (Sadeghi et al., 2006. *Eur J Immunol.*, 36(2):361-70). Thus, VDR signaling is part of an anti-inflammatory pathway in hepatic NPCs.

TGFβ signaling, as discussed above, is the major pro-fibrogenic stimulator of HSCs and is initiated via growth factor interaction with a series of plasma membrane-associated receptors; the type I and type II receptors which possess intrinsic serine/threonine kinase activity (Massague & Gomis 2006. *FEBS Lett.*, 580(12):2811-20). Upon activation by the appropriate TGF ligand, the type I and type II receptors interact to form hetero-oligomers and activate intracellular signaling cascades, which in turn results in the phosphorylation and nuclear translocation of a family of conserved proteins termed Smads. These factors are unique to the TGFβ signaling pathway and regulate gene transcription and expression (Massague & Gomis 2006. *FEBS Lett.*, 22; 580(12):2811-20; Feng & Derynck 2005. *Annu Rev Cell Dev Biol.*, 21:659-93). VDR has been demonstrated to physically and functionally interact with phosphorylated SMAD3 in transcriptional assays (Feng & Derynck 2005. *Annu Rev Cell Dev Biol.*, 21:659-93), and has been postulated to modulate TGFβ signaling via competition for SMAD3. It is shown herein that TGFβ upregulates VDR expression in NPCs.

Despite the above observations, prior to the present disclosure, the role of VDR in hepatic NPCs in liver injury, inflammation, and fibrogenesis was unknown. VDR also acts as a biological sensor for LCA and its metabolites in NPCs. Portal blood is rich in recirculating secondary bile acids, which are highly hydrophobic and therefore toxic. Portal blood also contains LPS derived from intestinal bacteria even in health; this is exacerbated in the presence of intestinal diseases, portal hypertension and alcoholic hepatitis. Therefore, the cellular populations in the liver need to be tolerant to the continuous presence of low concentrations of LPS, a situation that in many other tissues would result in the activation of the innate immune system and lead to intense inflammation. Moreover, it is now clear that hepatic NPCs release a variety of chemokines and cytokines and that they use these molecules to communicate with each other as well as to recruit additional inflammatory cells.

L. Incorporation of Vitamin D receptor agonists into Pharmaceuticals

The present disclosure includes a treatment for fibrosis, for instance hepatic, renal or pancreatic fibrosis, in a subject. The method includes administering one or more vitamin D receptor agonists, such as 1α,25(OH)$_2$ D$_3$, vitamin D precursors (for instance, 25-hydroxy-D$_3$ (25-OH-D$_3$) (calcidiol); vitamin D$_3$ (cholecalciferol); or vitamin D2 (ergocalciferol)), vitamin D analogs, and vitamin D receptor agonists precursors to the subject in a pharmaceutically acceptable carrier and in an amount effective to inhibit (for example to relieve, cure, ameliorate, or prevent) the development, progression, or manifestation of fibrosis in the subject. The present disclosure also contemplates the administration of a therapeutic composition comprising more than one VDR agonist, as well as VDR agonists in combination with other therapies.

The vehicle in which the VDR agonist is delivered can include pharmaceutically acceptable compositions of the compounds, using methods well known to those with skill in the art. Any of the common carriers, such as sterile saline or glucose solution, can be utilized. The vehicle also can contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in Remington: *The Science and Practice of Pharmacy* (19th Edition, 1995) in chapter 95.

Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

In some embodiments, sustained release of the pharmaceutical preparation that includes an effective amount of a VDR agonist is beneficial. Slow-release formulations are known to those of ordinary skill in the art. By way of example, sustained-release tablets can be formulated so that the active ingredient is embedded in a matrix of insoluble substance so that the dissolving drug emerges gradually through the holes in the matrix. In some formulations, the matrix physically swells to form a gel, so that the drug has first to dissolve in matrix, then exit through the outer surface.

In one example, a preferred dose of the VDR agonist for the present methods is the maximum that a patient can tolerate and not develop serious hypercalcemia. In one embodiment, the therapeutic administration of the VDR agonist compounds only causes mild hypercalcemia. In another example, the VDR agonists do not cause symptoms of hypercalcemia.

Therapeutically effective doses of vitamin D2 and D3 range, in some embodiments, from about 50 IU to about 50,000 IU. In some embodiments, for instance, vitamin D2 and/or D3 is administered in an oral dose of, for example, less than about 75 IU, about 100 IU, about 250 IU, about 500 IU, about 750 IU, about 1,000 IU, about 1,500 IU, about 2,000 IU, about 2,500 IU, about 5,000 IU, about 7,500 IU, about 10,000 IU, about 15,000 IU, about 20,000 IU, about 25,000 IU, about 40,000 IU, or about 50,000 IU, or more. In other embodiments, calcitriol is administered in a dose of from 0.001 to 10 micrograms. For instance, calcitrol is administered, in some embodiments, in a dose of about 0.01 µg, about 0.05 µg, about 0.1 µg, about 0.25 µg, about 0.5 µg, about 1 µg, about 5 µg, or about 10 µg. In some embodiments, larger doses of VDR agonists are administered via a delivery route that targets the organ of interest, for instance the liver, kidney or pancreas. Such targeting methods are described more fully below.

In certain embodiments, the VDR agonist is administered orally, for instance, in single or divided doses. For oral administration, the compositions are, for example, provided in the form of a tablet containing 1.0 to 1000 mg of the active ingredient, such as at least 75 IU, at least 100 IU, at least 250 IU, at least 500 IU, at least 750 IU, at least 800 IU, at least 1,000 IU, at least 1,500 IU, at least 2,000 IU, at least 2,500 IU, at least 5,000 IU, at least 7,500 IU, at least 10,000 IU, at least 15,000 IU, at least 20,000 IU, at least 25,000 IU, at least 40,000 IU, or 5 at least 0,000 IU per day, for example 50 IU to 2000 IU per day, 100 IU to 1000 IU per day, such as 800 IU per day, or more of the active ingredient for the symptomatic adjustment of the dosage to the subject being treated. An effective parenteral dose could be expected to be lower, for example in the range of about 0.001 µg to about 10 µg, depending on the compound. Because the dosage and dosage regimen must be individually considered in the case of each subject according to sound professional judgment taking into account for example the age, body weight, general health, sex, diet, mode and time of administration, rate of excretion, drug combination, and severity of the condition of the host undergoing therapy, in some instances lower doses will be desirable, while in others larger doses will be required.

In another embodiment, if the VDR agonist is not a 1α-hydroxy compound, a daily dose between 1.0 and 100 µg per day per 160 pound patient is administered, such as between 5.0 and 50 µg per day per 160 pound patient. In a different embodiment, if the biologically active vitamin D compound is a 1α-hydroxy compound, a daily dose of between 0.1 and 20 µg per day per 160 pound patient is administered, while a preferred dose is between 0.5 and 10µ per day per 160 pound patient. In a particular example, the dose is between 3-10 µg per day.

In one example, the VDR agonists is cholecalciferol or calcidiol. In some examples, a higher dose than usual is administered, but with less frequency, for example, 50,000 to 500,000 units weekly.

The present disclosure also includes combinations of vitamin D receptor agonists with one or more other agents useful in the treatment of fibrosis. For example, in some embodiments, a vitamin D receptor agonist is administered in combination with effective doses of other medicinal and pharmaceutical agents. In some embodiments, one or more known anti-fibrosis drugs are included with the vitamin D receptor agonist. Specific, non-limiting examples of anti-fibrosis drugs that can be used in combination with vitamin D receptor agonists include, but are not limited to, INF-γ and the hydrophilic bile acid ursodeoxycholic acid (UDCA; for hepatic fibrosis), nuclear receptor ligands, including but not limited to Peroxisome Proliferator-Activated Receptor-gamma (PPAR-γ, NR1C3), Peroxisome Proliferator-Activated Receptor-alpha (PPAR-α, NR1C1) and Peroxisome Proliferator-Activated Receptor-delta (PPAR-Δ, NR1C2), farnesoid x receptor (FXR, NR1H4), interferon-gamma (IFN-γ), ursodeoxycholic acid (UDCA), curcumin, anti-oxidants including, but not limited to vitamin E, retinoids such as Vitamin A, and therapies that deliver proteases to the liver to degrade pathological ECM. The term "administration in combination with" refers to both concurrent and sequential administration of the active agents.

The combination therapies are not limited to the lists provided in these examples, but includes any composition for the treatment of fibrosis or conditions associated with fibrosis in a subject.

M. Routes of Administration of Vitamin D Receptor Agonists

It is not intended that the present disclosure be limited to a particular mode of administration. A variety of modes of administration are contemplated, including intravenously, intramuscularly, subcutaneously, intradermally, intraperitoneally, intrapleurally, intrathecally, orally, rectally, transdermally, by inhalation, and topically. In certain embodiments, the therapeutic compositions are administered via suppository, or in tablet or capsule formulations for oral delivery. In one embodiment, administration of the therapeutic compositions occurs at night. In another embodiment, multiple doses (e.g., 3 or 4) are provided in a 24 hour period. In a further embodiment, the administration of the therapeutic composition is by pulse intravenous therapy. In one example, the therapeutic compositions are administered via a transdermal patch (skin patch).

For instance a VDR agonist is administered, in one embodiment, intravenously in any conventional medium for intravenous injection, such as an aqueous saline medium, or in blood plasma medium. In other embodiments, administration is oral, for instance as a liquid or a pill. In other embodiments, administration is rectal, for example via a suppository containing the VDR agonist. In still other embodiments, administration is by direct infusion into a hepatic, renal, or pancreatic artery with a pharmaceutical composition that contains a vitamin D receptor agonist. In yet other embodiments, a target delivery technology is used to deliver the composition to the target tissue, for instance the liver, the kidney, or the pancreas. In one specific, non-limiting example, the vitamin D receptor agonist is designed to be taken up by the target tissue, or is linked to a target-specific carrier molecule that facilitates uptake by the target cells. For instance, for hepatic stellate cells, the vitamin D receptor agonist is conjugated to a receptor for low- and/or high-density lipoproteins (LDL and/or HDL receptors).

The present disclosure also provides a transdermal patch that includes a therapeutic composition comprising a VDR agonist. In one embodiment, the transdermal patch includes a therapeutically effective amount of a VDR agonist. In another embodiment, the transdermal patch further includes a single polymer or multiple polymers. In one example, the transdermal patch further includes a polyurethane acrylic copolymer. In one embodiment, the transdermal patch further includes silicone or polyisobutylene or both. In one embodiment, the transdermal patch is worn by a subject at risk for developing fibrosis of the liver, kidney, or pancreas. In another embodiment, the transdermal patch is worn by a subject with symptoms of fibrosis of the liver, kidney, or pancreas. In another embodiment, the transdermal patch delivers a VDR agonist to a subject in a continuous manner under conditions such that symptoms of fibrosis of the liver, kidney, or pancreas are reduced.

Pharmaceutical compositions of vitamin D receptor agonists according to the present disclosure can be administered at about the same dose throughout a treatment period, in an escalating dose regimen, or in a loading-dose regime (for instance, in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated, for instance in order to prevent or reduce the re-occurrence of hepatic, renal, or pancreatic fibrosis in a subject.

N. Assessment of Therapeutic Efficacy

Treatment of a subject with a vitamin D receptor agonist (for example in combination with other therapies) generally is conducted under the direction of a physician, and in the course of the treatment, the physician assesses the subject for evidence of relief, cure, or prevention of hepatic, renal, or pancreatic fibrosis. The evidence can be evidence of improved renal, hepatic, or pancreatic function, lessening of pain (particularly for pancreatic fibrosis), retention of renal, hepatic, or pancreatic function, or a structural change in the liver, kidney, or pancreas of the subject. For the liver, regression of fibrosis may be accompanied by reduction in size of esophageal and/or gastric varices or improvement in ascites if these clinical features were apparent prior to commencement of treatment. Thus, for example, the physician can measure one or more indicators of hepatic, renal, or pancreatic fibrosis in the subject immediately prior to, or on commencement of the treatment, and again during and after treatment. In certain embodiments, treatment is continued until evidence of relief, cure, or prevention of hepatic, renal, or pancreatic fibrosis has been achieved. In other embodiments, treatment is continued after evidence of relief, cure, or prevention of hepatic, renal, or pancreatic fibrosis has been obtained. Such treatment, in some examples, lasts for the duration of treatment of hepatic, renal, or pancreatic fibrosis in the subject, or for the lifetime of the subject.

Because the functional reserve of the liver is high, in some examples, monitoring liver function over time is not sufficient to monitor the progression of or improvement of hepatic fibrosis. In some embodiments, liver function is monitored by assessing hepatic synthetic and/or metabolic function, and/or a decrease in features of portal hypertension. One alternate method for evaluating improvement in or progression of hepatic fibrosis is to conduct one or more liver biopsies. Repeated biopsies are particularly useful for monitoring the progression of or improvement in hepatic fibrosis over time. Transient elastography (Fibroscan™) also is useful for monitoring changes in hepatic fibrosis, for instance in hepatic fibrosis due to Hepatitis C. Surrogate markers for liver fibrosis also can be monitored using blood, serum and plasma markers of liver inflammation, injury, and fibrogenesis. Such markers include but are not limited to: aspartate aminotransferase, alanine aminotransferase, gamma glutamyl transpeptidase, bilirubin, haptoglobin, tissue inhibitor of metalloproteinase-1, alpha-2 macroglobulin, hyaluronic acid, amino terminal propeptide of type III collagen and other collagen precursors and metabolites, platelet count, apolipoprotein A1, C-reactive protein and ferritin. These tests are used alone in some examples, whereas in other examples they are used in combination.

For renal fibrosis, tests of renal function generally are used to monitor improvement in or progression of renal fibrosis, for instance by estimation of creatinine clearance using the Gault-Cockcroft equation or by radionucleide imaging (for instance, using a DTPA renal scan). In many cases, plasma concentrations of creatinine, urea, and electrolytes are sufficient to determine renal function. In some instances, however, creatinine clearance is a more accurate measure of kidney function. Another prognostic marker for kidney disease is microalbuminuria, the measurement of small amounts of albumin in the urine. In other examples, the glomerular filtration rate is used to measure kidney function. For most patients, a glomerular filtration rate over 60 ml/minute is adequate, however, a significant decline in glomerular filtration rate from a previous test result indicates, in some examples, a worsening of kidney function.

For pancreatic fibrosis, tests measuring either endocrine and/or exocrine pancreatic function are useful for monitoring fibrosis, but tests of exocrine function are, in certain embodiments, more sensitive. In some embodiments, pancreatic insufficiency is diagnosed by the presence of the clinical triad of pancreatic calcification, diabetes and steatorrhea. Tests of exocrine pancreatic function include, but are not limited to CCK/secretin stimulation tests, Lundh meal tests, ERCP and pancreatic aspiration, measurement of stool fats and nitrogen or stool trypsin and chymotrypsin, and the bentiromide test and pancreolauryl test, as well as measurements of trypsinogen, lipase, or pancreatic amylase in the blood.

Other methods of diagnosing and measuring the severity of hepatic, renal, or pancreatic fibrosis are known to those skilled in the art, and it is contemplated that any one of these methods can be used to assess the efficacy of treatment of hepatic, renal, or pancreatic fibrosis.

O. Methods of Screening for Agents that can Treat Fibrosis

Some embodiments disclosed herein are methods of screening for an agent that can treat fibrosis. In general these methods include contacting a liver cell that expresses VDR, such as a stellate cell, KC, or SEC or hepatocyte contacted with TGF-$\beta_1$ and a VDR agonist (in some examples the TGF-$\beta_1$ is contacted with the cells prior to the VDR agonist, such as at least 1 hour prior, at least 6 hours prior, or at least 24 hours prior), renal mesangial cell, or a pancreatic stellate cell, with one or more test agents; and detecting production of a VDR agonist (or for example detecting expression of CYP24A1) by the cell, for example using liquid chromatography-mass spectrometry (see, for instance, Kissmeyer & Sonne (2001) *J. Chromatography*, 935:93-103; Tsugawa et al., (2005) *Anal. Chem.*, 77:3001-7) or an immunoassay such as an ELISA. Kits for carrying out vitamin D-specific ELISAs can be obtained, for instance, from Alpco Diagnostics, Salem N.H., and can be performed essentially as described in Schleithoff et al., (2006) *Am J Clin Nutr* 83(4):754-59; Zerwehk (2004) *Ann Clin Biochem* 41(Pt 4):272-81; or Armbruster et al., (2000) *Clin Lab* 46(3-4):165-66, each of which is incorporated by reference in its entirety. Any test agents that result in production of a VDR agonist, increase expression of CYP24A1 by at least 5-fold (such as at least 10- or at least 20-fold), or both, by the VDR-expressing cell are agents that can treat fibrosis.

Fibrosis also can be assessed in vivo using various biomarkers of fibrosis. In the case of hepatic fibrosis, such markers include, but are not limited to aspartate aminotransferase, alanine aminotransferase, gamma glutamyl transpeptidase, bilirubin, alpha-2 macroglobulin, haptoglobin, tissue inhibitor of metalloproteinase-1, alpha-2 macroglobulin, hyaluronic acid, amino terminal propeptide of type III collagen and other collagen precursors and metabolites, platelet count, apolipoprotein A1, C-reactive protein and ferritin. The extent of fibrosis also can be determined by a liver, kidney, or pancreas biopsy. In vitro, stellate cells can be cultured and contacted with test agents, however, in some embodiments osteoclast cell lines can be used.

In some embodiments, the methods of screening further include determining whether the VDR agonist produced by the VDR expressing liver cell or pancreatic stellate cell or renal mesangial cell can be degraded by CYP24α1, and the test agent is selected if it did not result in degradation of the vitamin D by CYP24α1. In other embodiments, the screening method further includes determining whether the test agent produces hypercalcemia effects in vitro, and the test agent is selected if it did not produce hypercalcemia effects in vitro.

EXAMPLES

Example 1

Materials and Methods

This Example provides specific materials and methods used to carry out Examples 2-4. Although particular methods are provided, one of skill in the art will appreciate that other similar methods can be used in place of those described.

A. Culturing of NPCs

Quiescent mouse HSCs were cultured on Matrigel in DMEM medium containing 4.5 g/L glucose and 16% fetal bovine serum (FBS), as previously described by George et al. (*J. Hepatol.*, 39:756-764, 2003), while isolated rat HSCs were cultured in DMEM (GIBCO) containing 20% FBS (JRH) on plastic for 40 hours. Activated HSCs were cultured on plastic rather than Matrigel in the same media described above. Kupffer cells (KCs) were cultured in Williams' medium E containing 10% FBS, 2 mM glutamine on plastic plates. Endothelial cells (SECs) were plated on type I collagen pre-coated plates in modified Medium 199 with 20% serum (10% FBS, 10% horse), insulin (4 mU/ml).

In brief, cells were obtained from mice and male Sprague-Dawley rats by in situ perfusion with pronase and collagenase and single-step Histogenz gradient as previously reported (Kristensen et al., *Hepatology* 32(2):268-77, 2000). The cell pellet was resuspended in Joklik-modified minimum essential medium, loaded onto a discontinuous gradient of arabinogalactan and centrifuged for 35 minutes at 20,000 rpm (Beckman SW-28 rotor). HSCs were collected from the top 4 layer interfaces to obtain a representative population of HSCs with different fat contents. Kupffer and sinusoidal endothelial cells from the bottom two layer interfaces were separated by continuous centrifugal elutriation using a Beckman J-6M/E centrifuge with a JE 5.0 rotor. To confirm the identity of each cell type, an aliquot was cultured for 48 hours. HSCs are identified by their autofluorescence (purity typically >98%), Kupffer cells by latex bead phagocytosis (purity typically >95%), and endothelial cells by their cobblestone morphology (purity typically >90%) and presence of fenestrae by electron microscopy. The remainder of each cell pellet was resuspended in TRIzol reagent or snap frozen and stored at −70° C. for later mRNA analysis. Whole liver tissue was isolated from rats.

The rat or mouse HSCs were cultured in the appropriate medium as described above for 40 hours, the medium removed, and fresh medium without FBS or FCS but in the presence or absence of LPS (15 ng/ml) or TGF-β1 (2 ng/ml) and/or various concentrations (as indicated in figures) of plain vitamin D (cholecalciferol) or 25(OH) vitamin $D_3$ (calcidiol) or 1α,25(OH)$_2$ vitamin $D_3$ (calcitriol) were added to the cells for 24 hours.

Human LX-2 cells were grown to 50% confluence in DMEM with 10% FBS in 6-Well plates. This medium was removed and fresh medium without FBS but in the presence or absence of various concentrations of plain vitamin D (cholecalciferol) or 25(OH) vitamin $D_3$ (calcidiol) or 1α,25 (OH)$_2$ vitamin $D_3$ (calcitriol) was added to the cells for 24 hours. LX-2 cells express VDR message and protein, are VDR responsive in terms of target gene induction (CYP24A1), and thus appear an ideal model. An added benefit of employing this clonal cell line is that stable lines over-expressing dominant-negative and constitutively-active forms of VDR are generated, facilitating the functional characterization of VDR in HSCs.

B. Reverse Transcriptase PCR

Total RNA obtained from rodent-isolated NPCs and whole liver were processed in two steps. To ensure the efficient amplification of all RNAs in a sample, random hexamer primers were used to generate cDNA, which was then analyzed via QPCR as described below.

For a typical assay, 4 μg of total RNA was treated with a 1:5 dilution of RNase-free DNase Ito remove contaminating genomic DNA. This reaction was performed in a final volume of 20 μl in 0.2 ml thin-walled PCR tubes in a standard thermocycler in the presence of 4.2 mM $MgCl_2$. The reaction proceeded for 30 minutes at 37° C., the enzyme was deactivated at 75° C. for 10 minutes, and the reaction was then brought to a 4° C. hold. The reverse-transcription mix consisting of 1× First Strand Buffer, 10 mM DTT, 200 U of SuperScript RT II reverse transcriptase, 2 mM dNTPs and 0.08 μg/μl random hexamers was then added directly to the tubes with the DNase-treated RNA for a final volume of 100 μl. The cDNA synthesis was carried out in the thermocycler at 25° C. for 10 minutes, 42° C. for 50 minutes, 72° C. for 10 minutes, and 4° C. hold. Following the reverse-transcription, DEPC-treated $H_2O$ was added to the samples to bring the volume to 200 μl, and the cDNA concentration to 20 ng/μl. (Samples used for cDNA standards were not diluted prior to making the 5-fold dilution series used in primer validation and standard curve assays.) This protocol results in enough template cDNA to test approximately 40 QPCR targets.

C. QPCR SYBR® Green I or TaqMan®-Based Assays

The HT-QPCR profiling was performed using the fluorescence monitoring chemistry of SYBR® Green and TaqMan®.

SYBR® Green I is a DNA-intercalating dye used as a reported fluorophore. The QPCR instrumentation continuously records the increase in fluorescence due to SYBR® Green I binding the double-stranded DNA generated by the PCR amplification. This assay requires only a validated primer pair in addition to the regular PCR components (Wittwer et al., 1997. *Biotechniques.*, 22(1):130-138).

The TaqMan® chemistry utilizes FRET (fluorescence resonance energy transfer) technology. It uses a specialized conjugated primer, referred to as a probe, which has been labeled on its 5' end with a fluorescent reporter dye and on its 3' end with a fluorescence quencher. While the probe is intact, the 5' and the 3' dyes are sufficiently close that the fluorescent signal is quenched via FRET. During each cycle of PCR, any probe which has annealed to the designated sequence between the forward and reverse primers is cleaved by the nuclease activity of the Taq polymerase to release the 5' reporter dye. Once cleaved, the 5' reporter is no longer efficiently quenched and continuously fluoresces. As one probe is cleaved for every PCR product made during the reaction, the increase in fluorescence during the assay can be correlated with the level of transcript in the sample. TaqMan® offers an added layer of specificity in addition to the forward and reverse primers, as the probe sequence must exactly match the target sequence. A single nucleotide difference in the probe sequence will prevent the cleavage event necessary to generate a reporter signal, thus increasing the stringency of the assay (Giulietti et al., 2001. *Methods.*, 25(4):386-401).

D. Design and Validation of QPCR Primer Sets

QPCR assays rely on a set of universal cycling conditions however, the QPCR primer sets necessarily vary between samples. Thus, the design and the pre-validation of each primer set is important to generate reliable data. First, the nucleotide sequence and the mRNA exon structure for each gene of interest was obtained from the NCBI Locus Link database. For both SYBR® Green and TaqMan®-based assays, Primer Express™ Software (Applied Biosystems) was used to design the TaqMan®MGB Probe and Primer sets. The software returns a list of primer and probe sequences as matched primer/probe sets, and primers are chosen based on their binding sites. In order to distinguish amplification of mRNA from genomic DNA, the PCR product, or amplicon, preferably spans an intron junction between two exons. When using TaqMan®, ideally the probe should sit across the junction. Minimally, each primer should sit in completely separate exons. The amplicon length should be a minimum of about 50 base-pairs and a maximum of about 150 base-pairs. Once the primers were chosen, a general BLAST of each primer sequence was run to ensure their unique specificity. Oligonucleotides were purchased from a commercial vendor at the small-scale synthesis with minimum purification. To validate the primers, a template titration assay was done. For human transcripts, the Universal Reference Total RNA from BD Clontech (Palo Alto, Calif.) was employed, while for mouse transcripts; Universal Reference Total RNA from Stratagene was employed. The assay consists of a 5-fold dilution series of cDNA reverse-transcribed from the universal RNA (50 ng, 10 ng, 2 ng, 0.4 ng, 0.08 ng, 0.016 ng), and two control samples: a no template control (NTC), and a no reverse transcriptase (−RT) control. Amplification of the NTC sample indicates the presence of primer-dimers formed during the reaction. The −RT sample is included to confirm the absence of genomic amplification. A valid primer set should have a slope of −3.3 and a correlation coefficient (R2-value)>0.95 for the standard curve. In addition, the dissociation curve should appear as a single "stacked" peak at the amplicon Tm determined by the Primer Express™ software (Bookout & Mangelsdorf 2003. *Nucl Recept Signal.*, 23).

For qRT-PCR, 500 ng of deoxyribonuclease-treated total RNA was reverse transcribed into cDNA using SuperScript™ III reverse transcriptase essentially as described by the manufacturer (Invitrogen). Quantification of gene of interest mRNA was performed using a Rotor-Gene, RG 6000 (Corbett Research). The following primer pairs were used for the amplification of gene of interest: ratCYP27b1 forward 5'-ggctcctatgcccacctc-3' (SEQ ID NO: 1); ratCYP27b1 reverse 5'-cacagcctttagcaggggta-3' (SEQ ID NO: 2); ratCYP24a1 forward 5'-agatcaaaccttggaaagccta-3' (SEQ ID NO: 3); ratCYP24a1 reverse 5'-gccactcctgtccttccag-3' (SEQ ID NO: 4); ratCYP27a1 forward 5'-ttccagctatttctacgaggctat-3' (SEQ ID NO: 5); ratCYP27a1 reverse 5'-ccgtacttggccttgt-tca-3' (SEQ ID NO: 6); human CYP24a1 forward 5'-catcatg-gccatcaaaacaat-3' (SEQ ID NO: 7); human CYP24a1 reverse 5'-gcagctcgactggagtgac-3' (SEQ ID NO: 8); human CYP27a1 forward 5'-ctcatggctggagtggaca-3' (SEQ ID NO: 9); human CYP27a1 reverse 5'-acacccaccacttcctcgt-3' (SEQ ID NO: 10); human CYP27b1 forward 5'-cttgcggactgctcactg-3' (SEQ ID NO: 11); human CYP27b1 reverse 5'-cgcagactacgttgt-tcagg-3' (SEQ ID NO: 12). For standardization, rat Sp1 or human beta 2 microglobulin (B2M) were amplified using the following primers: rat Sp1 forward 5'-gctatagcaaacac-cccaggt-3' (SEQ ID NO: 13); rat Sp1 reverse 5'-gatcagggct-gttctctcctt-3' (SEQ ID NO: 14). Human B2M primers were from Applied Biosystems.

E. Liquid Handling Robotics and Thermal Cycler (384 Well)

Accurate high throughput (384 well-format) QPCR is made possible through the use of a liquid handling robotic core. The HT-QPCR utilizes an eight-channel liquid handling robot, a Perkin Elmer Multiprobe II, which is routinely used to accurately dispense small volumes. The QPCR assay is run in a 384-well Optical Reaction Plate with 10 µl final volume per well. Each sample is run in triplicate for each gene to be assayed. Through use of the liquid handler, rapid accurate dispensing of the QPCR buffers, sample and primers can be achieved in an automated fashion decreasing the amount of user-introduced variation by ensuring a homogeneous mix. The plate is then covered with an optical adhesive cover and centrifuged to bring the liquid to the bottom of the wells of the plate prior to analysis in the QPCR machine.

Two Applied Biosystems QPCR instruments (7900HT, ABI, Foster City, Calif.) were used that enable high-throughput capacity. The 7900HT is a rapid cycling instrument with a single run lasting approximately two hours. The instrument is compatible with the use of either 96-well or 384-well formats. The protocols employed by the core use the 384-well format. The instruments have a robotic plate loader arm installed which enables unattended operation allowing the analysis of up to 24 plates per day.

F. Analysis of Data

The completed QPCR plate run was analyzed using the ABI 7900HT instrument software, SDS2.1, which plots a standard curve and a dissociation curve for each target gene. Data analysis was then performed either by the standard curve or the comparative Ct (or ΔΔCt) methods. Briefly, the standard curve method is as follows. The instrument software calculates the quantity of transcript in each unknown sample based on the linear regression formula of the standard curve, and data are exported as a tab-delimited text file. Further data analyses are done using Microsoft Excel, or another comparable program. For each sample, the quantity of the gene of interest (GOI) and the reference gene (reference) are determined in triplicate, and from these values, the average transcript quantity (avg), the standard deviation of the average (stdev), and the coefficient of variation (CV) of the average is determined, given by the formula CV=(stdev/avg). To determine the mRNA level in each sample, the gene of interest is normalized to the reference gene, (36B4 or 18S rRNA), to account for cDNA loading differences and calculated as normalized value=(GOI qty avg)/reference qty avg). The resulting normalized values are plotted as a bar graph±the standard deviation.

The comparative Ct, or ΔΔCt method uses the average cycle time (Ct), the stdev, and the CV of each sample. The average Ct of the GOI is normalized to the average Ct of the reference gene for the same sample to calculate the normalized ΔCt for the GOI. A calibrator or control is then chosen from the samples, to which the others will be compared. For example, in an experiment in which wild-type mice are compared to knockout mice, the calibrator would be the wild-type mouse sample. The ΔΔCT, or calibrated value, for each sample is calculated by subtracting the calibrator ΔCt from the sample ΔCt. The fold-induction for each sample is relative to the calibrator. The resulting induction values are usually plotted as a bar graph. If there are multiple samples in multiple treatment groups, the average fold induction for each group is plotted.

G. Western Blotting

Day 0 or day 3 HSCs were dissolved in whole cell extraction buffer [25 mM Tris-Cl, pH 8.0, 10% (w/v) glycerol, 2 mM EDTA, 0.2 mM dithiothreitol (DTT), 1% Triton X-100, 1.5 mM $MgCl_2$ and 200 mM NaCl)] and lysed on ice for 1 h, then centrifuged at 14,000 rpm for 15 min, 4° C. 20 µg of solubilized HSC extracts were analyzed on 10% SDS-PAGE gels. Gels were electroblotted onto Hybond-P Extra nitrocellulose membrane (Amersham Biosciences) and blocked for 4 h, 22° C. with PBS containing 5% skim milk powder. To check for equal protein loading/transfer, the membrane was stained with Ponceau S solution (Sigma). After removing the stain by washing in water, the membrane was probed with a monoclonal rat anti-VDR antibody (1/250; Chemicon) in PBS overnight at 4° C., followed by anti-mouse peroxidase-conjugate (1/10,000; Sigma) for 1 h at 22° C. Immunoreactive band was detected by chemiluminescence (Lumi-Light$^{PLUS}$; Roche Diagnostics).

H. Immunocytochemistry

HSCs or LX-2 cells grown in chamber slides with or without treatment were fixed in 2% buffered paraformaldehyde for 10 min at 4° C., washed in ice cold TBS containing 0.2% Tween-20 (TBST), and blocked with 10% donkey serum in TBST for 30 min at 22° C. Slides were incubated with anti-VDR (1:50) antibody in TBST containing 10% donkey serum overnight at 4° C., followed by anti-mouse IgG conjugated to ALEXA (1/1000; Molecular probes) for 1 hour at 22° C. As a control, slides were probed as described above, but in the absence of primary antibodies. For DAPI staining, slides blocked with serum were exposed to DAPI (Sigma) (1:5000) for three minutes at room temperature. Slides were washed in TBS and mounted using mounting medium and visualized with a fluorescence microscope.

I. Gene Expression Analysis Using Illumina Oligonucleotide Bead Arrays

Total RNA from control HSCs and 24 h LPS- or TGF-β1-activated and/or various concentrations (as indicated in figures) of plain vitamin D (cholecalciferol) or 25(OH) vitamin $D_3$ (calcidiol) or 1α,25(OH)$_2$ vitamin $D_3$ (calcitriol) treated HSCs were extracted using the RNeasy kit (Qiagen, Valencia, Calif.) according to the manufactures instructions. A260/280 ratios were >2.0 on a NanoDrop ND-1000 spetrophotometer and the integrity of the total RNA was verified on a Bioanalyzer (Agilent technologies).

For Illumina microarray analysis, Illumina TotalPrep RNA Amplification Kit (Ambion; Catalog # IL1791) was used with the manufacturer's instructions for the RNA amplification. The results obtained are equivalent to those achieved with qPCR. Essentially, biotinylated cRNA was prepared according to the manufacturer's directions starting with 200 ng total RNA. Hybridization to the Illumina Sentrix RatRef-12 v.1 and Mouse RefSeq version 2 Expression BeadChips (Illumina, Inc., San Diego, Calif.), washing and scanning were performed according to the Illumina BeadStation 500× manual (revision C). As the naming implies, there is complete expression coverage of the entire NCBI reference sequence gene set. RNA is isolated using Trizol and the quality/integrity of the total RNA verified using a Bioanalyzer (Agilent). This kit is a complete system for generating biotinylated, amplified RNA for hybridization.

Microarray experiments were repeated two times with RNA from two experiments where HSCs were isolated from two different rats and for each condition triplicate samples were used. The "Detection Score" was used to determine expression using the Illumina platform. It is a statistical measure in the BeadStudio software (version 1.5.0.34), which is computed based on the Z-value of a gene relative to the Z-value of the negative controls. The Illumina data were adjusted ("normalized") using a cubic spline function. Genes differentially expressed in LPS- or TGF-β1-activated and/or 1α,25 (OH)$_2$ vitamin $D_3$ (calcitriol) treated HSC samples were identified using the Illumina custom error model implemented in BeadStudio. The expression difference score, Diff-Score, takes into account background noise and sample variability. BeadStudio software allow comparison of nearly 23,000 genes between control and treated HSCs (n=2×3). Illumina expression arrays utilize gene-specific 50-mer oligonucleotide probes with an average of 30 replicates of each probe bead per individual array. This provides a high degree of confidence for the estimation of each genes abundance, as 30-fold technical replication is many times that of other methodologies for measuring gene abundance such as real-time PCR.

J. Cytokine/Chemokines Protein Profiling.

1. Luminex Bio-Plex Technology Base

Briefly, the Luminex Bio-Plex workstation was built on proven technology incorporating flow cytometry, microspheres, lasers, digital signal processing and traditional chemistry to accurately measure multiple protein levels of interest in a single sample. The Luminex technology uses color-coded tiny beads, called microspheres, that can be divided into 100 distinct sets. Each bead set can be coated with an antibody specific to a particular protein; allowing the capture and detection of specific analytes from a sample. Within the Luminex compact analyzer, lasers excite the internal dyes that identify each microsphere particle, and also any reporter dye captured during the assay. Multiple readings are made on each bead set, allowing robust validation of the results. In this way, Luminex technology allows rapid and precise multiplexing of up to 100 unique assays within a single sample. The Luminex technology is formatted on a microplate platform that allows the automated analysis of 96-well plates, enabling a throughput of more than 1,800 assay points (19-Plex assays) in 30 minutes. This system has several advantages over traditional ELISA techniques including the reduction of consumable and labor costs, and increasing the number of assays that can be performed in volume-limited samples such as mouse serum, shortening the time to results.

2. Data Analysis

The Bio-Plex workstation comes with a statistical analysis package that allows accurate standard curve analysis (4PL and 5PL StatLIA software from Brendan Scientific). In addition, data reduction for both quantitative and qualitative analysis can also be performed. The report table generated by the software also provides detailed statistical analysis including % CV and standard deviation and is readily exportable to a Microsoft excel worksheet format for data manipulation and graphing.

K. Feasibility Assessment

To assess the usefulness of Luminex Bio-Plex system as a rapid, accurate exploratory mechanism for cytokine protein expression profiling, serum from mice pre-treated with a PPAR delta ligand were examined following an inflammatory challenge using a commercially available Biorad 18-Plex assay kit. Briefly, wild type C57B6 mice were injected intraperitoneally (IP) for two days with either GW1516 (a PPAR delta ligand used at 5 mg/kg/d) or vehicle (DMSO in 1% carboxymethylcellulose). The mice were then either injected IP with $1.6 \times 10^8$ cfu of *E. coli* or saline to induce an acute inflammatory response. Serum was obtained 8 hours after infection and then assayed using the Luminex Bio-Plex technology with subsequent analysis using StatLIA software (Brendan Scientific). The results from this pilot study were plotted on a logarithmic scale to emphasize the ability of the Luminex Bio-Plex technology to accurately measure 18 cytokines simultaneously across 5 orders of magnitude (IL-4 levels of 10 pg/ml as wells as KC levels of $1 \times 10^6$ pg/ml). This data demonstrates that the use Luminex Bio-Plex technology permits rapid analysis of profile samples for cytokine levels.

Example 2

Comparative Profiling of NPC Cell Populations

This Example describes a comprehensive profiling of NHR expression in freshly isolated primary HSCs.

Figure 1B:
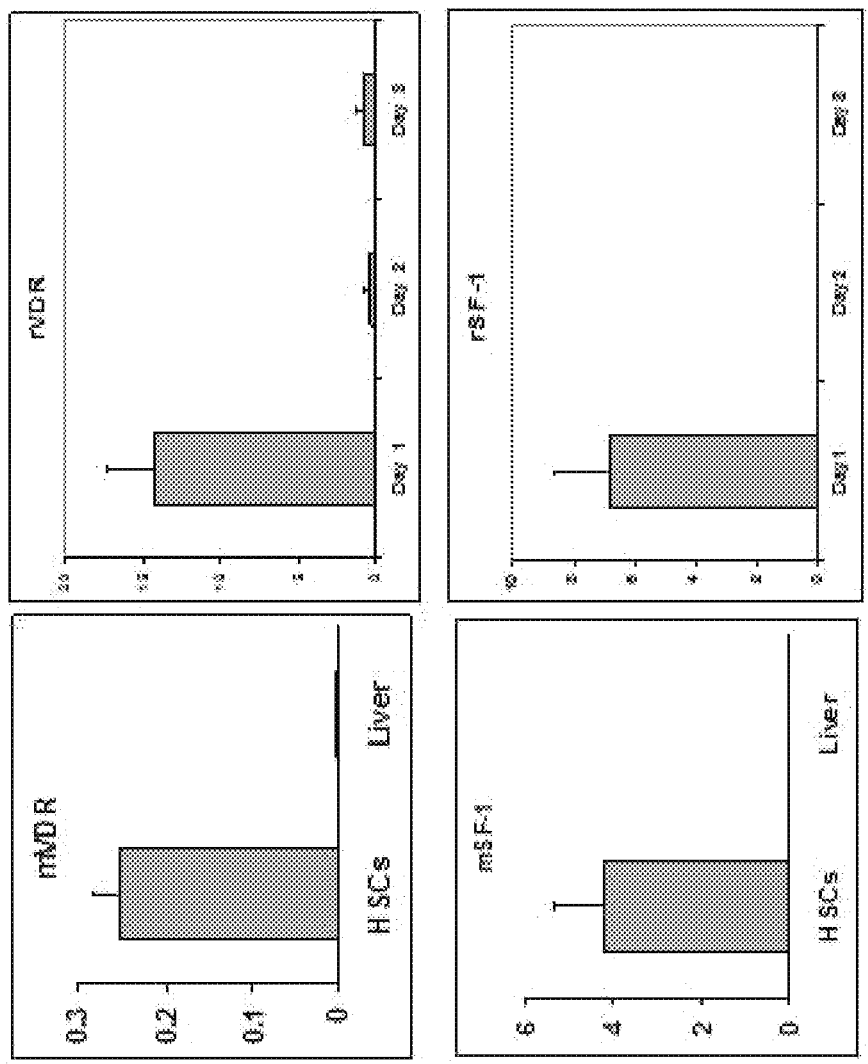
FIG. 1B shows a quantitative comparison of VDR and SF-1 expression. The left panels show the expression of mVDR and mSF-1 in murine liver and primary isolated HSCs, and the right panels show the decrease in expression of rat VDR and SF-1 in primary HSCs observed after 1, 2 and 8 days in culture (normalized to the ribosomal 36B4 expression).

The NHRs are well characterized transcription factors whose activities are modulated by physiological ligands. Obtaining a complete profile of the NHR family in a given cell therefore provides a highly informative snapshot of a cell's function. This knowledge, in turn, allows the identification of small molecule chemical tools with which to manipulate a cell's function. Thus, a comprehensive profiling of NHR expression in freshly isolated primary HSCs from wild type C57B6 mice was performed and these results were compared with those from whole liver. HSCs cells were isolated as described in Example 1. High throughput quantitative PCR identified 36 nuclear receptors expressed in mouse HSCs compared with 39 nuclear receptors in liver (FIGS. 1A and 1B); receptors were deemed expressed if transcripts were detected in less than 35 cycles (Ct<35) using an extensively validated primer set and Cyber green detection. Similar results were obtained with primary rat HSC and with the LX-2 human HSC cell line.

Although extensive overlap in expression patterns was observed, some surprising differences were detected between freshly isolated HSCs and whole liver. In particular, VDR was highly expressed in HSCs but not detected in whole liver, where 95% of the cells are hepatocytes. In addition, the NHR SF-1, a known competence factor for steroidogenesis, was expressed in HSCs but not detected in whole liver. Furthermore, based on this result, it was confirmed that primary HSCs also express SF-1 dependent steroid-producing cytochrome P450 genes (CYP11α1, CYP21α1); the expression of SF-1 and SF-1 dependent genes were rapidly down-regulated within days of cell isolation. These data demonstrate the power of high throughput QPCR for identifying NHR expression in minority cell populations like NPCs within the liver.

Profiling of the ABC gene family of xenobiotic and endobiotic transporters and members of the solute carrier superfamily indicated that primary HSCs express primarily export pumps and relatively few import pumps, compared to whole liver (Table 2). This indicates that these cells function like endocrine cells, preferentially excreting signals into the sinusoidal space.

TABLE 2

Expression in primary HSC cells

| Transporter | Substrate | Expression Level HSC | Expression Level Liver |
|---|---|---|---|
| Export Pump | | | |
| ABCA1 | Cholesterol efflux | Medium | Medium |
| ABCG1 | Cholesterol efflux | Low | Medium |
| ABCG4 | Cholesterol efflux | High | No expression |
| MDR1a | Xenobiotic Drug efflux | High | Medium |
| MDR1b | Xenobiotic Drug efflux | High | No expression |
| MRP-1 | Steroid hormones, Xenobotic drugs, and bile salts | High | Medium |
| MRP-2 | Cyclic nucleotides and some nucleoside monophosphate analogs | No Expression | High |
| MRP-3 | Organic anions including bile salts | Low | High |
| MRP-4 | Bile acid efflux | High | Medium |
| MRP-6 | Small peptides | No Expression | High |
| MRP-7 | Estradiol(2)17beta glucuronide | Medium | Medium |
| Uptake Pump | | | |
| BSEP | Bile Acid Uptake | No Expression | High |
| OATP4 | Uptake of bile acids and other organic anions | No Expression | High |
| OATP-C | Uptake of bile salts and bilirubin | No Expression | High |
| OATP-2 | Uptake of bilirubin | No Expression | High |
| NCTP | Uptake of bile salts | No Expression | High |

Figure 2D:
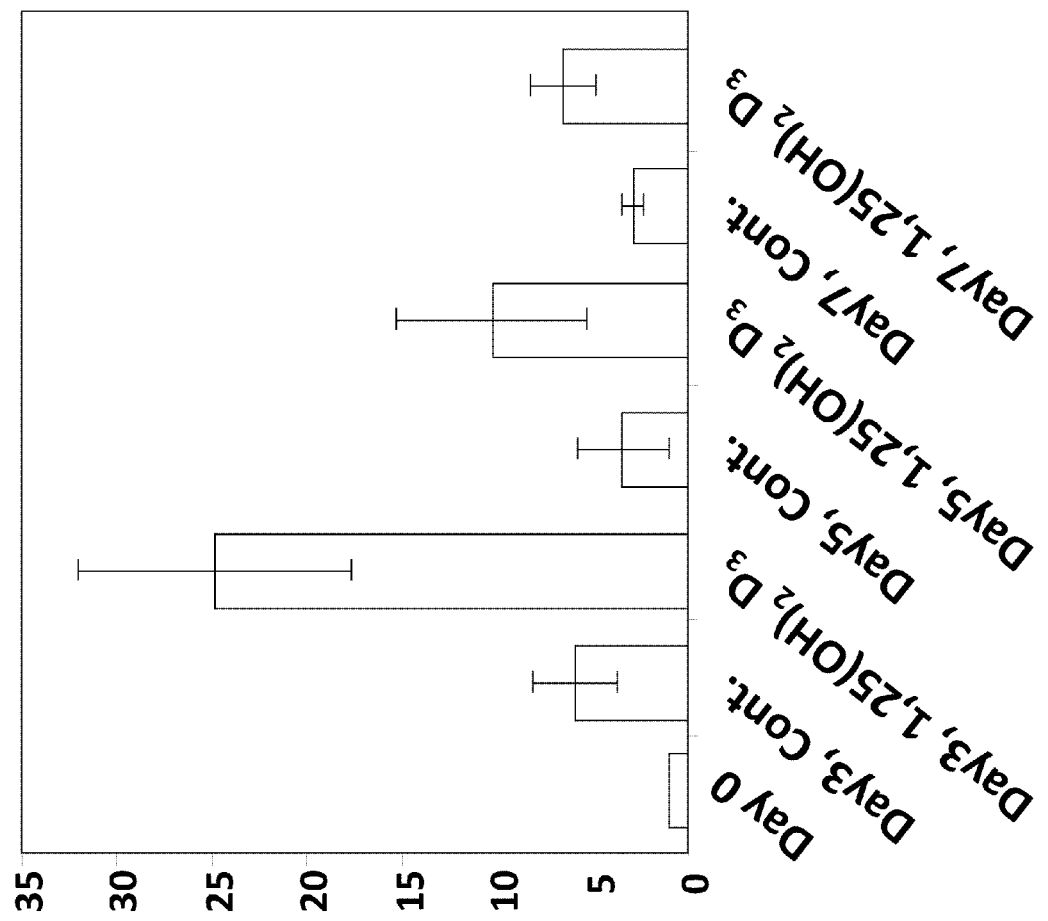
FIG. 2D is a bar graph showing VDR expression in HSCs after treatment with 1α,25(OH)$_2$D3.

Freshly isolated primary HSCs are considered quiescent, but are known to trans-differentiate to myofibroblasts when cultured on plastic and to produce fibrogenic markers. Western blotting and immunofluorescent staining confirmed the QPCR expression data that HSCs synthesize the VDR protein. VDR expression at the protein level in rat HSC was confirmed by a western immunoblot analysis using a VDR-specific monoclonal antibody and it showed that VDR (55 kDa) is present in day 3 hepatic stellate cells (FIG. 2A). This antibody when used in rat HSCs and LX-2 cells to localize the protein by immunocytochemistry found the VDR in both the cytoplasm and nucleus (FIGS. 2B and 2C). In addition, VDR was observed to translocate to the nucleus upon treatment with either $1\alpha,25(OH)_2$ vitamin $D_3$ or a secondary bile acid lithicolic acid (LCA), indicating that the expressed receptor is functionally active in these cells (FIGS. 2B and C). VDR expression in HSCs was further confirmed by real-time qPCR analysis (FIG. 2D) which show receptor level increased with $1\alpha,25(OH)2$ vitamin D3 but decreases gradually over time in culture.

VDR expression was followed during continuous passaging of primary rat HSCs and a significant down-regulation was observed, although VDR message and protein were still detected after 8 days in culture, indicating that VDR expression plays a role in maintaining the quiescent nature of these cells.

Example 3

Cytochrome P450 Gene Expression and Regulation in HSC

This example demonstrates that rodent and human HSC cells express cytochrome P450 genes required to synthesize the active VDR ligand, $1\alpha,25(OH)_2D3$ (calcitriol), from vitamin D precursor, and that such gene expression can be regulated.

Figure 3:
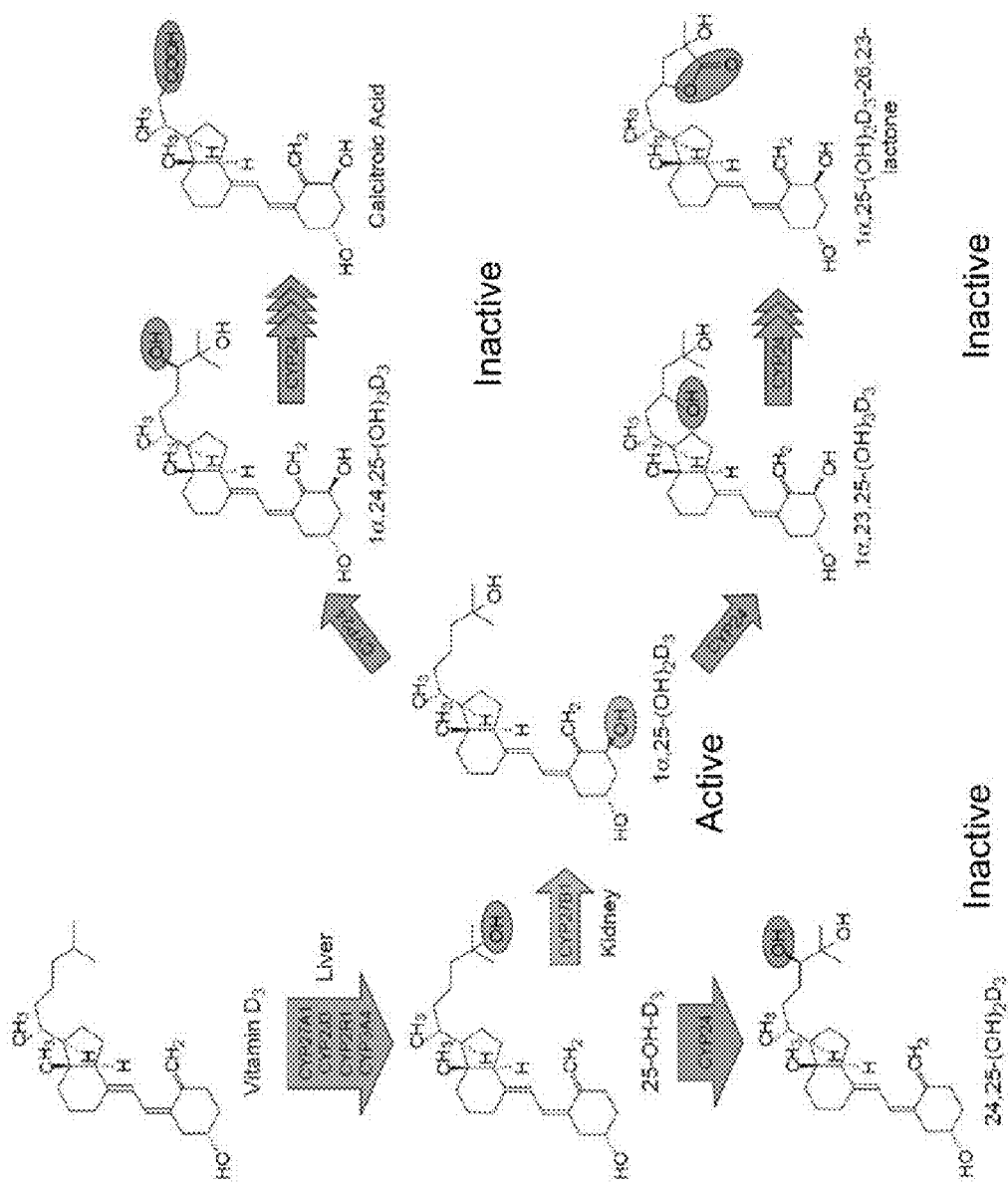
FIG. 3 is a schematic drawing showing the identified cytochrome P450 genes in HSCs involved in the synthesis of the active VDR agonist 1α,25(OH)$_2$D3 (calcitriol) from the nonactive precursors vitamin D3 (cholecalciferol) and 25-OH vitamin $D_3$ (calcidiol). CYP24A1 is the major enzyme responsible for deactivation of $1\alpha,25(OH)_2D3$ through 24-hydroxylation.
Figure 4A:
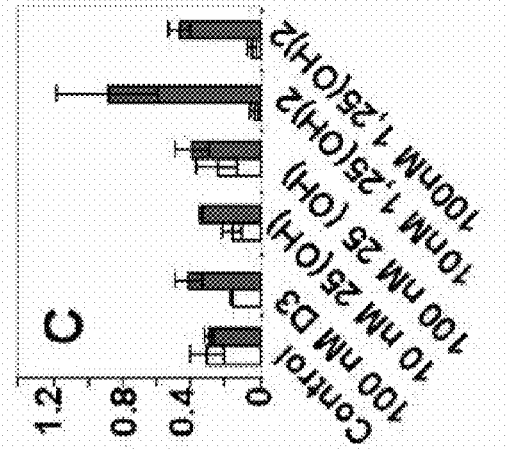
FIGS. 4A-C are bar graphs showing the impact of $1\alpha,25(OH)_2D3$ and vitamin D precursors on Cyp27a1 and Cyp27b1 expression in quiescent and activated primary rat HSCs in culture on plastic. (A) Quiescent HSCs, which had been maintained in culture on plastic for 40 hours, were treated for 24 hours with vitamin D precursors cholecalciferol (vitamin D3) or calcidiol (25-OH vitamin D3). (B) HSCs cultured as above were treated for 24 hours with 25-OH vitamin D3 or $1\alpha,25(OH)_2$ vitamin D3. (C) HSCs activated by culture on plastic for 7 days were treated with different concentrations of vitamin D3, 25-OH vitamin D3 or $1\alpha,25(OH)_2$ vitamin D3 for 24 h. In all experiments expression levels of Cyp27a1 and Cyp27b1 mRNA were determined by quantitative real time PCR (qPCR).
Figure 4B:
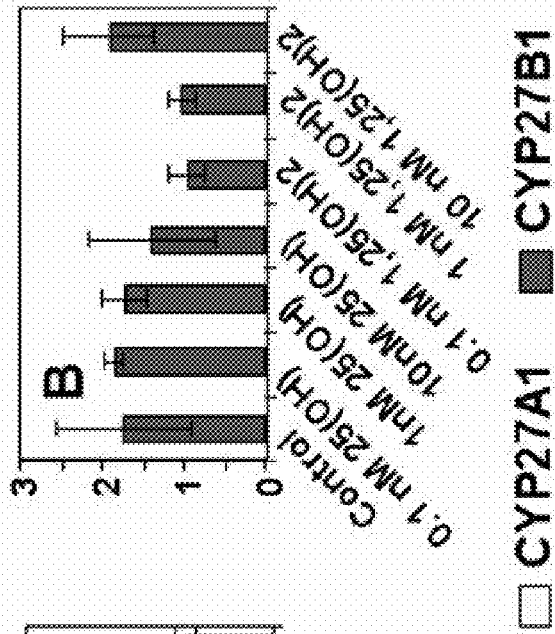
Figure 4C:
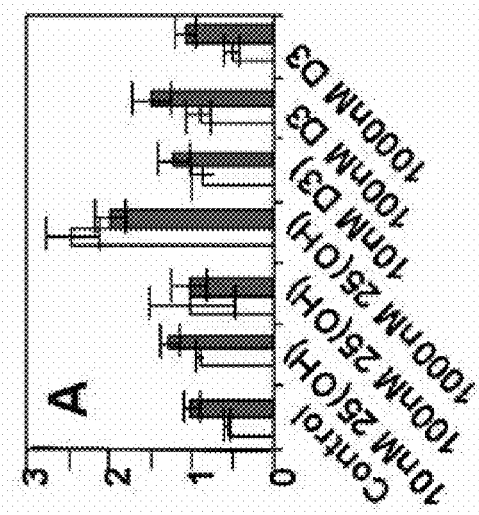

High throughput gene profiling of the cytochrome P450 gene family was used to analyzed rodent HSC cells and human LX-2 cells. Necessary cytochrome P450 genes (including CYP27A1, CYP27B1, CYP24A1) required to synthesize the active VDR ligand, $1\alpha,25(OH)_2D3$ (calcitriol), from vitamin D precursors (FIG. 3) were detected in both primary HSCs and the LX-2 cell line (FIGS. 4A-C). Microarray data on rat HSC where a comparison of control against LPS-activated cells showed several differentially expressed genes. Among them CYP27A1 was also up-regulated more than 7-fold upon LPS treatment and CYP27A1 expression in HSCs was further validated by real-time qPCR (FIGS. 4A and 4C). Real-time qPCR data (FIGS. 4A-B) demonstrate the expression of CYP27B1 in HSCs. Therefore, because VDR, CYP27A1, and CYP27B1 are expressed in HSCs, these cells have the capability to synthesis active vitamin D metabolite, $1\alpha,25(OH)_2$ vitamin $D_3$, from 25(OH) vitamin $D_3$. Expression of both CY27A1 and 27B1 are relatively unaffected by any of the treatments. However a significant reduction in the level of expression of these enzymes in the self activated day 7 HSC was observed (FIG. 4C). In the LX-2 cell line, only the expression of CYP27A1 but not the CYP27B1 in day 7 culture was reduced with self activation (FIG. 4B).

Figures 6A, 6B:
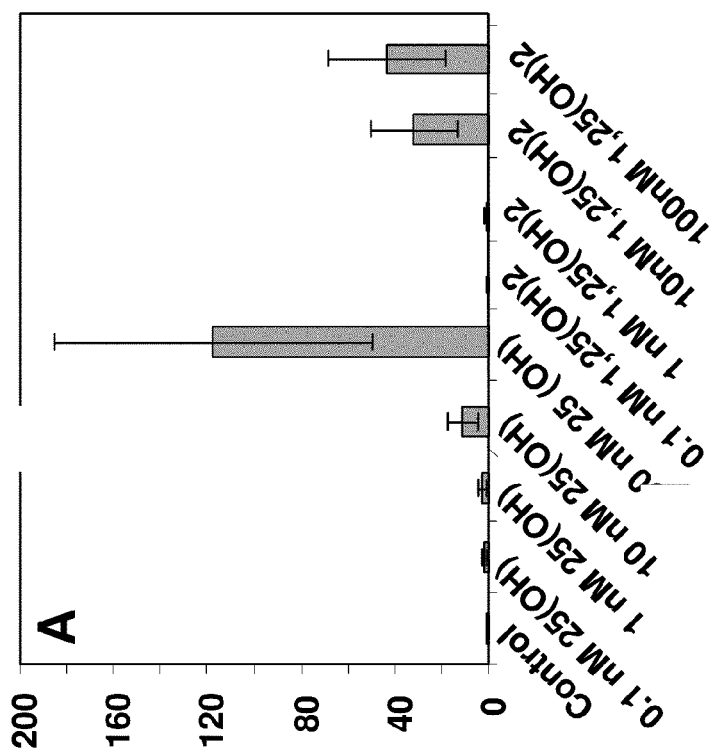
FIGS. 6A-B are bar graphs showing CYP24A1 gene expression in the human LX-2 cell line. (A) LX-2 cells grown on culture plates for 2 days or (B) 7 days were treated with different concentrations of vitamin $D_3$ (cholecalciferol) or 25(OH) vitamin $D_3$ (calcidiol) or $1\alpha,25(OH)_2$ vitamin $D_3$ (calcitriol) for 24 hours and expression levels of CYP24A1 gene were determined by quantitative real time PCR (qPCR).

Enhanced expression of CYP24A1 was observed in quiescent HSCs as well as in day 2 LX-2 cells after treatment with $1\alpha,25(OH)_2$ vitamin $D_3$ (FIGS. 5 and 6). With the knowledge of expression of CYP enzymes required for metabolism and catabolism of vitamin D in HSCs, it was demonstrated that these cells are capable of converting plain inactive vitamin D (cholecalciferol) or 25(OH) vitamin $D_3$ (calidiol) to active form of $1\alpha,25(OH)_2$ vitamin $D_3$ (calcitriol) and this active form can further be catabolized to inactive $1\alpha,24,25(OH)_3$ vitamin $D_3$. Quiescent or activated primary HSCs and LX-2 cells cultured on plate for 2-days or 7-days were treated for 24 hours with plain vitamin $D_3$, 25(OH) vitamin $D_3$ and $1\alpha,25(OH)_2$ vitamin $D_3$. Since CYP24A1 is a direct target of active vitamin D, measuring the expression level of this gene indicates the response of different drug treatment. Cholecalciferol was barely able to enhance the CYP24A1 expression at 10 uM concentrations only in quiescent HSCs (FIG. 5A). There was no induction of this gene in culture activated either primary HSC or in LX-2 cells (FIGS. 5C & 6B). In day 2 HSCs, maximal induction of CYP24A1 by both calcidiol and calcitriol was achieved with 10 nM concentrations (FIG. 5B) while in LX-2 cells, maximal enhancement occurred at 100 nM with both ligands (FIG. 6A). Both calidiol and calcitriol were equally potent in activating CYP24A1 in day 2 HSCs or LX-2 cells. However, the response to these drugs by culture activated HSCs or LX-2 cells was significantly reduced. 25(OH) vitamin $D_3$ was moderately increasing the CYP24A1 expression only at 100 nM concentrations while $1\alpha,25(OH)_2$ vitamin $D_3$ was able to maximally induce at 100 nM concentration in HSCs (FIGS. 5C & 6B).

In summary, quiescent HSCs and day 2 LX-2 cells, 10 nM 25(OH) vitamin $D_3$ was as potent as the same concentration of $1\alpha,25(OH)_2$ vitamin $D_3$ in activating CYP24A1 gene expression as this gene is a direct target of active vitamin D. However, in self activated HSCs as well as in 7 day old LX-2 cells, only a 10-fold higher concentration of $1\alpha,25(OH)_2$ vitamin $D_3$ activated CYP24A1 gene expression to the same level as in quiescent culture. On the other hand, even a 10-fold higher dose of 25(OH) vitamin $D_3$, barely induced the CYP24A1 gene expression indicating that either the VDR level or the CYP27B1 enzyme level decreases with cell differentiation.

Thus, functional vitamin D receptor is expressed in both primary rodent HSCs and in the human LX-2 cell line.

Example 4

VDR Ligands Suppress LPS Induced Inflammation in HSCs

This Example demonstrates that VDR ligands suppress LPS induced inflammation in HSCs.

The expression levels of each of the toll-like receptor (TLR) genes were determined in HSCs. Primary HSCs and immortalized LX-2 HSCs similarly expressed TLR1-6 at high levels, as well as expressing TLR 7 and 9 at lower levels. The expression of TLR3 in these cells indicates a link with chronic viral hepatitis-induced inflammation and fibrosis, as dsRNA, which is produced by most viruses during replication, is the cognate ligand of this receptor. Furthermore, when TLR1-4 selective agonists were administered to HSCs, the expected induction of pro-inflammatory chemokines and interleukins was observed.

Figure 7B:
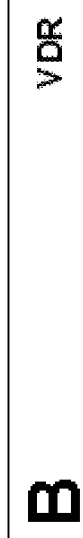
FIGS. 7A and B are bar graphs showing (A) that mRNA expression of TLR4 is upregulated ~3 fold in LX-2 HSCs after 24 hours of 10 ng/ml of LPS, and (B) a timecourse of VDR mRNA upregulation (~3 fold) in LX-2 HSCs after 24 hours of 10 ng/ml of LPS.
Figure 7A:
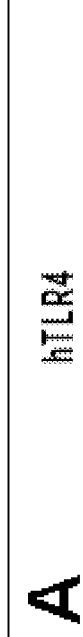

The role of VDR in TLR4-mediated inflammation was investigated by examining the expression of TLR4 and VDR in response to the TLR4-specific ligand, LPS. An approximate three-fold induction of TLR4 message in LX-2 cells was observed after overnight treatment with 10 ng/ml of LPS (FIG. 7A). This indicates that a positive feedback loop for TLR4 expression in HSCs plays a role during the chronic exposure of the liver to endotoxins by potentiating the cellular inflammatory response and ultimately leading to liver fibrosis. In addition, VDR expression was induced in a temporal fashion, and a ~three-fold induction was observed 24 hr after LX-2 cells were presented with a LPS inflammatory challenge (FIG. 7B). These experiments were conducted in parallel with primary HSC cells and similar results were obtained.

The investigation of the genome-wide effects of vitamin D3-activated VDR on TLR4 signaling in NPCs was piloted initially in primary rat HSCs. Isolated primary HSCs were cultured on plastic tissue culture plates for 40 hours prior to treatment with or without vitamin D3 (1 nM) in the presence or absence of 15 ng/ml of LPS for 24 hours. Cells were then harvested, total RNA extracted, and biotin labeled cRNA was prepared for hybridization to Illumina Rat RefSeq version 1 expression arrays. Each treatment was assayed in duplicate or higher replicates. The data generated from these arrays was processed using Illumina BeadStudio software to identify gene expression changes between the different samples. The LPS-mediated changes were identified by comparing non-treated and LPS-treated cells and revealed >500 genes with altered expression. A bioinformatics gene ontology mapping program (GOMINER software) was employed to group the LPS modulated genes into functional pathways. Several categories were identified, including immune response, cytokine production, chemotaxis, response to stress, oxygen and reactive oxygen species metabolism, apoptosis, cell differentiation, cell proliferation, signal transduction and collagen catabolism. Similarly, the genome wide effects of vitamin D3-activated VDR on TLR4 signaling were evaluated by comparing array results from samples treated and untreated with LPS and vitamin D3, as described above.

A well characterized synthetic chemical ligand (T1317) for the nuclear receptor liver X receptor (LXR) was included as it has been demonstrated to have anti-inflammatory properties in bone marrow derived macrophages, and LXR was detected in HSCs in the initial NHR profiling studies. The anti-inflammatory properties of vitamin D3 are summarized in Table 3.

TABLE 3

Regulated gene changes in LPS-treated primary HSCs with vitamin D or LXR ligand (T1317)*

| Gene* | LPS | LPS + Vitamin D3 | LPS + T1317 |
|---|---|---|---|
| Ccl5 | ++++ | ↓ | N/C |
| Ccl20 | ++++ | ↓ | N/C |
| Ccrl2 | ++++ | ++ | ↓ |
| Cx3cl1 | ++++ | ↓ | N/C |
| Cxcl5 | ++++ | ↓ | N/C |
| Cxcl10 | ++ | N/C | ↓ |
| Il-10 | ++++ | N/C | ↓ |
| Il-6 | ++++ | N/C | ↓ |
| Il-1rm | ++ | ↓ | N/C |

*Neutrophil chemoattractants in italics, monocyte chemoattractants in bold text.
N/C means no change Table 3 shows the gene expression changes observed after LPS and LXR ligand treatment on selected inflammatory cytokines, chemokines and interleukins. As expected, a robust induction of the pro-inflammatory genes that function as neutrophil or monocyte attractants was detected, as well as the interleukins 10, 6 and 1RM after LPS treatment. Co-treatment with the LXR agonist (T1317 at 1 μM) markedly decreased the gene induction of the interleukins IL-10 and 6 while conversely, relatively few changes in neutrophil or monocyte attractants were observed. Co-treatment with vitamin D3 preferentially repressed neutrophil and monocyte attractants but did not alter the expression of IL-10 and 6. IL-10 is protective against fibrosis and has anti-apoptopic properties in the liver. The finding that vitamin D preferentially down-regulates immuno-attractants, but appears not to influence the expression levels of IL-10, indicates a beneficial role for VDR signaling in NPCs. These data highlight the diverse anti-inflammatory signaling pathways regulated by NHRs in NPCs and indicate that each receptor has a unique anti-inflammatory gene signature.

These data indicate a unique therapeutic role for vitamin D as an anti-inflammatory treatment in chronic liver injury. In addition, the findings indicate a previously undescribed physiological role for VDR in the liver in the suppression of endotoxin signaling initiated by the constant endogenous exposure to gut-derived endotoxins in HSCs. These protocols are repeated in Kupffer cells (KCs) and sinusoidal endothelial cells (SECs), in which VDR has been reported to be expressed, allowing for a more complete understanding of the role of VDR in NPCs.

Figure 8B:
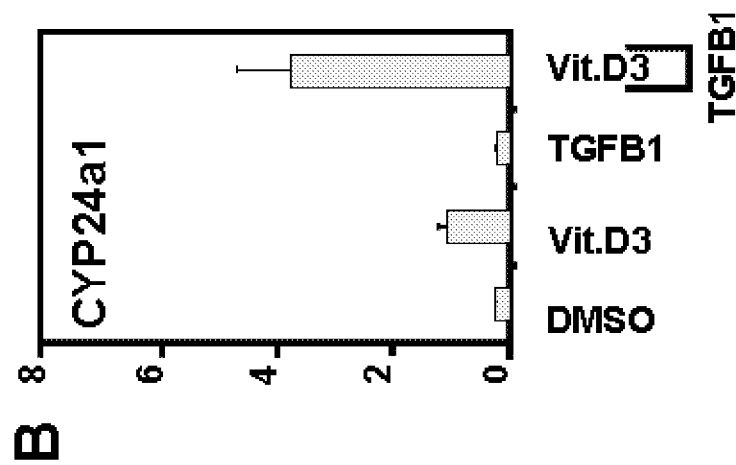
FIGS. 8A and 8B are a diagram and a graph showing (A) a schematic of TGF-$\beta_1$ activation of VDR signaling, and (B) regulation of the CYP24A1 by vitamin D and TGF-$\beta_1$ in LX-2 cells.
Figure 8A:
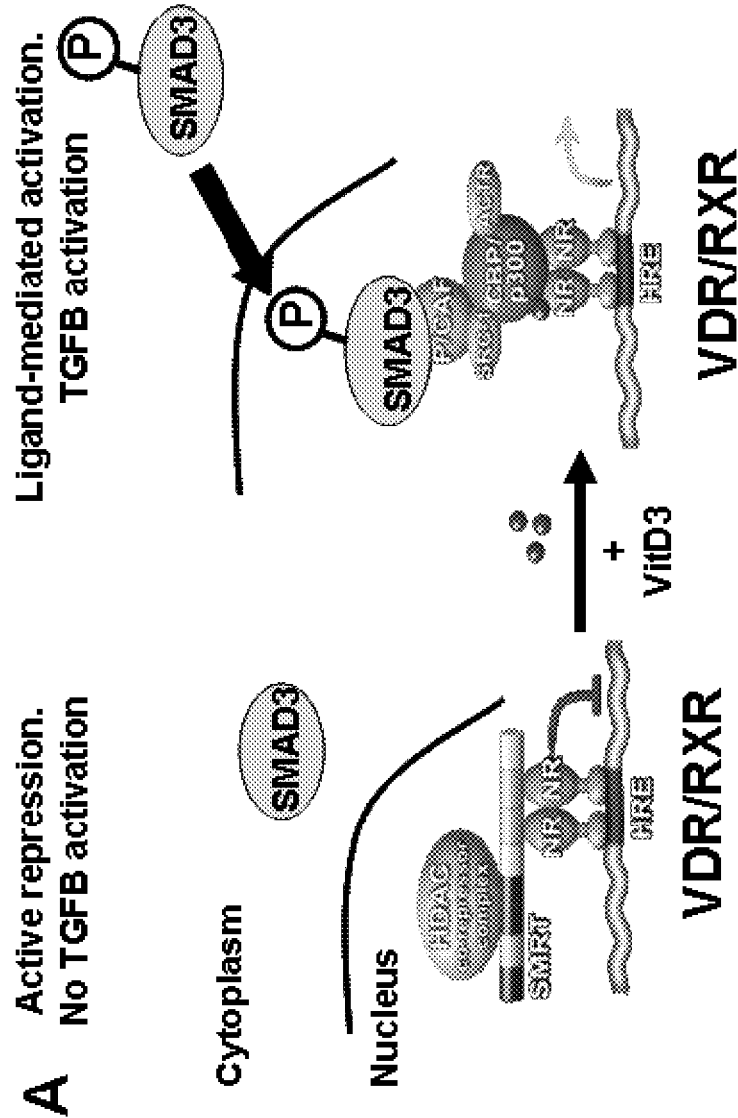

TGFβ signaling is the key mediator in hepatic fibrogenesis, triggering the transition of HSCs into myofibroblast-like cells and thereby stimulating synthesis of ECM proteins. Thus, $TGF\beta_1$ is produced locally in the organ as part of the fibrotic process It has been previously reported that TGFB signaling can influence the activity of VDR-dependent genes, as depicted in (FIG. 8A). In this model, TGFβ activation results in SMAD3 phosphorylation, inducing its translocation into the nucleus where it associates with the ligand bound VDR complex. Phosphorylated SMAD3 acts as a co-activator in the VDR/vitaminD3 complex enhancing the transcriptional potential of VDR on target genes. To understand the interplay between TGFB and VDR signaling pathways, the effects of TGFβ on the well characterized VDR gene target Cyp24α1 were examined. Cultured LX-2 cells were exposed overnight to either the control solvent, DMSO, $1,\alpha25(OH)_2D_3$ (1 nM), TGFβ1 (100 pM) or both $1,\alpha25(OH)_2D_3$ in combination with TGFβ1. Cells were then harvested, total RNA extracted, and cDNA prepared for quantitative PCR analysis of Cyp24α1 gene expression; expression levels were normalized to the ribosomal protein 36B4 expression. The results demonstrate that the vitamin D3 target gene CYP24a1 was robustly induced in LX-2 cells upon administration of physiological levels of vitamin D3 (FIG. 8B). Furthermore, co-administration of TGFβ1 enhanced the vitamin D3 response in these cells, while TGFβ1 alone had no effect on CYP24α1 gene expression. These data demonstrated that LX-2 cells contain functional VDR protein that can activate its target genes, and that there is a functional convergence of the VDR and TGFβ signaling pathways in HSCs.

Having demonstrated that TGFβ modulates VDR signaling in HSCs, it was questioned whether the reciprocal interaction occurred, that is, whether VDR could modulate TGF signaling, particularly with regard to TGFβ induced production of ECM. The Illumina platform described above was used to identify genome-wide effects of vitamin D3-activated VDR on TGFβ signaling in primary rat HSCs. Isolated primary HSCs were cultured on plastic tissue culture plates for 40 hours prior to treatment with or without vitamin D3 (1 nM) in the presence or absence of TGFβ1 (100 pM) for 24 hours. Cells were then harvested, total RNA extracted, and biotin labeled cRNA was prepared for hybridization to an Illumina Rat RefSeq version 1 genome array. Each treatment was assayed in duplicate or higher replicates. The data generated from these arrays was processed using Illumina BeadStudio software to identify gene expression changes between the different samples. The vitamin D3 mediated changes on TGFβ1 signaling were identified by comparing TGFβ1 and co-treated TGFβ1/vitamin D3 samples.

Among the many co-regulated genes identified, those involving ECM proteins are listed in Table 4. As expected, a robust induction of collagen genes by TGFβ was detected as well as a repression of the matrix metalloproteinases (MMPs), including MMP10. MMPs collectively cleave most, if not all, of the constituents of the ECM and are involved in the breakdown and remodeling of many tissues and organs. Co-treatment of TGFB with the vitamin D3 ligand markedly decreased the induction of all collagen genes and inhibited the repression of MMP10 by TGFβ. These results indicate a therapeutic role for vitamin D as an anti-fibrogenic treatment in chronic liver diseases. These findings indicate a new function for vitamin D3 in HSCs. It is expected that the observed functions of VDR can be extended into other NPCs, such as SECs and Kupffer cells, which are the predominant source for TGF under conditions of chronic liver injury.

TABLE 4

ECM gene changes in TGFβ-treated primary HSCs with Vitamin.

| Gene | TGF-β | TGF-β + Vitamin D3 |
|---|---|---|
| Collagen 1a1 | +++ | ↓ |
| Collagen 1a2 | ++++ | ↓ |
| Collagen 3a4 | +++ | ↓ |
| Collagen 5a1 | ++ | ↓ |
| Collagen 5a2 | + | ↓ |
| Collagen 6a3 | + | ↓ |
| Collagen 14a1 | ++ | ↓ |
| Collagen 15a1 | ++ | ↓ |
| Mmp10 | ↓ | N/C* |
| Mmp13 | N/C | N/C |

*N/C means no change

The data strongly implicate VDR as an important player in hepatic inflammation and fibrosis, and predict that its signaling pathway may underlie the protective role of VDR against the endogenous endotoxic environment of the liver.

Example 5

1α,25(OH)$_2$ Vitamin D$_3$ Counteracts LPS-Induced Innate Immune Response and TGF-β1-Mediated Up-Regulation of ECM Genes in HSC Quiscent HSCs grown on culture plates for 40 hours were treated with LPS (15 ng/ml), TGFβ (2 ng/ml) and/or 10 nM 1α,25(OH)$_2$ vitamin D$_3$ (calcitriol) for 24 hours. Illumina microarray analysis identified genes that were differentially regulated. Two different HSCs from different rats were used for the lumina microarray analysis. Microarray analysis on rat HSCs stimulated with LPS, TGF-β1 and/or 1α,25(OH)$_2$ vitamin D$_3$ revealed that LPS primarily activated genes involved in innate immunity/inflammation while TGF-β1 predominantly up-regulated genes that produce ECM proteins. Co-treatment with calcitriol together with TGF-β1 suppressed multiple up-regulated genes associated with pathological ECM production. In the case of LPS, co-treatment with calcitriol significantly attenuated expression of genes involved in innate immunity/inflammation (Table 5). Values are expressed as fold change relative to control cells treated with vehicle alone. Genes in three categories relevant to fibrogenesis (matrix proteins/matrix turnover, inflammatory/cytokine/chemokine, and transcription) are listed.

TABLE 5

Genes differentially regulated in HSCs stimulated with LPS, TGF-β1 and/or calcitriol. All values are fold change relative to controls where control = 1.

| ACCESSION | GENE SYMBOL | TGFβ | Vit.D3 + TGFβ | LPS | Vit.D3 + LPS |
|---|---|---|---|---|---|
| Matrix Proteins & Matrix Turnover | | | | | |
| XM_213440.3 | Col1a1 | 3.014 | 0.897 | 0.321 | 0.343 |
| NM_053356.1 | Col1a2 | 2.256 | 1.052 | 0.695 | 0.676 |
| NM_032085.1 | Col3a1 | 1.878 | 0.770 | 0.341 | 0.417 |
| NM_134452.1 | Col5a1 | 2.322 | 0.778 | 0.871 | 0.758 |
| XM_343564.2 | Col5a2 | 1.583 | 1.080 | 0.680 | 0.678 |
| XM_346073.2 | Col6a3 | 1.611 | 1.024 | 0.914 | 0.918 |
| XM_221536.3 | Col8a1 | 2.240 | 1.011 | 0.882 | 0.859 |
| NM_022266.1 | Ctgf | 1.919 | 0.712 | 0.956 | 0.924 |
| NM_133514.1 | Mmp10 | 1.856 | 0.840 | 3.364 | 3.569 |
| NM_012864.1 | Mmp7 | 1.692 | 0.960 | 0.434 | 0.521 |
| XM_343345.2 | Mmp13 | 1.342 | 1.79 | 5.342 | 4.551 |
| NM_053819.1 | Timp1 | 1.026 | 1.501 | 2.660 | 2.686 |
| NM_021989.2 | Timp2 | 1.823 | 0.976 | 0.573 | 0.527 |
| Inflammatory/Cytokine/Chemokine Signalling | | | | | |
| XM_213425.2 | Ccl12 | 1.167 | 0.274 | 17.248 | 10.282 |
| NM_019233.1 | Ccl20 | 0.999 | 0.95 | 17.287 | 8.442 |
| NM_031116.1 | Ccl5 | 0.957 | 0.252 | 18.315 | 11.401 |
| NM_134455.1 | Cx3cl1 | 0.864 | 1.082 | 10.696 | 5.454 |
| NM_182952.2 | Cxcl11 | 1.05 | 1.276 | 140.915 | 77.611 |
| NM_022214.1 | Cxcl5 | 0.971 | 0.579 | 4.393 | 2.133 |
| NM_145672.3 | Cxcl9 | 0.875 | 0.95 | 3.856 | 1.637 |
| NM_012854.1 | Il10 | 0.837 | 1.02 | 22.295 | 25.724 |
| NM_017019.1 | Il1a | 0.517 | 0.524 | 30.845 | 30.177 |
| NM_031512.1 | Il1b | 0.322 | 0.926 | 36.523 | 32.245 |
| NM_012589.1 | Il6 | 0.791 | 0.54 | 62.156 | 63.928 |
| NM_198769.2 | Tlr2 | 1.092 | 1.285 | 7.181 | 2.930 |
| NM_019178.1 | Tlr4 | 1.349 | 0.989 | 1.380 | 0.815 |
| NM_012675.1 | Tnf | 1.078 | 0.78 | 2.943 | 2.011 |
| XM_345616.2 | Tnfrsf14 | 1.373 | 1.067 | 5.225 | 1.432 |
| XM_230854.3 | Tnfrsf5 | 1.339 | 0.863 | 9.837 | 6.139 |
| XM_340799.2 | Csf2 | 0.803 | 0.931 | 19.886 | 10.988 |
| NM_012967.1 | Icam1 | 1.371 | 0.496 | 4.654 | 5.176 |
| NM_012889.1 | Vcam1 | 1.482 | 1.334 | 4.264 | 8.333 |

TABLE 5-continued

Genes differentially regulated in HSCs stimulated with LPS, TGF-β1 and/or calcitriol. All values are fold change relative to controls where control = 1.

| ACCESSION | GENE SYMBOL | TGFβ | Vit.D3 + TGFβ | LPS | Vit.D3 + LPS |
|---|---|---|---|---|---|
| | | Transcription | | | |
| NM_021578.1 | Tgfb1 | 1.502 | 0.904 | 0.894 | 0.713 |
| NM_012775.1 | Tgfbr1 | 1.317 | 1.242 | 0.736 | 0.699 |
| NM_019191.1 | Smad2 | 1.381 | 0.872 | 0.968 | 0.728 |
| NM_013095.2 | Smad3 | 1.116 | 0.817 | 0.96 | 0.961 |
| NM_019275.1 | Smad4 | 1.325 | 0.886 | 0.803 | 0.54 |

LPS receptor molecules, CD14 and TLRs, and LPS signal transduction pathway mediators, Irak (interleukin receptor-associated kinase), NF-κB and Jak-Stat signalling proteins were induced by LPS treatment (Table 5). While TGF-β1 predominantly up-regulated genes that produce ECM proteins in particular collagen family of proteins (see the table). The levels of TGF-β1 ligand, its receptor (Tgfbr1) and intracellular transducing proteins, Smads, were significantly increased by TGF-β1 treatment in HSCs. In addition, fibronectin and connective tissue growth factor (CTGF) genes were also up-regulated. Interestingly, the very same collagen genes up-regulated by TGF-β1 were down-regulated by LPS. Co-treatment of 1α,25(OH)$_2$ vitamin D$_3$ together with TGF-β1 suppressed the up-regulated genes that produce ECM proteins and revert back to the control gene expression level whereas co-treatment in the case of LPS significantly reduced up-regulated genes involved in innate immunity/inflammation.

In summary, array data analysis revealed that elevated gene expression in the LPS-activated or TGF-β1-activated HSCs clustered into distinct functional groups. This data suggests HSCs express functional LPS-binding complex and are able to respond to bacterial cell wall product and produce an inflammatory phenotype, up-regulating range of chemokines (CC-ligands and CXC-ligands) and cytokines that includes large number of interleukins (e.g., IL-1α, IL-1β, IL-6, IL-10, IL-15), interferons and TNF superfamily members. LPS insult also induced number of signaling molecules including NF-κB, Janus kinases (JAK1 and JAK2) and STAT proteins. Induction of NF-κB, a critical proinflammatory signalling mediator, leads to induction of many chemokines, adhesion molecules (ICAM1, VCAM1) and cytokines including TNF superfamily involved in the inflammatory response. On the other hand, HSCs activated by the TGF-β1 show up-regulation of matrix proteins such as collagens, fibronectin and CTGF and the ECM gene enhancement was supported by decreased expression of MMPs and in particular MMP9 and MMP10 while only the TIMP2 was up-regulated. ECM synthesis and degradation is a dynamic process in liver fibrosis and our result reinforce that TGF-β1 potentiate matrix deposition while LPS supports the matrix degradation. In addition, large number of pro-inflammatory high-threshold gene induction together with negligible number of pro-fibrogenic gene activity in a LPS-mediated HSC activation suggest that endotoxin insult is less injurious and may have a protective mechanism against liver fibrosis. This illustrates two different HSC mode of activation in that possibly the LPS action contributes to repair as an acute phase response while TGF-β1 is involved in chronic phase response.

LPS induces an innate immune response while the TGF-β1 up-regulates ECM genes in HSCs. Microarray data show that 1α,25(OH)$_2$ vitamin D3 attenuates pro-inflammatory effects of LPS and pro-fibrogenic effects of TGF-β1. Reduced binding of NF-kB, a critical pro-inflammatory signalling mediator, by co-treatment with 1α, 25(OH)$_2$ vitamin D3 provides a mechanism for anti-inflammatory actions of active vitamin D. The ability of 1α,25(OH)$_2$ vitamin D3 to regulate pro-inflammatory and ECM genes in HSCs indicates that VDR is a valid target for vitamin D-related compounds as anti-fibrotic agents, for example in liver disease.

Example 6

Treatment of CCL$_4$-Induced Fibrotic Injury with Calcidiol

This example demonstrates that the vitamin D precursor 25-OH vitamin D$_3$ (calcidiol) can be used to treat fibrosis of the liver. Similar methods can be used to treat fibrosis of other organs and using other VDR agonists.

Knowing that HSCs express VDR and synthesize active vitamin D, an in vivo study was performed to test the effect of 25-OH vitamin D$_3$ in a CCl$_4$-induced liver fibrosis model. The CCl$_4$ model of chronic liver injury and fibrosis is a well established model of liver injury, inflammation, fibrosis and cirrhosis where CCL$_4$ is metabolized in the liver by CYP2E to a trichloromethyl free radical, which reacts with oxygen to produces a highly reactive peroxytrichloromethyl radical that initiates a damaging cycle of lipid membrane peroxidation and cell death (Leclercq et al., 2001. *J. Gastroenterology and Hepatol.*, 24:51-59). With iterative injury (3 months in mice), extensive scarring develops as indicated by transdifferentiation of HSCs into myofibroblasts, intense myofibroblast proliferation and progressive laying down of ECM components. Following cessation of CCl$_4$ injections, the scarring resolves completely (Kanzler et al., 1999. *Am J Physiol.*, 276(4 Pt 1):G1059-68). These distinct phases of injury, repair, and resolution make this an ideal model for studying both injury and repair mechanisms.

Eight week-old C57BL6 mice were injected with 2 ml/kg body weight of CCl$_4$ i.p. (1:1 v/v in corn oil) or vehicle alone twice weekly for 4 to 12 weeks. Specifically, groups of mice (n=8 per group per time point) are sacrificed at 48 hours (acute injury), 4, 8 and 12 weeks. The animals were terminated after a period of 72 hours after the final CCl$_4$ injection and whole liver, intestine and serum were collected for histological, cytological, biochemical and molecular analyses. Based on the 1000 IU/kg dosing, mice received 1 IU (25 ng) of vitamin D precursor [25(OH) vitamin D$_3$ (calcidiol)] per gram body weight by either oral gavage or IP injection twice weekly with treatment commencing 3 days prior to CCl4 treatment. The vitamin D supplement was solubilized in corn oil (IP injection, vol=0.25 ml) or medium chain triglyceride oil (oral gavage, vol=0.25 ml). Control mice received vehicle alone.

Figure 9:
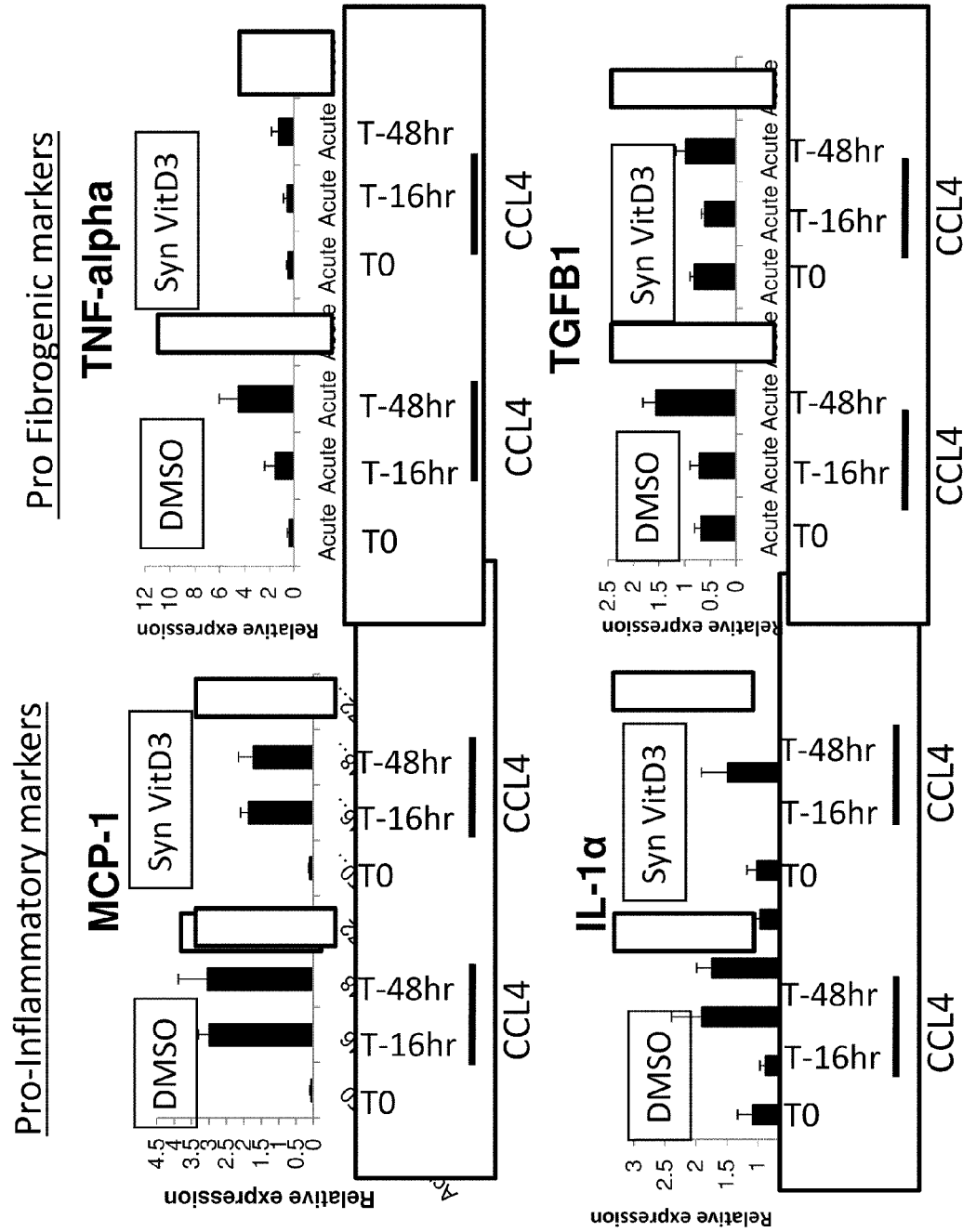
FIG. 9 is a series of bar graphs showing expression of various proteins in the liver following administration of $CCl_4$ in the presence (Syn VitD3) or absence (DMSO) of a synthetic vitamin D receptor agonist.

Twice weekly administration of $CCl_4$ for 6-12 weeks caused sustained hepatocyte damage as evidenced by significant increases in serum ALT levels and marked histological changes in liver sections stained with hematoxylin and eosin. Serum ALT, AST and triglyceride (TG) and hepatic lipid peroxides (by TBARs) and TG were measured biochemically. Liver histology was scored blindly by a histopathologist using the Brunt system to determine levels of steatosis and inflammation. Expression levels of key genes involved in BA (Sult2a1) and cholesterol metabolism, transport (Bsep, Ntcp, Mdr1&2, Mrp2&3, Oatp1, 2&4), and synthesis (Srebp2, Cyp7a1) and the NXRs (Lxr, Car, Pxr & Fxr) regulating these genes were determined by real-time quantitative PCR (QPCR) with results normalized to beta-2-macroglobulin (B2M). Protein expression was examined in a select number of genes by Western blotting. Statistical analysis was completed on SPSS v14 using Kruschal Wallis H and Mann-Whitney U tests with $p<0.05$ considered significant As shown in FIG. 9, administration of calcidiol significantly reduced production of inflammatory and fibrogenic markers. For example, expression of MCP-1, TGFβ1, and IL-α decreased about 50%, and there was no induction of TNF-α.

These data indicate calcidiol and other VDR precursors can be used to treat fibrosis.

Example 7

Treatment of Methionine and Choline Deficient (MCD) Diet Model of NASH with Calcidiol This example demonstrates that the vitamin D precursor 25-OH vitamin $D_3$ (calcidiol) can be used to treat fibrosis of the liver. Similar methods can be used for other vitamin D precursors or VDR agonists.

The methionine and choline deficient (MCD) diet model of nonalcoholic steatohepatitis (NASH) was originally developed in the mid 1990's to provide a suitable animal model to study the pathogenesis of this common human disease (Weltman et al., 1996. *Gastroenterology.*, 111(6):1645-53). It faithfully reproduces the hepatic steatosis, lobular inflammation and fibrosis progressing over time to more severe fibrosis as observed in the human condition. The mouse version of this model has previously been well characterized and reproducibly mice develop hepatic steatosis, inflammation and extensive perivenular and pericellular fibrosis by 10 weeks.

Male C57black wild-type and the VDR floxed knockout mice are fed ad libitum a high fat, MCD diet (ICN cat no: 960439) for up to 10 weeks. Controls are pair-fed the same diet supplemented with choline chloride (2 g/kg) and DL-methionine (3 g/kg). Based on the 1000 IU/kg dosing, mice received 1 IU (25 ng) of vitamin D precursor [25(OH) vitamin $D_3$ (calcidiol)] per gram body weight by either oral gavage or IP injection twice weekly with treatment commencing 3 days prior to CCl4 treatment. The vitamin D supplement was solubilized in corn oil (IP injection, vol=0.25 ml) or medium chain triglyceride oil (oral gavage, vol=0.25 ml). Control mice received vehicle alone. Mice (n=8 per group per time point or both wild-type and the VDR floxed knockout strains) are sacrificed by exsanguination (under anaesthesia) at 3, 6 and 10 weeks of MCD or control diet. A portion of liver is placed in buffered formalin solution for later section, histology (steatosis, inflammation and fibrosis) and immunohistochemistry for α-smooth muscle actin. Fibrosis is determined by Sirius Red staining of liver samples. Serum transaminases, lipids and bile acids and liver bile acids are quantified as previously published (Stedman et al., 2006. *Proc Natl Acad Sci USA.*, 103(30):11323-8) and hepatic lipids, glutathione and lipid peroxidation also are analyzed using standard published protocols. Additional tissue portions are snap frozen in liquid nitrogen for later preparation of total RNA for gene expression studies by quantitative PCR and gene arrays.

Administration of calcidiol reduced production of inflammatory and fibrogenic markers. These data indicate can be used to treat fibrosis.

Example 8

Vitamin D Receptor Expressed in Other Liver Cells

As described in Examples 2 and 3, VDR and cytochrome P450 genes are expressed in liver hepatic stellate cells (HSCs). This example demonstrates that VDR and cytochrome P450 genes are also expressed in sinusoidal endothelial cells (SECs) and Kupffer cells (KCs).

Hepatic sinusoidal endothelial cells (SECs) and Kupffer cells (KCs) were elutriated from rat liver and maintained in cell culture. Western blotting was performed as described in Example 1.

Figure 10A:
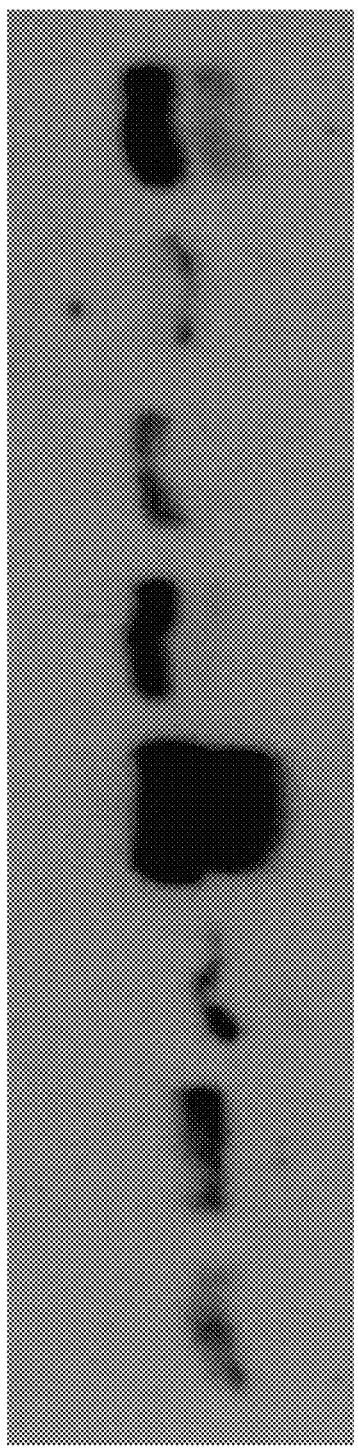
FIGS. 10A and 10B are digital images of western blots showing expression of VDR in (A) sinusoidal endothelial cells (SECs) and (B) Kupffer cells (KCs). Lanes (A) 1. Control; 2. LPS; 3. $1\alpha,25(OH)_2$-vitamin D3; 4. LPS+$1\alpha,25(OH)_2$-vitamin D3; 5. TGF-$\beta_1$; 6. TGF-$\beta_1$+$1\alpha,25(OH)_2$-vitamin D3; 7. 6-keto lithocholic acid; and 8. 6-keto lithocholic acid+$1\alpha,25(OH)_2$-vitamin D3 (B) 1. Control; 2. LPS; 3. TGF-$\beta_1$; 4. $1\alpha,25(OH)_2$-vitamin D3; 5. LPS+$1\alpha,25(OH)_2$-vitamin D3; and 6. TGF-$\beta_1$+$1\alpha,25(OH)_2$-vitamin D3.
Figure 10B:
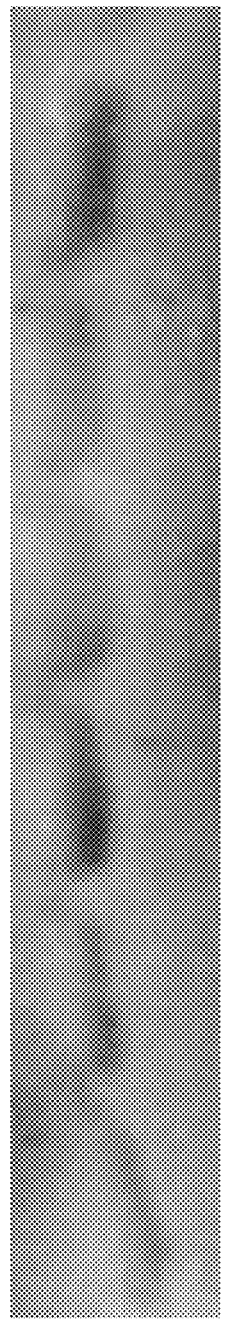

As shown in FIGS. 10A and 10B, VDR protein is expressed in SECs and KCs, and VDR expression is induced by LPS, TGF-$β_1$ and particularly by the combination of LPS and 1α,25-$(OH)_2$-vitamin D3 for SECs and the combination of TGF-$β_1$ and 1α,25-$(OH)_2$-vitamin D3 for KCs.

Figure 11:
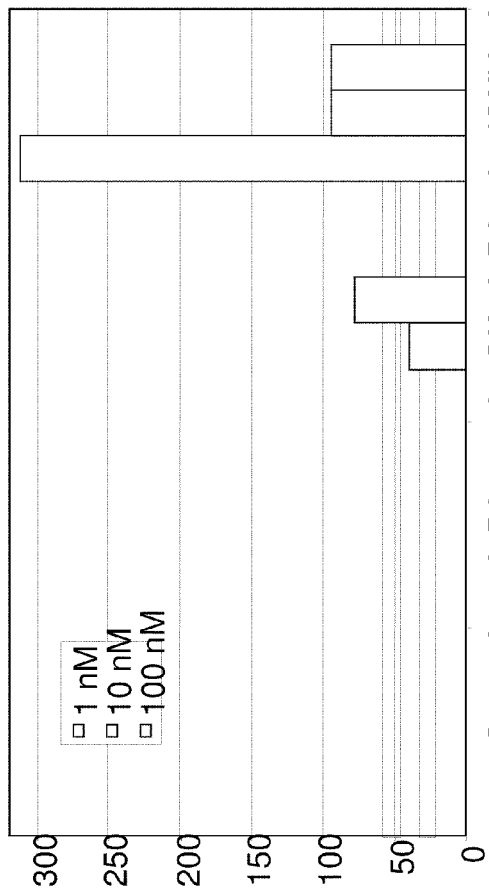
FIGS. 11A and 11B are bar graphs showing Cyp24a1 mRNA expression detected in rat hepatic (A) SECs or (B) KCs treated with vitamin D compounds.
Figure 11:
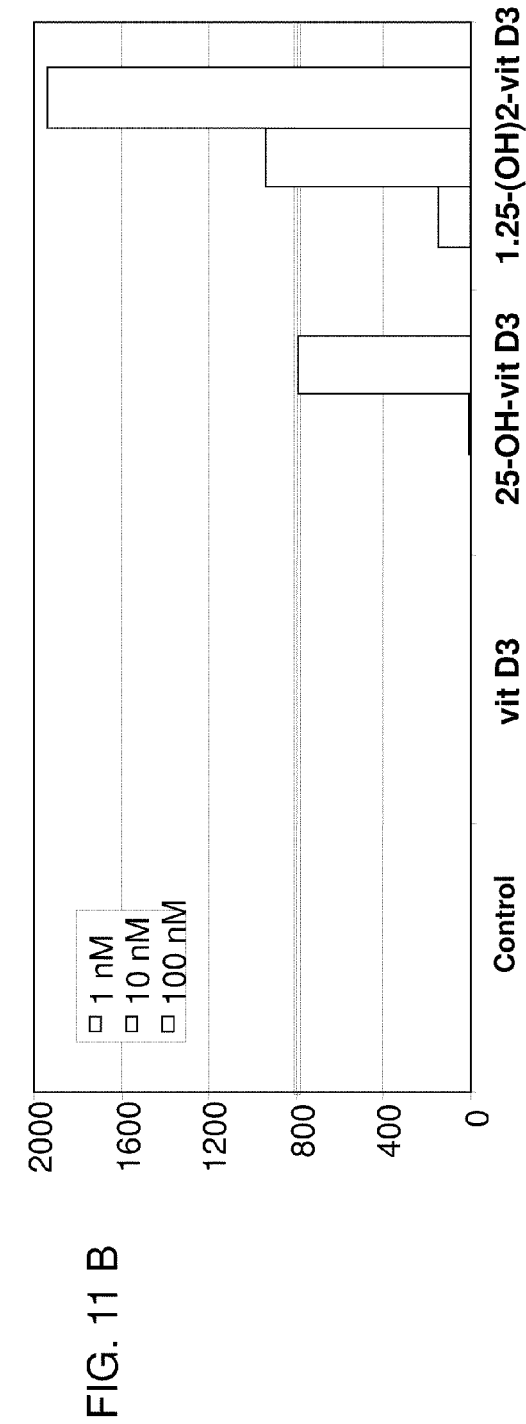

To detect cytochrome P450 expression, hepatic sinusoidal endothelial cells (SECs) were elutriated from rat liver and maintained in cell culture then treated with vehicle alone (Control), Vitamin D3 (vit D3), 25-OH-Vitamin D3 (25-OH-vit D3) or 1α,25-$(OH)_2$-Vitamin D3 (1α,25-$(OH)$2-vit-D3). As shown in FIG. 11A, Cyp24a1 mRNA expression is detected in hepatic SECs treated with vitamin D compounds. As well as being activated by its physiological ligand 1α,25-$(OH)_2$-Vitamin D3, VDR in SECs is also activated by 25-OH-Vitamin D3 at physiologically relevant concentrations through conversion to or 1,α25-$(OH)_2$-Vitamin D3 catalyzed by Cyp27b1 expressed in SECs.

Hepatic Kupffer cells were elutriated from rat liver and maintained in cell culture then treated with vehicle alone (Control), Vitamin D3 (vit D3), 25-OH-Vitamin D3 (25-OH-vit D3) or 1,α25-$(OH)_2$-Vitamin $D_3$ (1,25-$(OH)_2$-vit-D3). As shown in FIG. 11B, Cyp24a1 mRNA expression is detected in hepatic KCs treated with vitamin D compounds. As well as being activated by its physiological ligand 1,25-$(OH)_2$-Vitamin D3, VDR in Kupffer cells is also activated by 25-OH-Vitamin D3 at physiologically relevant concentrations through conversion to or 1,α25-$(OH)_2$-Vitamin D3 catalyzed by Cyp27b1 expressed in Kupffer cells.

Example 9

Bambi Expression in HSCs

This example demonstrates that bone morphogenic protein and activin membrane-bound inhibitor (BAMBI) is expressed in primary rat HSCs subjected to various treatments.

BAMBI is a transmembrane TGF-β pseudoreceptor silences TGF-β signaling (Onichtchouk et al., *Nature* 401: 480-5; 1999). BAMBI has been identified in HSCs and considered to be a major negative modulator of pro-fibrotic TGF-beta1 activity within the liver (Seki et al., *Nat. Med.* 13:1324-32, 2007).

To examine BAMBI expression in HSCs, primary rat HSCs were cultured for 40 hours on plastic prior to treatment for 24 hours with either vehicle (control), 1 nm 1α,25-(OH)$_2$ Vit D3, or LPS (25 ng/ml)+1 nm 1α,25-(OH)$_2$ Vit D3 as described in Example 1. mRNA was detected as described in Example 1.

Figure 12A:
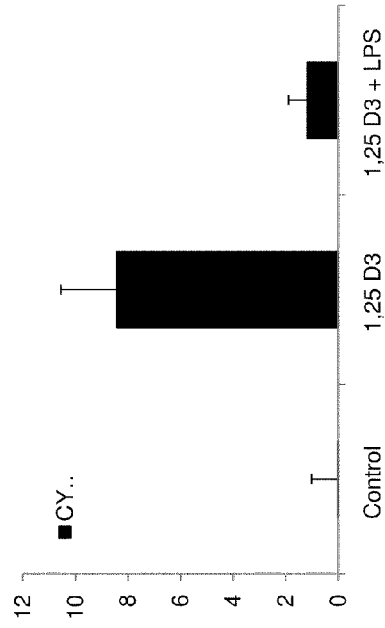
FIGS. 12A-C are bar graphs showing (A) BAMBI, (B) Cyp24a1, and (C) Cyp27b1 mRNA expression detected in hepatic stellate cells.
Figure 12B:
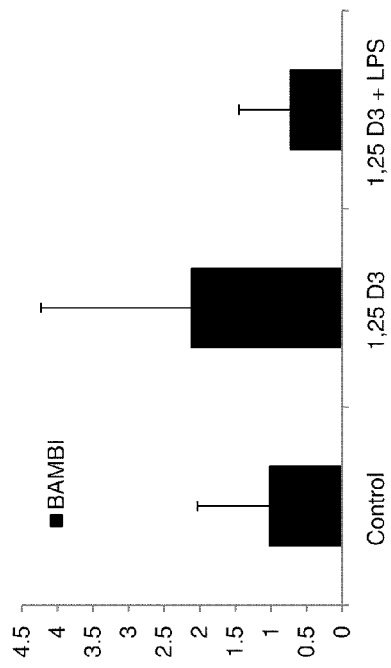
Figure 12C:
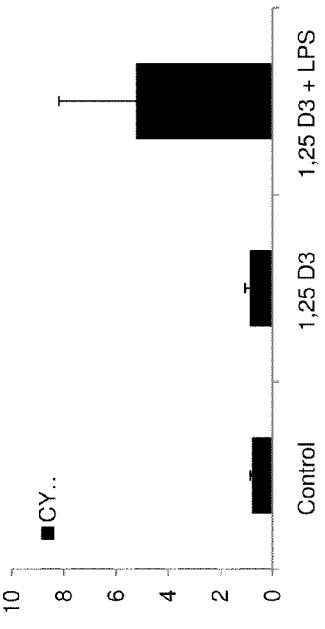
Figure 13:
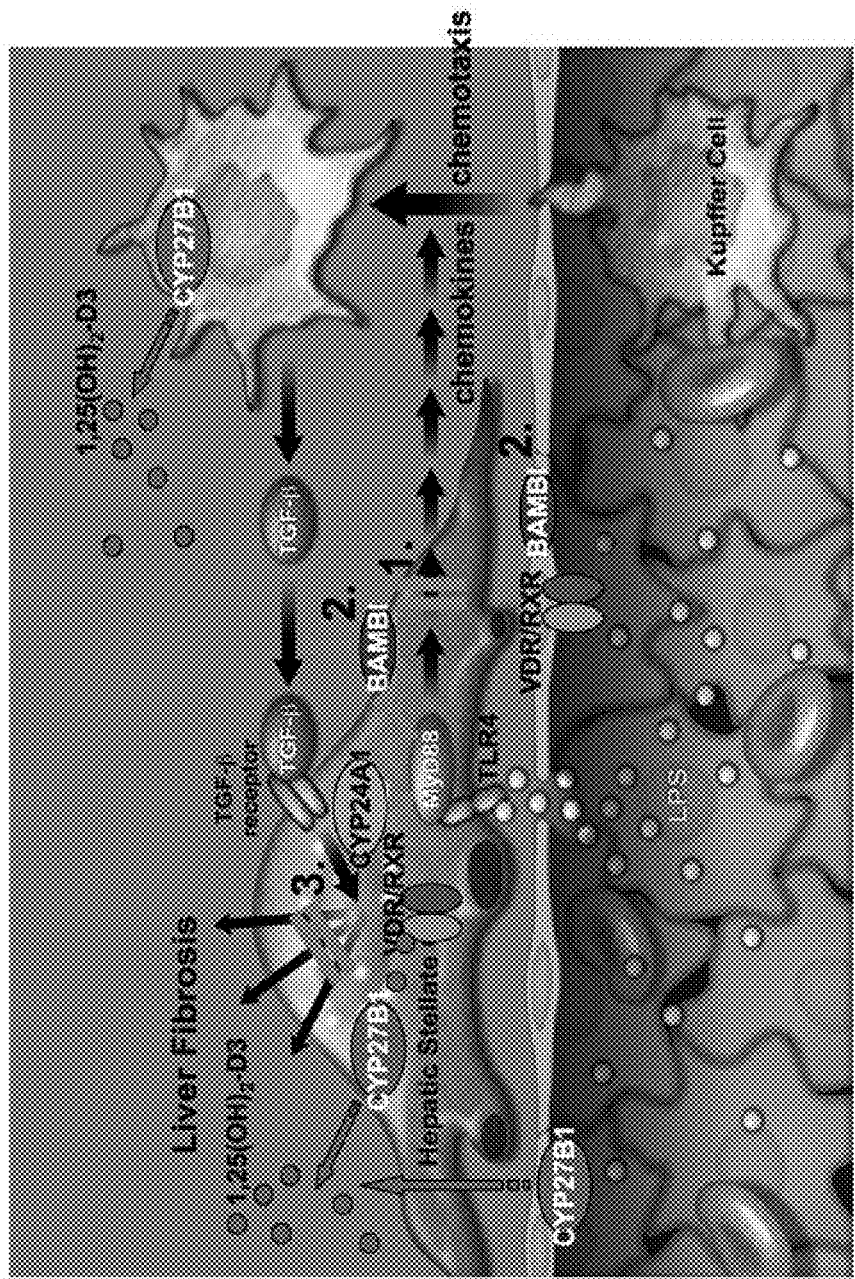
FIG. 13 is a schematic drawing showing that vitamin D acts at multiple sites to inhibit liver fibrogenesis. Hepatic stellate cells, Kupffer cells and sinusoidal endothelial cells express CYP27B1 and produce the physiologically active form of vitamin D [$1\alpha,25(OH)_2D3$], which binds to the vitamin D receptor (VDR). As indicated by the numbered sites on the figure, activation of VDR (1) inhibits synthesis of chemokines by HSCs thereby reducing chemotaxis and activation of Kupffer cells; (2) up-regulates expression of BAMBI on HSCs and SECs, reducing the action of TGF-$\beta_1$; and (3) attenuates TGF-$\beta_1$-induced production of abnormal matrix proteins, especially collagens. In addition, LPS dramatically down-regulates CYP24A1 in HSCs, the enzyme that degrades the physiologically active form of vitamin D [$1\alpha,25(OH)_2D3$], thereby increasing the local availability of this VDR ligand.

As shown in FIGS. 12A and 12B, BAMBI expression is significantly increased in the presence of 1α,25-(OH)$_2$ Vit D3, as is CYP24a1. In contrast, as shown in FIG. 12C, CYP27B1 expression is significantly increased in the presence of both 1α,25-(OH)$_2$ Vit D3 and LPS. Therefore, BAMBI is positively regulated by vitamin D. It is known that LPS negatively regulates BAMBI. Therefore, there is a tug-of-war between LPS and vitamin D in controlling the expression of BAMBI; the more BAMBI expression, the less TGFβ1 signaling and therefore less fibrosis. LPS is a potent negative regulator of CYP24A1, increasing the abundance of 1,α25-(OH)2 Vit D3 by preventing degradation. LPS is a positive regulator of CYP27B1, increasing the formation of 1,α25-(OH)2 Vit D3 from its precursor 25-OH Vit D3.

Example 10

25-(OH)$_2$-Vitamin D3 (Calcidiol) Treatment of Hepatic Fibrosis

This example describes methods that can be used to treat hepatic fibrosis using calcidiol. Although particular human subjects are described (those with hepatic fibrosis secondary to chronic hepatitis C infection) and a particular vitamin D precursor is described, one skilled in the art will appreciate that subjects having fibrosis of other organs or hepatic fibrosis due to other illness, and use of other vitamin D precursors or VDR ligands or other agonists can be used.

Calcidiol, also known as calcifediol, 25-Hydroxycholecalciferol 25-(OH)-D3, and (5Z,7E)-9,10-Secocholesta-5,7,10 (19)-triene-3β,25-diol monohydrate, has the following structure.

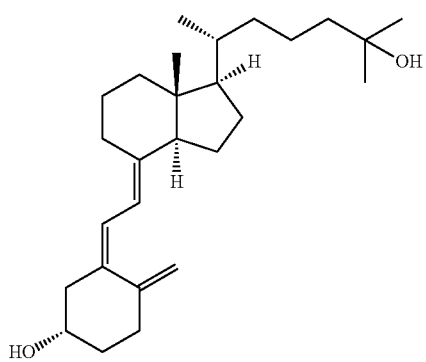

Calcidiol is available as Hidroferol® (Faes, Spain) can be administered orally. It is proposed that calcidiol will be transformed by 25-hydroxyvitamin D3-1-(alpha)-hydroxylase (CYP27B1) to calcitriol, the active form of vitamin D3. Calcitriol binds to intracellular receptors that then function as transcription factors to modulate gene expression. Like the receptors for other steroid hormones and thyroid hormones, VDR has hormone-binding and DNA-binding domains. VDR forms a complex with another intracellular receptor, the retinoid-X receptor (RXR), and that heterodimer is what binds to DNA.

Biweekly doses of calcidiol will be administered for 6 months and the ability to modify the fibrogenic process in hepatitis C patients determined. FibroScan and serum markers will be used to assess liver fibrosis, and acute phase proteins and circulating cytokines to measure of inflammation. Patient-derived DNA samples will be stored for single nucleotide polymorphism testing of selected genes involved in the inflammatory and fibrogenic processes. The ability of calcidiol to improve inflammatory markers and liver function will also be assessed by acute phase proteins, circulating cytokines and other specific biomarkers.

Generally, patients will have the following characteristics: age>18 yrs, hepatitis C with METAVIR score F2 or greater, failure to achieve sustained response to interferon-based therapies (defined as detectable HCV RNA 6 months after the end of treatment), liver disease classed as Child's Pugh Score A. In particular examples, the subject does not have one or more of the following: Child's Pugh Score B or C, co infection with HIV or Hepatitis B, renal impairment (serum creatinine>130 μmol/L), vitamin D sensitivity, hypercalcemia, hypervitaminosis D, parathyroid disease, concomitant therapy with one of the following: cholestyramine, colestipol, digoxin, ketoconazole, orlistat, mineral oil, antiepileptic, water pills, antacids, calcium and magnesium supplements, vitamin D analogues, pregnant or lactating, inability to give written informed consent, or inability to give blood samples.

Calcidiol 266 micrograms (10,640 IU) oral ampoules will be administered orally twice a week. The relationship between calcidiol serum levels and toxicity is poorly characterized. Recent studies have shown that doses in the range of 100 μg (4,000 IU) to 250 μg (10,000 IU) per day are safe. Isolated reports have shown that levels exceeding 500 nmol/l (20,000 IU) were associated with changes in calcium homeostasis and no evidence of adverse effects is reported with serum calcidiol <140 nmol/L requiring a supply of 250 μg (10,000 IU). Cases of high-intake have however been reported (4 and 30 times the upper limit) and well tolerated (Kimball et al., *Ann Clin Biochem*, 45:106-110, 2008). The assembled data from vitamin D supplementation studies reveal a curve for vitamin D dose vs. serum calcidiol that flats up to 250 μg (10,000 IU) (*Biochem. Biophys. Res. Comm.* 2007; 361(1):189-195). The recommended dose of calcidiol according to indications is the following: osteomalacia 1 amp (266 ug)/d, renal osteodystrophy: 1 amp/4 d, hyperparathyroidism: 1 amp/2 d, Resistant rachitism: 1 amp/2 d.

Patients will be monitored by measuring serum creatinine, calcium and phosphate. In case of hypercalcaemia, treatment will be stopped and hypercalcaemia appropriately managed if the patient is symptomatic or Ca>12 mg/dL.

No toxicity is expected with the dose of calcidiol proposed. This precursor of calcitriol has a very high therapeutic index and doses well in excess of those to be used have not been associated with toxicity. Early side effects related to overdose of the active form of vitamin D (calcitriol) (hypervitaminosis D) include: bone pain, arthralgia, myalgia, constipation, dry mouth, headache, metallic taste, nausea, vomiting, unusual tiredness, or weakness. Late side effects include: hypercalcemia, polyuria, polydypsia, arrhythmia, HTA, anorexia, seizure, epigastralgia, weight loss, elevation nitrogen and protein, ectopic calcifications. Hypervitaminosis D and hypercalcemia are contra-indications to calcidiol therapy. Calcidiol should be used be caution in patient immobilized, with antecedent of renal lithiasis, or hyperphosphatemia and patients with these conditions will be excluded from this study. Drug interactions are described with other vitamin D analogues or derivatives, digoxin, anti-acids containing magnesium, aluminium or calcium, anticonvulsants (phenobarbital, phenyloin), colestyramin, colestipol, thiazides diuretics.

Evaluation will be performed in the 7-14 days preceding the administration of the first dose of calcidiol, then every fortnight for the 1$^{st}$ month then monthly until the end of the study at the 24$^{th}$ week. Before the start of treatment, blood tests will be performed within 7-14 days prior to enrollment to assess values of liver function (AST, ALT, and bilirubin), renal function (creatinine), calcium, phosphate, 25-OH-vitamin D and Full Blood count (FBC). Medical records and results of previous imaging investigation will be evaluated for the presence of liver cirrhosis (small liver with irregular outline or features of portal hypertension). Liver histology from previous biopsy will be quantitated using the METAVIR score, date of liver biopsy, date of Hepatitis C diagnosis, previous response to treatment, radiological reports and HCV RNA levels will be recorded.

Before, during, and after at least 6-months of treatment, a Hepascore will be determined for each subject. This is an Australian algorithm of 4 serum markers (bilirubin, gamma-glutamyltransferase, hyaluronic acid, alpha 2 macroglobulin) combined with age and sex, used to predict liver fibrosis stage validated among hepatitis C patients as accurate and reliable (Adams et al., *Clinical Chemistry*, 51(10):1867-1873, 2005, incorporated by reference). In addition, biomarkers of inflammation and liver cell injury will be assessed in blood (CRP, haptoglobin, ALT, AST, gammaGT) as well as fibrogenic cytokines (transforming growth factor TGFβ, platelet derived growth factor PDGF, insulin-like growth factor 1 IGF1, endothelin 1, angiotensin II), cTGF, inflammatory cytokines (TNF alpha, IL-6, Th1 and 2 chemokines) and other biomarkers of fibrosis and ECM turnover such as PIIINP, matrix metallo proteinases (MMPs), tissue inhibitor of metalloproteinases (TIMPs) and laminin. DNA samples will be stored for later single nucleotide polymorphism and haplotype analysis. For example, these parameters can be assessed before treatment, then assessed each fortnight for the 1$^{st}$ month (week 2, 4) and every month until the 24$^{th}$ week (week 8, 12, 16, 20 and 24). Calcium, phosphate, creatinine, full blood count, liver test, and 25-OH-vitamin D will also be assessed. A summary is provided in the Table 6 below:

TABLE 6

Treatment summary

| Required Investigations | Eligibility | Week 0 | Week 2, 4, 8 | Week 12 | Week 16, 20 | Week 24 |
|---|---|---|---|---|---|---|
| FibroSan | | X | | X | | X |
| Serum biomarkers | | | | | | |
| Hepascore | | | X | X | X | X | X |
| Other biomarkers | | | X | X | X | X | X |
| Inflammation parameters | | | | | | |
| CRP | | | X | X | X | X | X |
| Cytokines analysis | | | X | | X | | X |
| Other laboratory test | | | | | | |
| Full blood count | X | X | X | X | X | X |
| Liver tests | X | X | X | X | X | X |
| Creatinine, calcium, phosphates, 25-OH-vitamin D | X | X | X | X | X | X |
| Other | | | | | | |
| DNA sample | | X* | | | | |
| Adverse events systematically reported | | X | X | X | X | X |

In this study, all patients will receive active treatment and patients act as their own controls. Primary endpoints are serum markers of hepatic fibrosis. Secondary endpoints are serum markers of inflammation and liver injury.

Example 11

Alternation in Gene Expression in HSCs in Response to Vitamin D3

This example provides HSC genes whose expression is altered in response to treatment with 1α,25(OH)$_2$-vitamin D3 (calcitriol).

The usual in vitro method for "activating" HSCs and causing them to trans-differentiate into pathological matrix producing myofibroblasts is to culture them on plastic (see Example 1). To identify changes in RNA expression, RNA was isolated from freshly isolated 'quiescent' rat HSCs and HSCs cultured on plastic for 3 days, with and without 10 nM 1α,25(OH)$_2$-vitamin D3 as described in Example 1. The isolated RNA was analyzed using lumina gene expression arrays using two experimental replicates as described in Example 1.

Approximately 9,500 significantly expressed genes were detected in HSCs by the Illumina Rat version 1 gene expression arrays. Day 3 HSCs treated with vitamin D were more like fresh quiescent HSCs than they were like day 3 HSCs without 1α,25(OH)$_2$-vitamin D3. This data demonstrates that treatment of HSCs with VDR agonists pushes the cell towards the quiescent phenotype, which is the desired therapeutic response for fibrosis patients. These results also indicate that circulating Vitamin D (including all forms) levels can be a diagnostic tool for fibrosis progression. Specific genes were identified that were upregulated or downregulated as shown in Tables 7 and 8. Table 7 lists genes in rat HSCs where the expression has reduced significantly by day 3 in culture as compared to fresh HSCs and the gene expression is effectively restored by treatment with 1α,25-(OH)$_2$ vitamin D3. Table 8 lists genes in rat HSCs where the expression has increased significantly by day 3 in culture as compared to fresh HSCs and the gene expression is effectively reduced by treatment with 1α,25-(OH)$_2$ vitamin D3.

TABLE 7

| SYMBOL | Fresh HSC | Day 3 HSC | Day 3 HSC + VitD3 | ACCESSION |
|---|---|---|---|---|
| Abcb4 | 781.2 | 229.9 | 634.3 | NM_012690.1 |
| Acpp | 747.1 | 163.1 | 728.6 | NM_020072.1 |
| Actn1 | 1457.8 | 809.1 | 1281.8 | NM_031005.1 |
| Adarb1 | 255.5 | 121.8 | 212.7 | NM_012894.1 |
| Adcy4 | 3869.7 | 1114 | 3434.5 | NM_019285.1 |
| Add3 | 606.2 | 411.4 | 678 | NM_031552.1 |
| Adk | 825.8 | 613.4 | 889.3 | NM_012895.3 |
| Adprhl2_predicted | 481.9 | 280.9 | 443.4 | XM_342918.2 |
| Adprt | 6123.7 | 2732.3 | 5858.6 | NM_013063.2 |
| Adrb2 | 389.1 | 194.7 | 386.5 | NM_012492.1 |
| Aga_predicted | 3331.8 | 2150.9 | 3049.2 | XM_214403.3 |
| Ak2 | 638.9 | 413 | 583.4 | NM_030986.1 |
| Akr1a1 | 17125.6 | 11673.1 | 15845.7 | NM_031000.2 |
| Amigo2 | 1493.5 | 293.3 | 1778.3 | NM_182816.2 |
| Ampd1 | 162.5 | 90.3 | 152.5 | NM_138876.1 |
| Anp32a | 820.8 | 406.6 | 736.9 | NM_012903.1 |
| Ap1g1 | 654.5 | 452.5 | 598.4 | XM_341686.2 |
| Apex1 | 3026.2 | 1439 | 2644.2 | NM_024148.1 |
| Arg2 | 184.3 | 91.5 | 197.3 | NM_019168.1 |
| Arhgap17 | 7577.2 | 2978.1 | 6611.1 | NM_022244.1 |
| Arl6ip5 | 921.3 | 660 | 946.8 | NM_023972.2 |
| Atp5b | 23601.8 | 16403.8 | 22791.5 | NM_134364.1 |
| Atp5o | 19972.7 | 12771.9 | 17772.9 | NM_138883.1 |
| Atp6v0e1 | 20498.9 | 13278.3 | 18682.8 | NM_053578.3 |
| Atpaf2_predicted | 1408.4 | 1034.3 | 1333.5 | XM_220522.3 |
| B4galt6 | 2553.8 | 1442.5 | 2244.6 | XM_579528.1 |
| Bak1 | 5939.7 | 4167 | 5511.3 | NM_053812.1 |
| Bambi | 406.1 | 288.8 | 413.1 | NM_139082.2 |
| Basp1 | 4483.2 | 2964.2 | 4095.1 | NM_022300.1 |
| Bax | 414.3 | 278.2 | 403.3 | NM_017059.1 |
| Bcap37 | 4292.3 | 2520.5 | 3905.5 | XM_342755.2 |
| Blcap | 2585.5 | 1152.7 | 2103.1 | NM_133582.2 |
| Blocls2_predicted | 2814.9 | 1963.2 | 2961.8 | XM_215245.3 |
| Brd8 | 803.4 | 560.5 | 762.2 | NM_001008509.1 |
| Bteb1 | 2220.2 | 1273.7 | 1944.9 | NM_057211.1 |
| Btg1 | 7860.7 | 5300.6 | 8187.6 | NM_017258.1 |
| Bxdc1_predicted | 800.8 | 538.4 | 740.3 | XM_215404.2 |
| C1qa | 7737.6 | 5734.8 | 7477.6 | NM_001008515.1 |
| C1qbp | 7259 | 5075.3 | 6956.2 | NM_019259.2 |
| C1qg | 8140.5 | 5748.1 | 7665.1 | NM_001008524.1 |
| C1qr1 | 5506.1 | 3113 | 5140.9 | NM_053383.1 |
| Camk2n1 | 1927 | 1009.3 | 2376.7 | NM_173337.1 |
| Casp1 | 3402.3 | 2179.7 | 3649.4 | NM_012762.2 |
| Catna1 | 13571.6 | 9041.1 | 12319.7 | NM_001007145.1 |
| Ccbl1_predicted | 349.5 | 195.6 | 304.8 | XM_231118.3 |
| Ccnd1 | 6995.2 | 4481.8 | 6317.9 | NM_171992.2 |
| Ccnh | 1885.4 | 1209.4 | 1694.1 | NM_052981.2 |
| Cd2bp2_predicted | 1062.5 | 697.1 | 997.3 | XM_215082.3 |
| Cd69 | 276 | 117.8 | 246.9 | XM_232418.3 |
| Cd86 | 607.6 | 303.7 | 506.5 | NM_020081.1 |
| Cd8a | 482.2 | 252.5 | 442.6 | NM_031538.2 |
| Cdc42ep5_predicted | 1390.4 | 1023.9 | 1318.9 | XM_341784.2 |
| Cdk5rap2 | 1095 | 689.7 | 1020.2 | XM_575844.1 |
| Centa2 | 3272.4 | 932.5 | 2736.4 | NM_020101.1 |
| Cetn3 | 1476.7 | 1073.5 | 1383.3 | XM_342168.2 |
| Chka | 437.9 | 313.4 | 400.4 | NM_017127.1 |
| Chordc1_predicted | 1743 | 1181.5 | 1567.4 | XM_235878.3 |
| Chst10 | 476.7 | 263.2 | 417.1 | NM_080397.1 |
| Cias1_predicted | 746.3 | 183.4 | 1003.1 | XM_220513.3 |
| Cmklr1 | 261.1 | 154.8 | 229.7 | NM_022218.1 |
| Coro1a | 23950.1 | 6325.5 | 19157.3 | NM_130411.2 |
| Coro7 | 5470.4 | 3901.8 | 5019 | XM_220167.3 |
| Cox7b | 9024.5 | 6374.6 | 8324.1 | NM_182819.1 |
| Cox8a | 12017.9 | 7397.5 | 11023.5 | XM_574609.1 |
| Crim1_predicted | 1984.5 | 1482.7 | 1943.8 | XM_233798.3 |
| Crlz1_predicted | 2718.4 | 1873.9 | 2531.6 | XM_573570.1 |
| Csf1 | 7492.5 | 5290.5 | 6770.8 | NM_023981.4 |
| Csrp1 | 3101.5 | 1784.3 | 3035.6 | NM_017148.2 |
| Ctbp2 | 1747.7 | 1063.7 | 1655.1 | NM_053335.1 |
| Ctse | 216.2 | 107.4 | 207.9 | NM_012938.1 |
| Ctss | 7516 | 4715.7 | 8614.1 | NM_017320.1 |
| Cyc1_predicted | 3723.5 | 2630.6 | 3898.9 | XM_216944.3 |
| Cycs | 11109.6 | 6953.5 | 10602.2 | NM_012839.2 |
| Cyp24a1 | 381.9 | 94.8 | 550.3 | NM_201635.1 |
| D123 | 1551 | 967.7 | 1391.5 | NM_053877.1 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| Dapk1__predicted | 3177.3 | 1339 | 2619.4 | XM_225138.3 |
| Dbi | 16188.4 | 10071.4 | 14918.4 | NM_031853.3 |
| Ddit3 | 2131.9 | 1469.5 | 2141.2 | NM_024134.1 |
| Ddx39 | 4428.5 | 3263.2 | 4154.1 | NM_053563.2 |
| Dhrs8 | 3113.9 | 2163.5 | 3554.4 | NM_001004209.1 |
| Dnajb9 | 826.9 | 511.8 | 808.7 | NM_012699.2 |
| Dnase2 | 3317.5 | 1651.4 | 3016.2 | NM_138539.1 |
| Dnclc1 | 12637.3 | 7013.5 | 10851.9 | NM_053319.2 |
| Dnm2 | 2732.9 | 1731.9 | 2516.2 | NM_013199.1 |
| Dok3__predicted | 1807.9 | 1260 | 1922 | XM_225170.2 |
| Dpm1__predicted | 2265.8 | 1544.1 | 2060.8 | XM_215949.3 |
| Dre1 | 636.2 | 416.9 | 572.1 | NM_181473.1 |
| Dscr5__predicted | 1443.3 | 976.4 | 1294.3 | XM_213650.2 |
| Dtr | 1194.2 | 608.1 | 1174.7 | NM_012945.1 |
| Ednrb | 3627.5 | 1141.7 | 3156.5 | NM_017333.1 |
| Egr1 | 734.6 | 495.3 | 716.4 | NM_012551.1 |
| Ela2 | 934.8 | 82.4 | 672.5 | NM_012553.1 |
| Entpd5 | 1475.9 | 775.9 | 1420.9 | NM_199394.1 |
| Epb4.1l4a__predicted | 207.1 | 100.7 | 171.3 | XM_226060.3 |
| Ercc5 | 682.3 | 492.1 | 717.2 | XM_217387.3 |
| Esm1 | 2621.9 | 1812.5 | 2484.7 | NM_022604.2 |
| Fam51a1 | 679.7 | 503.9 | 657.6 | NM_001007756.1 |
| Fdx1 | 2872.1 | 2068.4 | 2738.5 | NM_017126.1 |
| Frag1 | 648 | 483.2 | 634.4 | NM_053895.1 |
| Fut4 | 1690.2 | 749.7 | 1547.5 | NM_022219.2 |
| Fvt1__predicted | 1162.8 | 743.8 | 1069.6 | XM_341106.2 |
| Fxc1 | 1025.1 | 696.3 | 925.3 | NM_053371.1 |
| Gadd45a | 2567 | 736.9 | 2729.5 | NM_024127.1 |
| Gdf15 | 715.6 | 341.9 | 755.1 | NM_019216.1 |
| Gemin6 | 967.6 | 644.8 | 900.1 | NM_001009466.1 |
| Gga3__predicted | 862.1 | 533.8 | 777.4 | XM_340935.2 |
| Ghitm | 4466.7 | 3137.9 | 4553.6 | NM_001005908.1 |
| Glo1 | 4967.6 | 3410.3 | 4646.6 | NM_207594.1 |
| Glrx2__predicted | 2268.8 | 1463.4 | 2166.1 | XM_213890.2 |
| Gltscr2 | 4256.4 | 2817.1 | 4005.9 | NM_207591.1 |
| Gmfg | 4315.5 | 3149.3 | 4192.4 | NM_181091.2 |
| Gna15 | 2122 | 621.2 | 1690.9 | NM_053542.1 |
| Gnb5 | 276.8 | 135.5 | 269.8 | NM_031770.1 |
| Gne | 389.8 | 264.8 | 353.9 | NM_053765.2 |
| Got1 | 2756.6 | 1709.5 | 2408.8 | NM_012571.1 |
| Gpr126__predicted | 321.4 | 196 | 281.1 | XM_218313.3 |
| Gpr65__predicted | 1143.4 | 679.6 | 995.5 | XM_234367.2 |
| Gprk5 | 833.1 | 456.4 | 719.2 | NM_030829.1 |
| Gpsm3 | 1387.9 | 842.8 | 1403.4 | NM_001003974.2 |
| Gtf2f1 | 1448.1 | 1080.5 | 1324 | NM_001007711.1 |
| Gtf2i | 1318.8 | 985.5 | 1247.8 | XM_579056.1 |
| Gtlf3b__predicted | 319.1 | 224.5 | 299.2 | XM_343907.2 |
| Hebp1__predicted | 5466.3 | 2413.6 | 5093.7 | XM_342775.2 |
| Hist2h3c2__predicted | 672.1 | 469.7 | 625 | XM_227460.3 |
| Hnrpa3 | 1145.2 | 791.7 | 1034.8 | NM_198132.2 |
| Hnrpl | 9085 | 6209.3 | 8267.7 | XM_214878.3 |
| Hpcl2 | 448.8 | 244.1 | 411.8 | NM_053493.1 |
| Hps1 | 2314.8 | 1662.5 | 2367.6 | NM_040669.1 |
| Hrpap20 | 593.9 | 409.9 | 575.8 | NM_198783.1 |
| Hyal2 | 1781.8 | 1018.9 | 1830.3 | NM_172040.1 |
| Icam1 | 4237.1 | 2683.4 | 5188.4 | NM_012967.1 |
| Ifitm3 | 4163.2 | 2932.9 | 3776.9 | XM_341957.2 |
| Igsf4b__predicted | 274.2 | 177.1 | 261.8 | XM_341157.2 |
| Il1a | 2710.8 | 872.3 | 3499.5 | NM_017019.1 |
| Il6 | 816.1 | 495.9 | 728 | NM_012589.1 |
| Ilk | 7089.8 | 5000.5 | 6466 | NM_133409.2 |
| Ilvbl__predicted | 787.4 | 541.6 | 736 | XM_343174.2 |
| Impdh1__predicted | 4191.9 | 3044.9 | 3995.8 | XM_342650.2 |
| Irf3 | 2611.4 | 1778.7 | 2565.6 | NM_001006969.1 |
| isg12(a) | 4833.3 | 3170.4 | 4787.9 | NM_203410.1 |
| Junb | 7060.7 | 2941.8 | 5923.4 | NM_021836.2 |
| Jundp2 | 334.5 | 118.9 | 269.7 | NM_053894.1 |
| Klhl6__predicted | 431.9 | 254.9 | 447.1 | XM_221290.3 |
| Lancl1 | 603.3 | 430.9 | 567.4 | NM_053723.1 |
| Ler3 | 7341.7 | 4628.2 | 6485.9 | NM_212505.1 |
| LOC171553 | 2873.6 | 1429.7 | 2455.7 | NM_138524.2 |
| LOC287103 | 233.8 | 149 | 222.3 | XM_213226.2 |
| LOC287541 | 2464.7 | 1669.8 | 2471.7 | XM_213403.3 |
| LOC287723 | 1534 | 982.3 | 1496.7 | XM_212676.1 |
| LOC287731 | 5754.3 | 3756.3 | 5395.8 | XM_213467.3 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| LOC287840 | 11063.2 | 7259.6 | 11143.6 | XM_213532.2 |
| LOC288455 | 1327.5 | 888.4 | 1191.2 | XM_213700.3 |
| LOC289443 | 2212.5 | 717.2 | 1815.6 | XM_213999.3 |
| LOC289859 | 2582.9 | 1574.4 | 2268.2 | XM_214120.3 |
| LOC290569 | 891.9 | 528.6 | 784.1 | XM_214278.3 |
| LOC290925 | 2237.7 | 1472.8 | 2160 | XM_214404.3 |
| LOC291060 | 1948 | 1426 | 1861.7 | XM_214453.3 |
| LOC291963 | 7239.4 | 5038.9 | 6501.3 | XM_214664.3 |
| LOC292073 | 259.2 | 152 | 242 | XM_226546.3 |
| LOC292654 | 1731.4 | 1278.7 | 1631.9 | XM_214831.3 |
| LOC292690 | 510.4 | 310.2 | 450.1 | XM_214867.3 |
| LOC292792 | 1717.1 | 1286.1 | 1577.7 | XM_214907.3 |
| LOC293949 | 357.7 | 125.2 | 299.1 | XM_215248.3 |
| LOC294362 | 13237.9 | 8323.7 | 12856.8 | XM_215378.3 |
| LOC294744 | 8949.6 | 6441 | 8315.6 | XM_215486.3 |
| LOC294925 | 5887.9 | 3954.2 | 5257.6 | XM_226988.3 |
| LOC294942 | 588.3 | 342.5 | 601.7 | XM_215541.2 |
| LOC295234 | 6331.9 | 4229.1 | 6104.3 | XM_215630.3 |
| LOC295394 | 1776.7 | 1141.8 | 1634.5 | XM_215691.3 |
| LOC295439 | 21756.4 | 13649.8 | 19564.2 | XM_212946.3 |
| LOC295472 | 16908.2 | 11525.1 | 15325.5 | XM_212947.3 |
| LOC296050 | 3328.6 | 2444.8 | 3185.6 | XM_215787.3 |
| LOC297372 | 579.7 | 425.8 | 527.9 | XM_216191.2 |
| LOC297481 | 966.3 | 585.9 | 957.9 | XM_216226.3 |
| LOC297591 | 4157.4 | 2884.9 | 3961.1 | XM_216272.2 |
| LOC297971 | 364.3 | 260.6 | 333.1 | XM_216368.2 |
| LOC298147 | 1453.6 | 924.8 | 1358 | XM_216433.3 |
| LOC298322 | 250.1 | 128.3 | 227.3 | XM_233279.3 |
| LOC298490 | 1063.7 | 777.8 | 1099.8 | XM_216527.3 |
| LOC299135 | 1237 | 863.4 | 1181.3 | XM_216735.3 |
| LOC299750 | 1282.8 | 911.7 | 1161.8 | XM_235086.3 |
| LOC299828 | 2282.4 | 824.1 | 1898.6 | XM_216903.3 |
| LOC300361 | 2947.6 | 2108.3 | 3071.4 | XM_217080.3 |
| LOC301133 | 240.2 | 93.1 | 254.8 | XM_236794.2 |
| LOC301299 | 14544.4 | 8419.2 | 12638.2 | XM_217361.3 |
| LOC302559 | 1259.6 | 928.6 | 1158.9 | XM_217599.2 |
| LOC303196 | 1391.8 | 773.3 | 1248.4 | XM_220530.3 |
| LOC303395 | 182 | 95.6 | 154.7 | XM_220804.3 |
| LOC303576 | 852.7 | 497.7 | 804 | XM_221003.2 |
| LOC304396 | 751 | 495.6 | 677.1 | XM_222072.3 |
| LOC304638 | 6703 | 4287.6 | 6831.8 | XM_222468.1 |
| LOC305845 | 712.9 | 466.6 | 642.5 | XM_223974.3 |
| LOC307907 | 7878.9 | 2251.4 | 6340.6 | XM_226529.3 |
| LOC308758 | 641.4 | 472.2 | 622.1 | XM_218817.3 |
| LOC310772 | 566.3 | 282 | 549.2 | XM_227570.3 |
| LOC310926 | 4520.1 | 2070.9 | 3770.9 | XM_227769.2 |
| LOC310946 | 2110.8 | 1318.6 | 1875.1 | XM_227795.3 |
| LOC311329 | 398.6 | 279.9 | 385.6 | XM_230468.3 |
| LOC311852 | 207.7 | 104.1 | 205.2 | XM_231131.3 |
| LOC311987 | 513.3 | 296 | 454.4 | XM_231305.3 |
| LOC313824 | 808.3 | 500.9 | 728 | XM_233790.3 |
| LOC313940 | 360.3 | 219 | 338.1 | XM_233953.3 |
| LOC315521 | 482.7 | 289.3 | 461.3 | XM_236007.2 |
| LOC315911 | 259.9 | 164.3 | 237.1 | XM_236533.2 |
| LOC316014 | 547 | 267.5 | 517.2 | XM_236649.3 |
| LOC317258 | 382.5 | 144.9 | 309.2 | XM_228553.3 |
| LOC317380 | 996.9 | 601.2 | 897.2 | XM_228769.3 |
| LOC317444 | 1510.7 | 1025.8 | 1585.8 | XM_228867.3 |
| LOC360303 | 1818.5 | 1138.3 | 1661.1 | XM_346531.2 |
| LOC360568 | 1401.8 | 844 | 1230.8 | XM_340844.2 |
| LOC360575 | 732.5 | 493 | 699.4 | XM_340854.2 |
| LOC360595 | 571.4 | 379.9 | 603.3 | XM_340875.2 |
| LOC360751 | 648.8 | 97.4 | 618.2 | XM_341023.2 |
| LOC360762 | 4306.9 | 2797.5 | 4259.7 | XM_341032.2 |
| LOC360826 | 1035.8 | 661.2 | 1093.3 | XM_341099.2 |
| LOC360975 | 4357.2 | 3206.7 | 4561.9 | XM_573650.1 |
| LOC361074 | 569.1 | 235.4 | 693.6 | XM_341357.1 |
| LOC361163 | 582.5 | 362.6 | 601.9 | XM_341449.2 |
| LOC361178 | 2106.1 | 1523.5 | 2257.4 | XM_573946.1 |
| LOC361448 | 3709.4 | 2439 | 3374.4 | XM_341726.2 |
| LOC361601 | 3135.8 | 2043.9 | 2804.5 | XM_341879.2 |
| LOC361648 | 3010.2 | 1943 | 2898.1 | XM_341927.2 |
| LOC361664 | 883 | 607.5 | 833.6 | XM_341945.1 |
| LOC361695 | 3625.3 | 2326.4 | 3254.3 | XM_341978.2 |
| LOC361767 | 451.3 | 306.2 | 414.8 | XM_342058.2 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| LOC361797 | 2234.4 | 1516.9 | 1997.4 | XM_347003.2 |
| LOC361869 | 21964.9 | 15898.3 | 22630.3 | XM_342164.2 |
| LOC362084 | 761.4 | 532 | 688.1 | XM_342385.2 |
| LOC362153 | 749.7 | 538.7 | 715.9 | XM_342453.2 |
| LOC362289 | 618.8 | 353.1 | 549.7 | XM_342603.2 |
| LOC362597 | 736.7 | 439.1 | 651.6 | XM_342915.2 |
| LOC362848 | 1707.7 | 348.6 | 1569.2 | XM_343179.2 |
| LOC362855 | 1807.7 | 1286.6 | 1685 | NM_207614.1 |
| LOC363087 | 530.6 | 388.2 | 515.4 | XM_343418.2 |
| LOC363162 | 1503.1 | 1025.9 | 1426.4 | XM_343501.2 |
| LOC363289 | 476.1 | 304.6 | 424.5 | XM_343631.2 |
| LOC366411 | 614.1 | 250.6 | 507.9 | XM_575861.1 |
| LOC366500 | 394.4 | 257.6 | 355 | XM_345600.2 |
| LOC366656 | 17488.5 | 11577.2 | 16841.3 | XM_345686.2 |
| LOC367566 | 2503.2 | 1767.9 | 2515.3 | XM_578896.1 |
| LOC497682 | 400.4 | 261.8 | 365.9 | XM_579511.1 |
| LOC497705 | 382.3 | 192.8 | 331.4 | XM_579729.1 |
| LOC497732 | 12309.6 | 8195.5 | 11891.8 | XM_579578.1 |
| LOC497803 | 1741.2 | 1202.2 | 1686.8 | XM_579711.1 |
| LOC497811 | 2299.1 | 1035.1 | 1994.5 | XM_579397.1 |
| LOC497836 | 857.1 | 419.5 | 749.8 | XM_579720.1 |
| LOC497875 | 2573.4 | 768.4 | 2295.3 | XM_573059.1 |
| LOC497882 | 13903.9 | 8975.6 | 12295.9 | XM_573067.1 |
| LOC497954 | 2411.9 | 1728.9 | 2297.5 | XM_573140.1 |
| LOC497993 | 1453.7 | 954.4 | 1382.8 | XM_573190.1 |
| LOC498035 | 1806.1 | 1167.9 | 1690.5 | XM_573236.1 |
| LOC498078 | 4998.9 | 3211.9 | 4525.4 | XM_221473.3 |
| LOC498122 | 678.8 | 456.8 | 605 | XM_573333.1 |
| LOC498185 | 4053 | 2792.6 | 3742.4 | XM_573402.1 |
| LOC498368 | 608.7 | 251.2 | 519.8 | XM_573603.1 |
| LOC498404 | 518.8 | 342.7 | 495.6 | XM_573647.1 |
| LOC498406 | 4582.7 | 2811.4 | 4037.6 | XM_573648.1 |
| LOC498600 | 3466.5 | 2372.9 | 3196.6 | XM_573878.1 |
| LOC498602 | 522.8 | 288.6 | 565.1 | XM_573880.1 |
| LOC498824 | 3427.3 | 2491.9 | 3156.3 | XM_574105.1 |
| LOC498890 | 5845.9 | 3587.6 | 5322 | XM_574178.1 |
| LOC498909 | 2596.5 | 1848.8 | 2441.4 | XM_574198.1 |
| LOC499020 | 2258.5 | 1458.5 | 2199.2 | XM_574313.1 |
| LOC499129 | 1258.6 | 898.9 | 1147.1 | XM_574422.1 |
| LOC499148 | 384.4 | 259 | 374.6 | XM_574443.1 |
| LOC499200 | 761.3 | 382.2 | 814.3 | XM_574487.1 |
| LOC499210 | 1082.5 | 649.1 | 1154.9 | XM_574497.1 |
| LOC499211 | 1399 | 460.1 | 1097.9 | XM_574499.1 |
| LOC499300 | 238.8 | 128.6 | 264.7 | XM_574598.1 |
| LOC499328 | 1137.2 | 784.3 | 1068.2 | XM_574634.1 |
| LOC499391 | 861 | 608.3 | 889.6 | XM_574706.1 |
| LOC499507 | 333.2 | 236.8 | 364.4 | XM_574832.1 |
| LOC499508 | 703.5 | 414.8 | 717.7 | XM_574833.1 |
| LOC499670 | 490.9 | 281.4 | 470.5 | XM_574989.1 |
| LOC499770 | 1087 | 658.8 | 1011.4 | XM_575107.1 |
| LOC499794 | 916.4 | 619.4 | 824.8 | XM_575130.1 |
| LOC500015 | 1215.1 | 764.7 | 1416.4 | XM_575369.1 |
| LOC500039 | 6975.7 | 3915.3 | 5996.5 | XM_575395.1 |
| LOC500040 | 5577.4 | 3772.1 | 5051.5 | XM_575396.1 |
| LOC500257 | 207.3 | 83.6 | 212.6 | XM_575606.1 |
| LOC500262 | 317.2 | 149.6 | 304.5 | XM_575612.1 |
| LOC500384 | 743.9 | 515.8 | 693.7 | XM_575742.1 |
| LOC500419 | 644.8 | 259.4 | 514.4 | XM_575780.1 |
| LOC500650 | 6319.4 | 3813 | 5888.3 | XM_576028.1 |
| LOC500694 | 2029.1 | 1248.3 | 1821.1 | XM_576075.1 |
| LOC500710 | 828.4 | 461.8 | 726.6 | XM_576091.1 |
| LOC500899 | 1244.8 | 898.4 | 1180 | XM_576301.1 |
| LOC500988 | 1460.9 | 857.6 | 1447.6 | XM_576400.1 |
| LOC501058 | 14867.4 | 9740.3 | 13805.7 | XM_576474.1 |
| LOC501105 | 1016.6 | 396 | 1004.5 | XM_576520.1 |
| LOC501709 | 7052.6 | 3919.8 | 6313.2 | XM_577114.1 |
| LOC502902 | 2708.4 | 1156.6 | 2713.8 | XM_578404.1 |
| Lsm8_predicted | 1619.2 | 1156.7 | 1463.2 | XM_216102.3 |
| Lta4h_predicted | 9340.4 | 6330.2 | 8904 | XM_235057.3 |
| Lyar_predicted | 3604.5 | 2561 | 3292.9 | XM_573629.1 |
| Maf | 2616.3 | 1858.7 | 2524.9 | NM_001007673.1 |
| Magoh_predicted | 1309.4 | 910.5 | 1205.5 | XM_216485.3 |
| Mcfd2 | 2601.2 | 1566.1 | 2394.2 | NM_139253.1 |
| Metap2 | 2270.7 | 1504.4 | 2102.3 | NM_022539.1 |
| Mfng | 2121 | 528.7 | 2102.3 | NM_199110.1 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| MGC105647 | 3548.3 | 2045.2 | 3050.3 | NM_001007008.1 |
| MGC105961 | 3682.7 | 2588.3 | 3485.4 | NM_001006985.1 |
| MGC109554 | 4032.5 | 2269.8 | 3701.5 | NM_001009631.1 |
| MGC72984 | 1271.7 | 895 | 1176.6 | NM_001007661.1 |
| MGC93911 | 508.7 | 359.4 | 462.6 | NM_001007674.1 |
| MGC94142 | 3999.4 | 1577.1 | 3499.9 | NM_001004205.1 |
| MGC94464 | 1569.8 | 1044.5 | 1415.6 | NM_001007647.1 |
| MGC95208 | 860.5 | 449.9 | 952.9 | NM_001005552.1 |
| MGC95311 | 1144 | 769.9 | 1045 | NM_001006996.1 |
| Mkl1_predicted | 2405.5 | 1427.6 | 2205.7 | XM_235497.3 |
| Mnab_predicted | 307.4 | 213 | 280 | XM_231249.3 |
| Mpp6_predicted | 1216.9 | 762.8 | 1085.7 | XM_342682.2 |
| Mrpl21_predicted | 2674 | 1939 | 2475.7 | XM_219576.3 |
| Mrpl27_predicted | 3493.7 | 2608.4 | 3271.8 | XM_213439.3 |
| Mrpl41_predicted | 1690.6 | 1170.6 | 1584.1 | XM_216010.3 |
| Mrpl42_predicted | 1588.2 | 1094.5 | 1545.2 | XM_216882.3 |
| Mrpl47_predicted | 1809.2 | 1182 | 1661.9 | XM_215546.3 |
| Mrps26_predicted | 1341 | 564.9 | 1248.5 | XM_342520.1 |
| Mrps33_predicted | 3590.8 | 2371.7 | 3411.1 | XM_216135.3 |
| Mrs21 | 1113.9 | 800.9 | 1010.2 | NM_024001.1 |
| Mrvldc1_predicted | 2749.1 | 1637.9 | 2521.3 | XM_219885 |
| Mrvldc1_predicted | 588 | 391.8 | 539.6 | XM_219885.2 |
| Mta1 | 1613 | 1178.6 | 1747.3 | NM_022588.1 |
| Mtvr2_predicted | 6297.8 | 2465.6 | 5596.5 | XM_219519.3 |
| Myo7a | 502.4 | 232.1 | 410.5 | NM_153473.1 |
| Myo9b | 4432.1 | 3170.6 | 4069.4 | NM_012984.1 |
| Nckipsd_predicted | 617 | 348.6 | 525.3 | XM_238555.3 |
| Ndel1 | 9593.2 | 6174.1 | 8447.1 | NM_133320.1 |
| Ndufb7_predicted | 3979.4 | 2725.2 | 3578 | XM_341664.2 |
| Ndufb9_predicted | 14203.5 | 9648.9 | 13311.6 | XM_216929.3 |
| Ndufs3_predicted | 3365.2 | 1794 | 2998.6 | XM_215776.3 |
| Neo1 | 713.6 | 526.7 | 684 | XM_343402.2 |
| Nfkbia | 5896.2 | 3767.3 | 6072.5 | XM_343065.2 |
| Nkg7 | 210.3 | 137.1 | 185.7 | NM_133540.1 |
| Nmb_predicted | 707.3 | 487.8 | 720.8 | XM_218815.3 |
| Nme1 | 8984.1 | 6220.4 | 8667 | NM_138548.1 |
| Nnp1_predicted | 1260.6 | 865.4 | 1351.8 | XM_574730.1 |
| Nol5 | 6344.5 | 4489.3 | 6108.6 | NM_021754.1 |
| Nrbf2 | 821.2 | 545 | 904.7 | NM_022186.1 |
| Nrip1_predicted | 751.9 | 482.9 | 686.7 | XM_221724.2 |
| Nrtn | 659.3 | 217.9 | 549.6 | NM_053399.1 |
| Nt5 | 3900.3 | 2329.3 | 3481.5 | NM_021576.1 |
| Nudt4 | 3987.1 | 2300.7 | 3688.7 | XM_579565.1 |
| Oasl1_predicted | 778.5 | 502.4 | 958.5 | XM_579309.1 |
| Okl38 | 626.7 | 289.2 | 513.7 | NM_138504.2 |
| Osgep_predicted | 512.2 | 319.4 | 466.1 | XM_214163.3 |
| Palm | 329.4 | 231.1 | 296.7 | NM_130829.1 |
| Papd5_predicted | 1117.5 | 831.3 | 1099.6 | XM_226334.3 |
| Papss2_predicted | 1048.1 | 639 | 1100.5 | XM_215288.3 |
| Pcm1 | 1168.3 | 811.1 | 1086.7 | XM_344524.2 |
| Pdcd5_predicted | 10060 | 6689.3 | 9171 | XM_214911.2 |
| Pde7a | 993.9 | 422.4 | 890.3 | XM_215540.3 |
| Pdgfa | 11790.2 | 3550.2 | 9813.9 | NM_012801.1 |
| Pdhb | 1937.8 | 1240 | 1771.8 | NM_001007620.1 |
| Pgsg | 641.9 | 387.5 | 563.6 | NM_020074.2 |
| Pi4k2a | 896.5 | 445.7 | 840.5 | NM_053735.1 |
| Pigs | 2936.9 | 1938.3 | 2870.8 | NM_001006602.1 |
| Pir | 549.5 | 390.1 | 604.5 | NM_001009474.1 |
| Pitpnm | 310.1 | 182.7 | 271 | NM_001008369.1 |
| Pla2g2a | 1518.9 | 919.2 | 1337.9 | NM_031598.1 |
| Pla2g7 | 4578.6 | 2010.5 | 4210.9 | NM_001009353.1 |
| Plcd1 | 7605.5 | 1945.4 | 6899.5 | NM_017035.1 |
| Plvap | 2304.2 | 1230.1 | 2164.4 | NM_020086.1 |
| Pmp22 | 1551.6 | 1145.1 | 1512.6 | NM_017037.1 |
| Polr2g | 2567.3 | 1529.8 | 2360.5 | NM_053948.2 |
| Polr2h_predicted | 2275.2 | 1482.9 | 2014.7 | XM_213574.3 |
| Ppfia1_predicted | 493.8 | 258.2 | 437.2 | XM_238162.3 |
| Ppib | 12745.7 | 8752.2 | 11455.4 | NM_022536.1 |
| Ppp2ca | 7592.9 | 5133.9 | 6890.1 | NM_017039.2 |
| Prdx2 | 13323.5 | 8360.1 | 12001.8 | NM_017169.1 |
| Prss15 | 2135.6 | 1470.4 | 2073.6 | NM_133404.1 |
| Psma5 | 8000.9 | 4643.8 | 6918.1 | NM_017282.1 |
| Psma6 | 13298.2 | 9361.2 | 12118.2 | NM_017283.2 |
| Psmc2 | 4202 | 2670.9 | 3694.7 | NM_033236.1 |
| Psmd12 | 3184.9 | 2225.8 | 2865.8 | NM_001005875.1 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| Psmd9 | 1789 | 1189.7 | 1692.3 | NM_130430.1 |
| Pstpip1_predicted | 2693.2 | 911.1 | 2479.2 | XM_217152.3 |
| Ptafr | 3149.7 | 2031 | 2958.3 | NM_053321.2 |
| Ptgis | 1545.1 | 1029.4 | 1370.6 | NM_031557.2 |
| Ptgs2 | 5677.5 | 2878.3 | 4730.2 | NM_017232.2 |
| Ptpn1 | 2438.2 | 1149.6 | 2113.8 | NM_012637.1 |
| Ptpn6 | 5208.4 | 3800.7 | 4813.6 | NM_053908.1 |
| Pxmp4 | 620.5 | 358.7 | 532.6 | NM_172223.2 |
| Rab18_predicted | 1959.9 | 1352.5 | 1758.5 | XM_225453.3 |
| Rab5c_predicted | 3154.2 | 2308.5 | 2938.2 | XM_213463.3 |
| Rabl4_predicted | 762.6 | 541.3 | 704.2 | XM_216964.3 |
| Rac2 | 22006.3 | 12744.4 | 19827.2 | NM_001008384.1 |
| Rae1_predicted | 1738.4 | 1186 | 1556.7 | XM_342592.2 |
| Ramp1 | 212.3 | 127.8 | 235.8 | NM_031645.1 |
| RAMP4 | 7337.3 | 4586.3 | 7337.9 | NM_030835.2 |
| Rasgrp2_predicted | 236.6 | 153.8 | 248.8 | XM_342003.2 |
| Rchy1 | 1572.4 | 1072.1 | 1454.9 | NM_001007618.1 |
| Recql_predicted | 2148.4 | 1554.8 | 2057.1 | XM_575714.1 |
| RGD1306284 | 580.1 | 361.2 | 555.4 | NM_001008283.1 |
| RGD1306899_predicted | 279.8 | 189.7 | 256.6 | XM_340998.2 |
| RGD1307475_predicted | 4479.6 | 3039.2 | 4161.6 | XM_344324.2 |
| RGD1307626_predicted | 1316.7 | 915.6 | 1227 | XM_226843.3 |
| RGD1308696 | 2732.1 | 1414 | 2655 | NM_001008278.1 |
| RGD1308734_predicted | 1034.6 | 258.3 | 813.2 | XM_216299.3 |
| RGD1309158 | 1485 | 853.6 | 1390 | NM_001008362.1 |
| RGD1309437_predicted | 598 | 432 | 582.7 | XM_213638.3 |
| RGD1309685_predicted | 1851.1 | 1011.6 | 1708.3 | XM_340936.2 |
| RGD1310191_predicted | 385.1 | 250.3 | 441.1 | XM_341102.2 |
| RGD1310724_predicted | 1156.4 | 766.5 | 1107.7 | XM_341075.2 |
| RGD1311257 | 717 | 329.4 | 604.5 | NM_001008307.1 |
| RGD1311805 | 2900.4 | 1628.9 | 2566.5 | NM_001009638.1 |
| RGD1359127 | 2212.2 | 1659.7 | 2187.2 | NM_001007657.1 |
| RGD1359600 | 486.6 | 340.4 | 439.1 | NM_001007688.1 |
| RGD735106 | 853.1 | 623.9 | 816.9 | NM_198766.1 |
| Rgs2 | 3888.8 | 2535.2 | 4266.6 | NM_053453.1 |
| Rgs3 | 1872.1 | 885.6 | 1599.4 | NM_019340.1 |
| Rhoh_predicted | 954.1 | 550 | 907.9 | XM_223404.2 |
| Rhoj | 851.6 | 629 | 785 | NM_001008320.1 |
| Rhpn1_predicted | 514.8 | 150.8 | 439.3 | XM_216954.3 |
| Ripk1_predicted | 462.2 | 327.8 | 425.8 | XM_225262.3 |
| Ripk3 | 4280.4 | 976.7 | 3391.6 | NM_139342.1 |
| Rnfl11_predicted | 1596.3 | 1124.6 | 1512.2 | XM_236380.3 |
| Rnmt | 484.3 | 344.2 | 445.3 | NM_001008299.1 |
| Rnpep | 1594.8 | 1079.5 | 1477 | NM_031097.1 |
| Rpl22 | 21466.6 | 15266.6 | 20020.8 | NM_031104.1 |
| Rps3a | 23765.1 | 16060.1 | 22660.7 | NM_017153.1 |
| Rras2_predicted | 1620.8 | 424.9 | 1652.5 | XM_344953.2 |
| Rrs1_predicted | 659.7 | 473.1 | 596.2 | XM_232622.2 |
| Sart1 | 364 | 236.8 | 342.6 | NM_031596.1 |
| Sc65 | 1006.8 | 631 | 884.9 | NM_021581.1 |
| Scpep1 | 12537.3 | 8882.5 | 12210.5 | NM_133383.1 |
| Scye1 | 2657.6 | 1960.8 | 2447.2 | XM_342344.2 |
| Sdf2l1_predicted | 464.6 | 338.2 | 421.7 | XM_237828.3 |
| Sec15l1 | 2215.2 | 772.7 | 2205.1 | NM_019277.1 |
| Sema4a_predicted | 9489.7 | 1973.4 | 9180.9 | XM_574973.1 |
| Sez6 | 227.8 | 118.9 | 208.9 | XM_239260.3 |
| Sf3b3_predicted | 3388.4 | 2256.7 | 3233.8 | XM_214697.3 |
| Sfrs10 | 7054.7 | 4697.4 | 6265.2 | NM_057119.1 |
| Sgpl1 | 996.2 | 571.8 | 952.5 | NM_173116.1 |
| Sgta | 3836 | 2734.9 | 3818.6 | NM_022703.2 |
| Shmt2 | 1467.8 | 1101.9 | 1437.9 | NM_001008322.1 |
| Siat10 | 448.9 | 265.4 | 433.4 | NM_207602.1 |
| Siat8d | 418.7 | 172.8 | 426.2 | XM_346078.2 |
| Slc15a3 | 2661.4 | 1721.7 | 2846.6 | NM_139341.1 |
| Slc16a3 | 9190.5 | 5554.2 | 8257.9 | NM_030834.1 |
| Slc38a6_predicted | 1875.4 | 1144.1 | 1675 | XM_216732.3 |
| Slco4a1 | 872.6 | 270.2 | 701.2 | NM_133608.1 |
| Smarca5_predicted | 997.2 | 728.8 | 1059.6 | XM_226380.3 |
| Smox_predicted | 2286.1 | 1009 | 1961.6 | XM_218704.3 |
| Smpd1 | 4626.6 | 3043.7 | 4144.8 | NM_001006997.1 |
| Snrp70_predicted | 2950.3 | 1952 | 2643.8 | XM_341857.2 |
| Snx10_predicted | 2989.8 | 1430.8 | 2487.2 | XM_216145.3 |
| Snx4_predicted | 2421.6 | 1499.9 | 2634.6 | XM_340997.2 |
| Socs2 | 439.8 | 271.4 | 467.8 | NM_058208.1 |
| Sod1 | 9323.4 | 6595.6 | 9519.5 | NM_017050.1 |

TABLE 7-continued

Day 3 restored decreased gene expression in HSCs.

| SYMBOL | Fresh HSC | Day 3 HSC | Day 3 HSC + VitD3 | ACCESSION |
|---|---|---|---|---|
| Sod2 | 3812.1 | 2431.5 | 4633 | NM_017051.2 |
| Spg21 | 4799.4 | 3167 | 4259.9 | NM_001006987.1 |
| Steap_predicted | 3726.3 | 2624.5 | 3724.1 | XM_216315.3 |
| Stx7 | 2267.9 | 1267.1 | 2081.7 | NM_021869.2 |
| Suclg1 | 3998.1 | 2853.7 | 3675.7 | NM_053752.1 |
| Sulf2_predicted | 5772.9 | 2414.7 | 4638.4 | XM_230861.3 |
| Tacc2 | 991.1 | 680.1 | 957.6 | NM_001004418.1 |
| Taf15_predicted | 736.9 | 496 | 787 | XM_237792.3 |
| Tagln | 4988.4 | 3089.5 | 4488.5 | XM_579512.1 |
| Taldo1 | 24419.9 | 15202.7 | 22175.2 | NM_031811.2 |
| Tax1bp1 | 3204.1 | 1978.4 | 3214.3 | NM_001004199.1 |
| Tbn_predicted | 337.9 | 236.5 | 345 | XM_236948.3 |
| Tce1_predicted | 2309.4 | 1646 | 2084 | XM_220230.3 |
| Tcn2 | 868.3 | 631 | 825.8 | NM_022534.1 |
| Tep1 | 4323 | 2132.5 | 3930.6 | NM_022591.1 |
| Them2_predicted | 704.1 | 423.7 | 660.3 | XM_214475.2 |
| Thrb | 1129.2 | 517.7 | 980.5 | NM_012672.1 |
| Tiam1_predicted | 1843.2 | 1173.1 | 1811.1 | XM_221672.3 |
| Timm22 | 2974.4 | 1675.2 | 2592.2 | XM_340856.2 |
| Timm23 | 7141.2 | 4519.9 | 6591.0 | NM_019352.1 |
| Tle3 | 1616.8 | 869 | 1549.6 | NM_053400.1 |
| Tlr2 | 6675.5 | 2536.6 | 5304.7 | NM_198769.2 |
| Tm4sf1_predicted | 296.9 | 207.1 | 302.7 | XM_215576.3 |
| Trpv2 | 5712.1 | 4020.4 | 5771.6 | NM_017207.1 |
| Txnrd3_predicted | 468.2 | 315 | 445.6 | XM_216204.3 |
| Ubtd1_predicted | 3802.6 | 1451.6 | 3111.5 | XM_219869.3 |
| Ugcg | 5583 | 3967.4 | 5844.1 | XM_579533.1 |
| Uqcrc1 | 4365.8 | 3050 | 3976.4 | NM_001004250.1 |
| Usp12_predicted | 730.3 | 354.7 | 735.5 | XM_341033.2 |
| Vcam1 | 477.4 | 213.9 | 434.8 | NM_012889.1 |
| Vcip135 | 1047.2 | 589.1 | 953.3 | NM_176857.2 |
| Vdr | 191.1 | 114.6 | 168.5 | NM_017058.1 |
| Wfdc2 | 332.2 | 229 | 320.7 | NM_173109.1 |
| Wsb1_predicted | 2542.5 | 1749.1 | 2364.5 | XM_220736.3 |
| Xbp1 | 19933.6 | 9169.3 | 18361.9 | NM_001004210.1 |
| Xpo4_predicted | 871.5 | 479.5 | 781.3 | XM_214191.3 |
| Zdhhc7 | 1545.5 | 512.1 | 1316.8 | NM_133394.1 |
| Zfp36l1 | 6871.2 | 2779.8 | 6168.9 | NM_017172.1 |
| Znf386 | 628.6 | 411.3 | 627.2 | NM_019620.1 |
| Znf532_predicted | 549.3 | 367.5 | 495.1 | XM_225923.3 |
| Znf593_predicted | 1845.3 | 1323.5 | 1683 | XM_216542.2 |
|  | 2539 | 1552.4 | 2356.2 | BC099090 |
|  | 634.7 | 275.1 | 550.6 | AY724532 |

TABLE 8

Day 3 reduction of induced gene expression in HSCs.

| GENE SYMBOL | Fresh HSC | Day 3 HSC | Day 3 HSC + VitD3 | ACCESSION |
|---|---|---|---|---|
| Abcg1 | 1799.6 | 4237.1 | 1665.5 | NM_053502.1 |
| Arg1 | 4573.4 | 7314.8 | 4220.6 | NM_017134.1 |
| Atp6v0a1 | 656.9 | 1939.8 | 714.1 | NM_031604.1 |
| Ccl12_predicted | 4325.2 | 14376.6 | 7897.7 | XM_213425.2 |
| Ccl4 | 2554.5 | 4061.0 | 3564.3 | NM_053858.1 |
| Ccr5 | 359.4 | 1526.9 | 391.4 | NM_053960.2 |
| Ch25h_predicted | 154.8 | 1978.6 | 224.6 | XM_220063.3 |
| Copeb | 3848.3 | 5874.9 | 3463.3 | NM_031642.1 |
| Cxcl2 | 936.1 | 1748.2 | 1325.7 | NM_053647.1 |
| Cxcr4 | 250.9 | 635.4 | 261.6 | NM_022205.1 |
| Id2 | 2998.5 | 10121.5 | 4063.4 | NM_013060.2 |
| Irf5_predicted | 544.1 | 826.6 | 505.2 | XM_216105.3 |
| LOC308350 | 120.3 | 327.4 | 151.9 | XM_218261.3 |
| LOC313563 | 284.6 | 590.9 | 305.6 | XM_233480.1 |
| LOC313563 | 268.5 | 574.9 | 323.5 | XM_233480.2 |
| LOC498245 | 621.5 | 1144.8 | 1229.1 | XM_573468.1 |
| LOC498623 | 330.8 | 694.8 | 521.7 | XM_573902.1 |
| LOC498741 | 289.5 | 496.3 | 314.1 | XM_574019.1 |
| LOC498979 | 184.7 | 367.8 | 280.6 | XM_574268.1 |
| LOC500285 | 765.5 | 1268.2 | 1242 | XM_575635.1 |
| LOC500343 | 198.4 | 449.8 | 331.2 | XM_575695.1 |
| LOC500380 | 189.4 | 382.2 | 303.8 | XM_575738.1 |
| LOC500883 | 127.4 | 231 | 187.7 | XM_576284.1 |
| LOC501156 | 246 | 438.1 | 335 | XM_576580.1 |
| LOC501503 | 231.2 | 505.3 | 386.7 | XM_576904.1 |
| Myo1g_predicted | 544 | 873.2 | 541.9 | XM_573653.1 |
| Ptpre | 173.6 | 345.9 | 182.3 | XM_341950.2 |
| Ptpro | 849.4 | 1573 | 893.7 | NM_017336.1 |
| Sgk | 6473.5 | 10549.7 | 5885.4 | NM_019232.1 |
| Stxbp1 | 481.4 | 859.7 | 492.4 | NM_013038.3 |

The information provided in Tables 7 and 8 allows one to understand the signaling pathways that VDR activation impacts upon in these cells, and thus deduce the effects that the treatment is likely to have in vivo.

Example 12

Bone Marrow Transplantation

This example describes methods that can be used to determine whether Kupffer cells are responsible for the results observed in Examples 6 and 7.

Bone marrow from VDR knock-out mice will be administered to irradiated mice. Thus, KC cells administered are null for VDR. Stellate cells are not replaced by the bone marrow. Mice will be treated with CCl4 and the effect of calcidiol on inflammatory and fibrosis markers determined as described in Example 6. If a decrease in inflammatory and fibrosis markers is observed in the presence of calcidiol, this indicates that KC are not significantly involved in this process, but that other HSC are, such as SEC or stellate cells.

Bone marrow transplantation (BMT) has been extensively utilized for studies of the immune system (Sonoda et al., 2007. *Genes Dev.*, 21(15):1909-20). 60 age-matched male VDRf/fTie2-cre mice are gamma-irradiated using a split dose protocol of 600 rads+600 rads (total dose=1200 rads) with a 4 hour break between doses, and followed the next day by reconstitution with 2 million bone marrow cells from UbC-GFP (60 recipients) or wild type mice (60 recipients) introduced via retro-orbital injection. This protocol ensures near complete reconstitution of bone marrow progenitors with the transplanted marrow (Cui et al., 2002. *Bone Marrow Transplant.*, 30:843-849). Transplanted mice receive Baytril (enrofloxacin 0.5 mg/ml)-treated water for 7 days following irradiation as prophylaxis for infection, and mice will be kept in autoclaved cages with sterile water for the duration of the study. After 4 weeks on a standard chow diet, peripheral blood will be collected by retro-orbital bleeds and genomic DNA will be extracted from whole blood using DNeasy columns (Qiagen). Genomic DNA will be utilized for PCR genotyping to confirm recipient mouse reconstitution with knockout or wild type marrow.

Example 13

VDR Protein is Inducible in Hepatocytes by TGF-$\beta_1$

This example describes methods used to demonstrate that contacting hepatocytes with TGF-$\beta_1$ causes hepatocytes to express VDR.

Primary rat hepatocytes were isolated from Sprague-Dawley rats by collagenase in situ perfusion and plated on collagen in Williams E medium. The immortalized human hepatocyte (IHH) cell line was cultured in DMEM/F12+ GlutaMax with insulin and dexamethasone. Primary rat hepatocytes or immortalized human hepatocytes were cultured for two days, then subsequently treated with TGF-$\beta_1$ (2 ng/mL human, recombinant expressed in CHO cells from Sigma-Aldrich, # T7039) for 24 hours and compared to untreated controls. Protein was prepared from harvested cells and western blotting for VDR was accomplished using a specific anti-VDR antibody (anti-human VDR antibody from R&D systems CAT # PP-H4537-00 and rat anti-VDR monoclonal antibody from Chemocon International CAT # MAB1360). Recombinant human VDR protein was included as a positive control.

Figure 14:
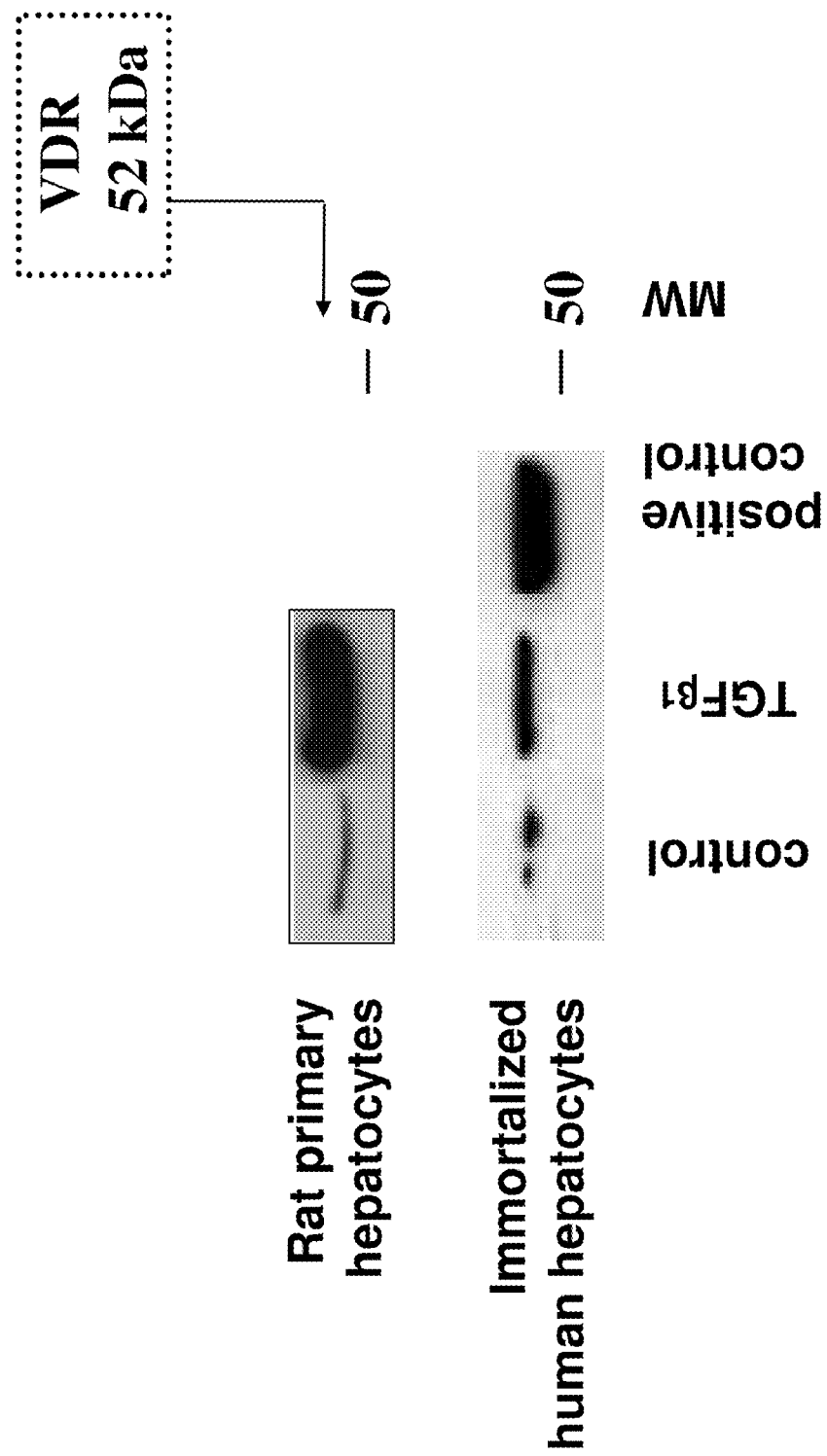
FIG. 14 is a digital image of a Western blot showing that the vitamin D receptor (VDR) protein is inducible in hepatocytes by TGF-$\beta_1$.

As shown in FIG. 14, a large increase in VDR expression following TGF-$\beta_1$, exposure was observed (at least about 5-fold).

Example 14

VDR Protein is Synergistically Induced by TGF-$\beta_1$ and VDR Agonist

This example describes methods used to demonstrate that contacting hepatocytes with both TGF-$\beta$1 and the VDR agonist calcitriol causes a synergisitic effect on VDR expression by hepatocytes.

Rat hepatocytes were cultured as described in Example 13 and two days later treated with TGF-$\beta_1$ (2 ng/mL; Sigma-Aldrich # T7039), VDR agonist calcitriol (1$\alpha$,25(OH)$_2$ D$_3$) (10 nM; Sigma-Aldrich # D1530), or both, for 24 hours and compared to untreated controls. Messenger RNA for rat VDR was measured using real-time quantitative PCR (QPCR) (ratVDR forward 5'-acccttgggctctactcacc-3' SEQ ID NO: 15; ratVDR reverse 5'-gttccggtcaaagtcaccag-3' SEQ ID NO: 16).

Figure 15:
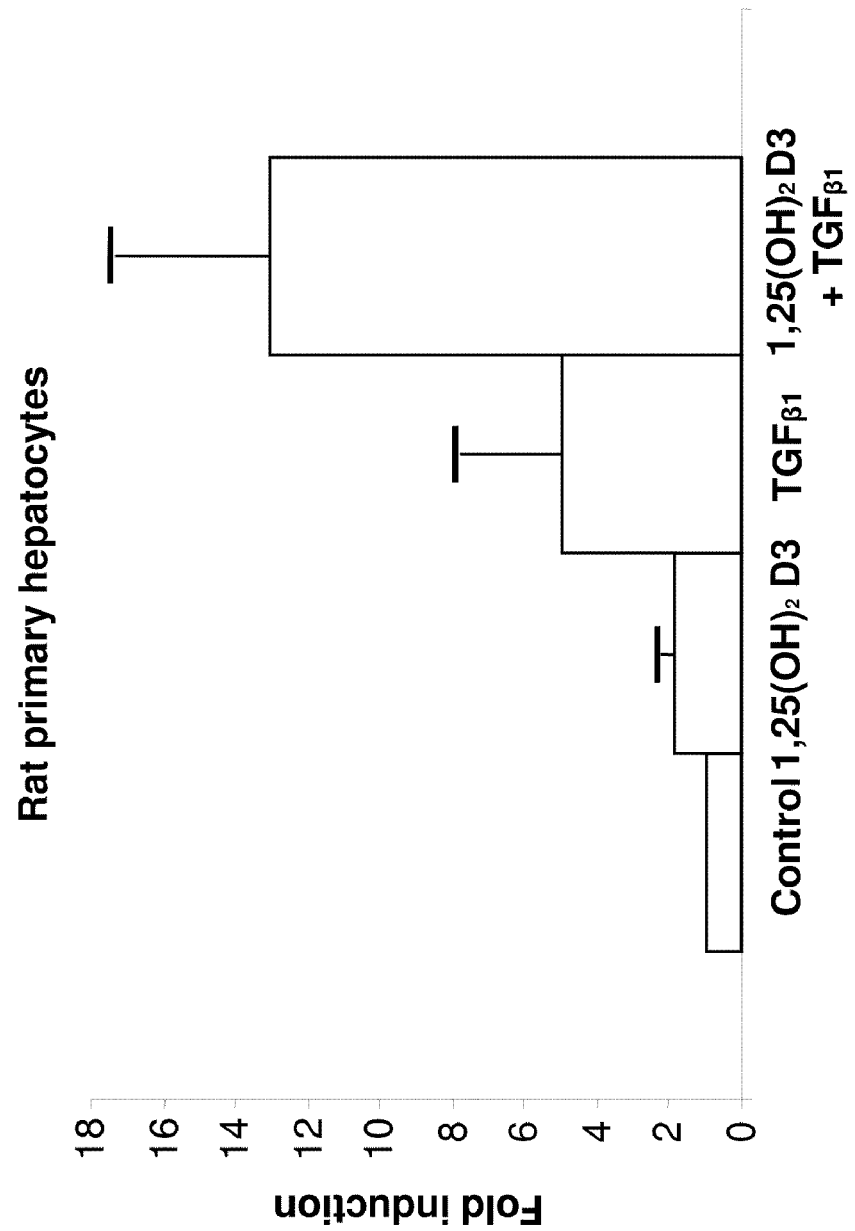
FIG. 15 is a bar graph showing that VDR expression in primary rat hepatocytes is synergistically induced by co-treatment with TGF-$\beta_1$ (2 ng/mL) and the VDR agonist calcitriol ($1\alpha,25(OH)_2$ D3) (10 nM). Error bars indicate standard deviation.

As shown in FIG. 15, both TGF-$\beta_1$ and calcitriol are capable of inducing VDR expression and that the combination was the most effective method of eliciting VDR expression, for example increasing expression by at least 10-fold, such as at least 12-fold. Thus, not only does TGF-$\beta_1$ exposure allow hepatocytes to become responsive to VDR agonist ligands, but VDR agonists further increase VDR expression.

Example 15

VDR Protein Expressed by Hepatocytes is Functional

This example describes methods used to demonstrate that the VDR expressed by hepatocytes following treatment with both TGF-$\beta_1$ and the VDR agonist calcitriol is functional.

Cyp24a1 is classic target gene of ligand-activated VDR and is a well-validated measure of VDR responsiveness. Primary rat hepatocytes were cultured and treated as described in Example 14. Messenger RNA for rat Cyp24a1 was measured using real-time quantitative PCR (QPCR) as described in the Examples above.

Figure 16:
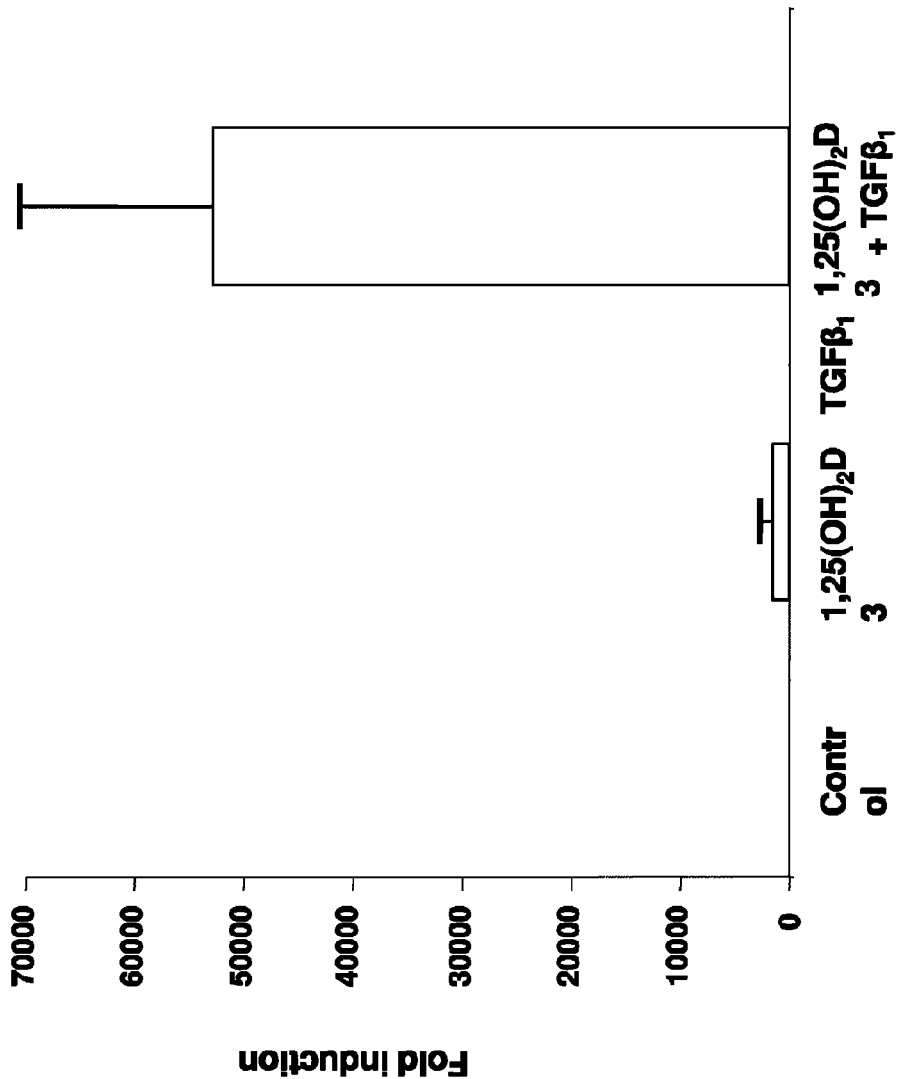
FIG. 16 is a bar graph showing increased Cyp24a1 expression in primary rat hepatocytes following treatment with TGF-$\beta_1$ and the VDR agonist calcitriol ($1\alpha,25(OH)_2$ D3), confirming that functional VDR is induced in these cells by TGF-$\beta_1$. Error bars indicate standard deviation.
Figure 17:
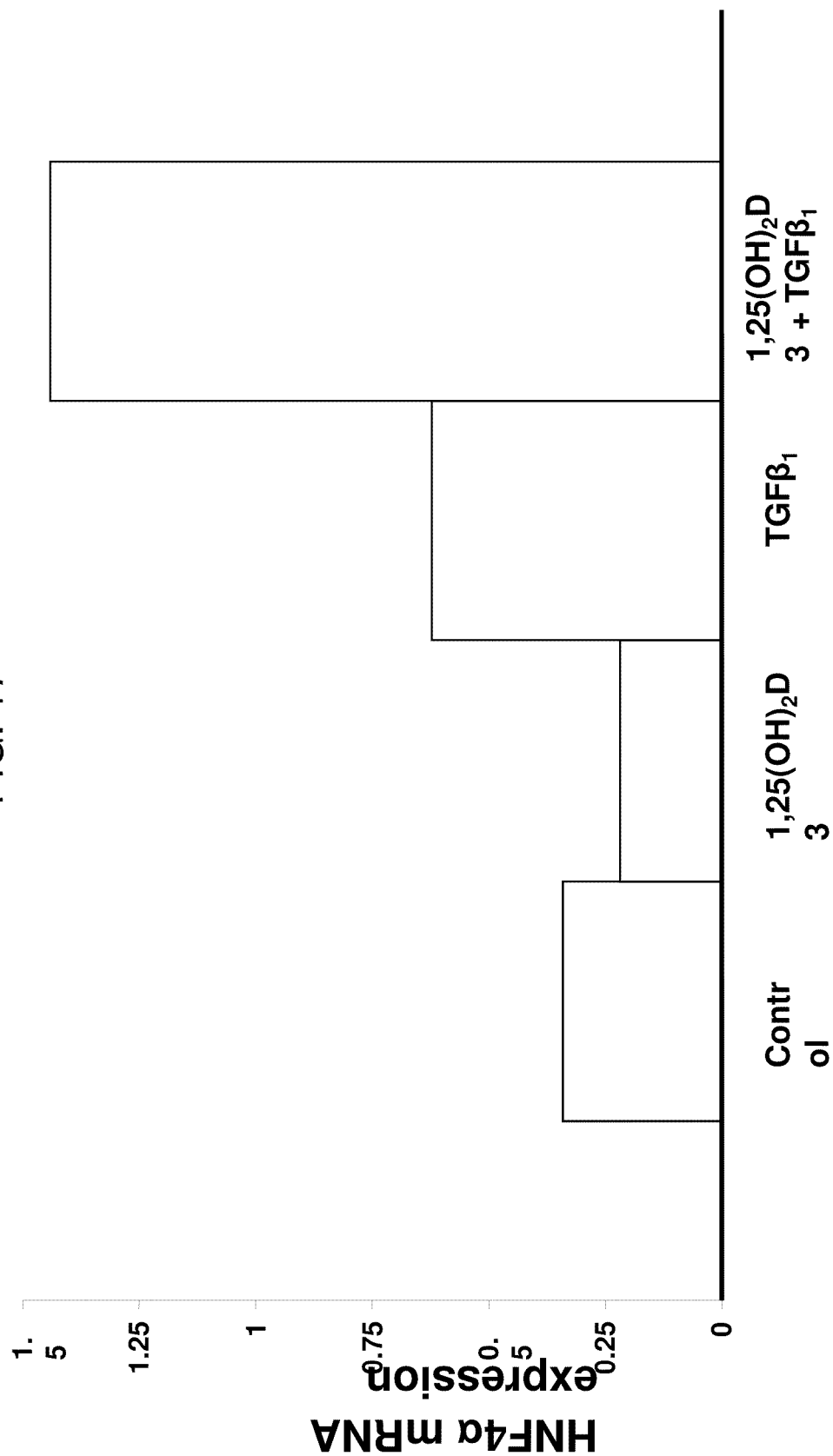
FIG. 17 is a bar graph showing that treatment of human immortalized hepatocyte (IHH) cell line with a combination of TGF-$\beta_1$ and calcitriol ($1\alpha,25(OH)_2$ D3) increases expression of the nuclear hormone receptor HNF4$\alpha$, a crucial differentiation factor for hepatocytes.

As shown in FIG. 16 calcitriol (1,$\alpha$25(OH)$_2$ D$_3$) treatment alone resulted in only a minor increase in Cyp24a1 expression. TGF-$\beta_1$ treatment in the absence of a VDR agonist ligand had no effect of Cyp24a1 expression, as VDR expressed by the hepatocytes induced by TGF-$\beta_1$ is not active until exposed to a VDR ligand. However, the combination of calcitriol and TGF-$\beta_1$ resulted in a significant induction of Cyp24a1, demonstrating that the VDR expressed by the hepatocytes is functional. This illustrates that during the fibrotic process hepatocytes are exposed to TGF-$\beta_1$, the majority of which is thought to be produced locally within the liver by hepatic NPCs and possibly recruited inflammatory cells. This renders the hepatocytes therapeutically sensitive to treatment with vitamin D, its metabolic derivatives such as 1,$\alpha$25(OH)$_2$ D3 and or synthetic VDR ligands.

Example 16

TGF-$\beta_1$ and VDR Agonist Increase Expression of HNF4$\alpha$

This example describes methods used to demonstrate that the treatment with both TGF-$\beta_1$ and the VDR agonist calcitriol increases expression HNF4$\alpha$, a crucial differentiation factor for hepatocytes. As many metabolizing and transporting genes in hepatocytes rely on the nuclear hormone receptor hepatocyte nuclear factor 4a (HNF4α) for their expression, mRNA for this receptor was measured in cultured primary rat hepatocytes by QPCR.

Cultured primary rat hepatocytes were treated as described in Example 14. Messenger RNA for rat Hnf4α was measured using real-time quantitative PCR (QPCR) (Forward: 5'-gagatccatggtgttcaagga-3' SEQ ID NO: 17; Reverse: 5'-gt-gccgagggacaatgtagt-3' SEQ ID NO: 18).

As shown in FIG. 16 calcitriol (1,α25(OH)$_2$D3) or TGF-β$_1$ treatment alone resulted in some increase in HNF4α expression. However, the combination of calcitriol and TGF-β$_1$ resulted in a significant induction of HNF4α or example increased expression by at least 3-fold). As HNF4α is a key differentiation and survival factor for hepatocytes (for example see Watt et al., *Heptology*, 37:49-53, 12003, herein incorporate by reference), production of HNF4α within hepatocytes will serve to limit liver injury and therefore fibrosis.

Example 17 mRNA Expression by Hepatocytes Following Treatment with TGF-β$_1$ and VDR Agonist This example describes methods used to detect mRNA expressed by hepatocytes following treatment with TGF-β1, the VDR agonist calcitriol, or both, in order to determine the gene targets of VDR in hepatocytes.

Cells were cultured and treated as described in Example 14. Gene expression was determined using Illumina Sentrix expression arrays, rat version 1, according to the manufacturer's instructions.

Table 9 shows genes that are positively regulated by VDR activation in hepatocytes, which includes predominantly metabolizing enzymes and transporting genes involved in the elimination of toxic metabolites from the liver. In contrast, Table 10 shows genes that were negatively regulated by VDR activation, which includes predominantly of inflammation and immune-related genes. Triplicate biologic replicates were assayed for each treatment.

TABLE 9

Genes positively regulated by VDR activation.

| locus | TGF-β$_1$ (gene expression) | TGF-β$_1$ + Calcitriol (fold change over TGFβ1 alone) | p-value |
|---|---|---|---|
| cyp24a1 | 56.9 | 27.744 | 8.7E-182 |
| slc39a1 | 489.71 | 1.946 | 3.55E-36 |
| cyp2c22 | 2009.34 | 1.818 | 3.01E-30 |
| Gstm2 | 715.15 | 1.457 | 9.29E-14 |
| Slc25a4 | 671.16 | 1.402 | 1.63E-11 |
| cyp2a1 | 216.95 | 1.39 | 4.98E-11 |

TABLE 9-continued

Genes positively regulated by VDR activation.

| locus | TGF-β$_1$ (gene expression) | TGF-β$_1$ + Calcitriol (fold change over TGFβ1 alone) | p-value |
|---|---|---|---|
| slc26a1 | 181.21 | 1.383 | 9.61E-11 |
| cyp4a10 | 91.71 | 1.365 | 4.79E-10 |
| Abcg4 | 95.82 | 1.359 | 8.33E-10 |
| slc25a1 | 1375.94 | 1.357 | 9.85E-10 |
| slc25a5 | 2038.43 | 1.344 | 2.98E-09 |
| Cyp2d5 | 338.34 | 1.344 | 2.88E-09 |
| Abcg2 | 913.91 | 1.341 | 3.90E-09 |
| Slc7a6os | 241.22 | 1.313 | 3.94E-08 |
| Slc35a4 | 157.88 | 1.295 | 1.78E-07 |
| Cyp1a2 | 135.53 | 1.293 | 1.97E-07 |
| Slc37a4 | 246.55 | 1.289 | 2.84E-07 |
| Slc25a19 | 195.9 | 1.286 | 3.42E-07 |
| Slc28a1 | 50.32 | 1.284 | 4.18E-07 |
| Ugt2b5 | 155.32 | 1.283 | 4.43E-07 |
| Gstm1 | 2230.15 | 1.283 | 4.56E-07 |
| Slc28a2 | 157.29 | 1.279 | 5.91E-07 |
| Gsto1 | 1364.06 | 1.278 | 6.56E-07 |
| Cyp2d1 | 147.68 | 1.276 | 7.44E-07 |
| Cyp3a23/3a1 | 380.28 | 1.273 | 9.56E-07 |
| Abcb4 | 96.93 | 1.271 | 1.11E-06 |

TABLE 10

Genes negatively regulated by VDR activation.

| locus | TGF-β$_1$ (gene expression) | TGF-β$_1$ + Calcitriol (fold change over TGF-β$_1$ alone) | p-value |
|---|---|---|---|
| Jak2 | 669.28 | 0.777 | 7.24E-07 |
| Tlr7 | 110.03 | 0.745 | 1.20E-08 |
| Nos2 | 90.7 | 0.73 | 1.37E-09 |
| Mmp9 | 159.27 | 0.722 | 4.11E-10 |
| Cd44 | 680.16 | 0.72 | 2.86E-10 |
| Ccl7 | 1303.89 | 0.714 | 1.23E-10 |
| Cxcr4 | 164.68 | 0.642 | 1.80E-16 |
| Il1a | 675.41 | 0.632 | 2.23E-17 |
| Tlr2 | 978.98 | 0.6 | 1.23E-20 |
| Ccl4 | 380.06 | 0.409 | 3.59E-48 |
| Ccl12 | 368.02 | 0.397 | 2.42E-50 |
| Ccl3 | 540.53 | 0.3 | 2.87E-70 |
| Il1b | 1551.37 | 0.228 | 1.96E-87 |

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of treating pancreatic fibrosis in a subject having pancreatic fibrosis, comprising:
   administering a therapeutically effective amount of a compound selected from the group consisting of 25-hydroxy-$D_3$ (25-OH-$D_3$) (calcidiol); vitamin D3 (cholecalciferol); vitamin D2 (ergocalciferol), 1α, 25-dihydroxyvitamin $D_3$ (calcitriol), calcipotriol, and combinations thereof to a subject having pancreatic fibrosis, thereby treating the fibrosis.

2. The method of claim 1, wherein administration comprises oral administration of the compound.

3. The method of claim 1, wherein the compound is administered at a dose of from about 5 international units (IU) to about 50,000 IU.

4. The method of claim 1, wherein administration comprises contacting pancreatic stellate cells with the compound, thereby treating the fibrosis.

5. The method of claim 1, wherein the subject is a mammalian subject.

6. The method of claim 1, wherein the compound is calcipotriol.

7. The method of claim 1, wherein the compound is 25-hydroxy-$D_3$ (25-OH-$D_3$) (calcidiol).

8. The method of claim 1, wherein the compound is vitamin D3 (cholecalciferol).

9. The method of claim 1, wherein the compound is vitamin D2 (ergocalciferol).

10. The method of claim 1, wherein the compound is 1α, 25-dihydroxyvitamin $D_3$ (calcitriol).

11. The method of claim 1, wherein the subject is a human.

12. A method of treating pancreatic fibrosis in a human subject having pancreatic fibrosis, comprising:
   administering a therapeutically effective amount of a calcipotriol to a human subject having pancreatic fibrosis, thereby treating the fibrosis.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide primer.

<400> SEQUENCE: 1
ggctcctatg cccacctc                                                  18

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 2
cacagccttt agcaggggta                                                20

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 3
agatcaaacc ttggaaagcc ta                                             22

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer.

<400> SEQUENCE: 4
gccactcctg tccttccag                                                 19

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 5
ttccagctat ttctacgagg ctat                                           24

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide primer.

<400> SEQUENCE: 6
ccgtacttgg ccttgttca                                                 19

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 7
catcatggcc atcaaaacaa t                                              21

<210> SEQ ID NO 8
<211> LENGTH: 19

```
<212> TYPE: DNA
<213> ORGANISM: Artificial Sequence
<220> FEATURE:
<223> OTHER INFORMATION: Synthetic oligonucleotide primer.

<400> SEQUENCE: 8
gcagctcgac tggagtgac                                              19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide primer.

<400> SEQUENCE: 9
ctcatggctg gagtggaca                                              19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide primer.

<400> SEQUENCE: 10
acacccacca cttcctcgt                                              19

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide primer.

<400> SEQUENCE: 11
cttgcggact gctcactg                                               18

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 12
cgcagactac gttgttcagg                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 13
gctatagcaa acaccccagg                                             20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 14
gatcagggct gttctctcct t                                           21
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 15
acccttgggc tctactcacc                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 16
gttccggtca aagtcaccag                                                 20

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 17
gagatccatg gtgttcaagg a                                               21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 18
gtgccgaggg acaatgtagt                                                 20
```